US007750134B2

(12) United States Patent
Godzik et al.

(10) Patent No.: US 7,750,134 B2
(45) Date of Patent: Jul. 6, 2010

(54) NUCLEIC ACIDS ENCODING MICROBIAL SUMO PROTEASE HOMOLOGS

(75) Inventors: Adam Godzik, San Diego, CA (US); John C. Reed, Rancho Santa Fe, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 733 days.

(21) Appl. No.: 10/301,533

(22) Filed: Nov. 20, 2002

(65) Prior Publication Data

US 2003/0203473 A1 Oct. 30, 2003

Related U.S. Application Data

(60) Provisional application No. 60/331,895, filed on Nov. 20, 2001.

(51) Int. Cl.
*C07H 21/04* (2006.01)
*C12N 9/48* (2006.01)

(52) U.S. Cl. ..................................... 536/23.2; 435/212

(58) Field of Classification Search ........................ None
See application file for complete search history.

(56) References Cited

U.S. PATENT DOCUMENTS 6,589,738 B1 * 7/2003 Forsyth et al. .................. 435/6

OTHER PUBLICATIONS

PIR_80 database Accession No. E91023 Jul. 18, 2001 Hayashi et al. Complete genome sequence of enterohemorrhagic *E. coli* O157:H7.*
GenEmbl database Accession No. ECU58768 Jun. 20, 1996 Huisman G.W. Characterization of the ela locus from *E. coli*.*
Issued_Patents_NA database from US 6,589,738 Forsyth et al. Jul. 8, 2003 Genes essential for microbial proliferation . . . SEQ ID No. 158. Alignment with SEQ ID No. 27.*
Pending_Applications database from U.S. Appl. No. 60/164,158 Bauer et al filed Nov. 9, 1999 Genes essential for microbial proliferation . . . SEQ ID No. 158. Alignment with SEQ ID No. 27.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
USPTO in house BLAST alignment SEQ ID No. 2 vs NCBI Acc. No. NP_416772.1. Performed Jan. 11, 2010.*
NCBI •gi|161784282|sp|Q47013.3|ELAD_ECOLI identical sequences. Performed Jan. 11, 2010.*
Alcalay et al., "The promyelocytic leukemia gene product (PML) forms stable complexes with the retinoblastoma protein," *Mol. Cell. Biol.*, 18:1084-1093 (1998).
Alouani, "Scintillation proximity binding assay," *Methods Mol. Biol.*, 138:135-41 (2000).
Andrés et al., "African swine fever virus protease, a new viral member of the SUMO-1-specific protease family," *J. Biol. Chem.*, 276:780-787 (2001).
Balla et al., "Molecular targets for pharmacological cytoprotection," *Biochem. Pharmacol.*, 61:769-777 (2001).
Bayer et al., "Structure determination of the small ubiquitin-related modifier SUMO-1," *J. Mol. Biol.*, 280:275-286 (1998).
Bloch et al., "Structural and functional heterogeneity of nuclear bodies," *Mol. Cell. Biol.*, 19:4423-4430 (1999).
Buschmann et al., "SUMO-1 modification of Mdm2 prevents its self-ubiguitination and increases Mdm2 ability to ubiguitinate p53.," *Cell*, 101:753-762 (2000).
Chen and Shapiro, "Affinity NMR," *Anal. Chem.*, 71:669A-675 A (1999).
Cornelis, "Molecular and cell biology aspects of plague," *Proc. Natl. Acad. Sci. U S A*, 97:8778-8783 (2000).
Cowman, "Functional analysis of drug resistance in *Plasmodium falciparum* in the post-genomic era," *Int. J. Parasitol.*, 31:871-878 (2001).
Daniel, "Dissecting the pathways to death," *Leukemia*, 2035-2044 (2000).
Degterev et al., "Identification of small-molecule inhibitors of interaction between the BH3 domain and Bcl-$x_L$," *Nature Cell Biol.*, 3:173-182 (2001).
Desterro et al., "SUMO-1 modification of IκBα inhibits NF-κB activation," *Molecular Cell*, 2:233-239 (1998).
Deveraux et al., "X-linked IAP is a direct inhibitor of cell-death proteases," *Nature*, 388:300-304 (1997).
Ding et al., "Crystal structure of the human adenovirus proteinase with its 1 amino acid factor," *EMBO J.*, 15:1778-1783 (1996).
Everett, "A surprising role for the proteasome in the regulation of herpesvirus infection," *Trends. Biochem. Sci.*, 24:293-295 (1999).
Everett et al., "A novel ubiquitin-specific protease is dynamically associated with the PML nuclear domain and binds to a herpesvirus regulatory protein," *EMBO J.*, 16:566-577 (1997).
Everett et al., "The ability of herpes simple virus type 1 immediate-early protein Vmw110 to bind to a ubiquitin-specific protease contributes to its roles in the activation of gene expression and stimulation of virus replication," *J. Virol.*, 73:417-426 (1999).
Fancy, D., "Elucidation of protein-protein interactions using chemical cross-linking or label transfer techniques," *Curr. Opin. Chem. Biol.*, 4:28-33 (2000).
Finlay and Brumell, "*Salmonella* interactions with host cells: in vitro to in vivo," *Philos. Trans. R. Soc. Lond. B. Biol. Sci.*, 355:623-631 (2000).

(Continued)

*Primary Examiner*—Sheridan Swope
(74) *Attorney, Agent, or Firm*—McDermott Will & Emery LLP

(57) ABSTRACT

The invention provides isolated SUMO-specific protease-like (or "SSP") domain-containing polypeptides from microorganisms, including bacteria, protozoans and yeast, including *Escherichia, Salmonella, Pseudomonas, Chlamydia, Plasmodium, Trypanosma, Mesorhizobium, Rickettsia, Cryptosporidium* and *Candida* species. The invention further provides modifications of such polypeptides, functional fragments therefrom, encoding nucleic acid molecules and specific antibodies. Also provided are methods for identifying polypeptides and compounds that associate with or modulate the activity of the SSP domain-containing polypeptides. Further provided are methods of modulating a biological activity in a cell, and treating pathological conditions, using the described nucleic acid molecules, polypeptides and compounds.

9 Claims, 4 Drawing Sheets

OTHER PUBLICATIONS

Gao and Kwaik, The modulation of host cell apoptosis by intracellular bacterial pathogens,*Trends Microbiol.*, 8:306-313 (2000).
Gilligan, "*Escherichia coli.* EAEC, EHEC, EIEC, ETEC," *Clin. Lab. Med.*, 19:505-521 (1999).
Gostissa et al., "Activation of p53 by conjugation to the ubiguitin-like protein SUMO-1," *EMBO J.*, 18:6462-6471 (1999).
Hajduk et al., "High-throughput nuclear magnetic resonance-based screening," *J. Med. Chem.*, 42:2315-2317 (1999).
Haraguchi et al., "Apoptotic protease activating factor 1 (Apaf-1)?-independent cell death suppression by Bcl-2," *J. Exp. Med.*, 191:1709-1720 (2000).
Hengartner, "The biochemistry of apoptosis," *Nature*, 407:770-776 (2000).
Hirano and Upper, "Bacteria in the leaf ecosystem with emphasis on *Pseudomonas syringae*-a pathogen, ice nucleus, and epiphyte," *Microbiol. Mol. Biol. Rev.*, 64:624-653 (2000).
Ishov et al., "PML is critical for ND10 formation and recruits the PML-interacting protein daxx to this nuclear structure when modified by SUMO-1," *J. Cell Biol.*, 147:221-234 (1999).
Karin and Ben-Neriah, "Phosphorylation meets ubiguitination: the control of NF-κB activity," *Annual Rev. Immunol.*, 18:621-663 (2000).
Kim et al., "A new SUMO-1-specific protease, SUSP1, that is highly expressed in reproductive organs," *J. Biol. Chem.*, 275:14102-14106 (2000).
Krammer, "CD95's deadly mission in the immune system," *Nature*, 407:789-795 (2000).
Lallemand-Breitenbach et al., "Role of promyelocytic leukemia (PML) sumolation in nuclear body formation, 11S proteasome recruitment, and $As_2O_3$-induced PML or PML/retinoic acid receptor α degradation," *J. Exp. Med.*, 193:1361-1371 (2001).
LaMorte et al., "Localization of nascent RNA and CREB binding protein with the PML-containing nuclear body," *Proc. Natl. Acad. Sci. USA*, 95:4991-4996 (1998).
Li and Hochstrasser, "A new protease required for cell-cycle progression in yeast," *Nature*, 398:246-251 (1999).
Li and Hochstrasser, "The yeast ULP2 (*SMT4*) gene encodes a novel protease specific for the ubiquitin-like Smt3 protein," *Mol. Cell. Biol.*, 20:2367-2377 (2000).
Li et al., "Saturated BLAST: an automated multiple intermediate sequence search used to detect distant homology," *Bioinformatics*, 16:1105-1110 (2000).
Lin and Ghosh "A glycine-rich region in NF-κB p105 functions as a processing signal for the generation of the p50 subunit," *Mol. Cell. Biol.*, 16:2248-2254 (1996).
Mattsson et al., "Proteins associated with the promyelocytic leukemia gene product (PML)-containing nuclear body move to the nucleolus upon inhibition of proteasome-dependent protein degradation," *Proc. Natl. Acad. Sci. USA*, 98:1012-1017 (2001).
McLafferty et al., "Biochemistry: biomolecule mass spectrometry," *Science*, 284:1289-1290 (1999).
Meier et al., "Apoptosis in development," *Nature*, 407:796-801 (2000).
Meijer et al., "The bacterial protein YopJ abrogates multiple signal transduction pathways that converge on the transcription factor CREB," *Cell. Microbiol.*, 2:231-238 (2000).
Melchior and Hengst, "Mdm2-SUMO1: is bigger better?," *Nature Cell Biol.*, 2:E161-E163 (2000).
Monack et al., "*Yersinia* signals macrophages to undergo apoptosis and YopJ is necessary for this cell death," *Proc. Natl. Acad. Sci. USA*, 94:10385-10390 (1997).
Moon et al., "A cell-based assay system for monitoring NF-κB activity in human HaCat transfectant cells," *Anal. Biochem.*, 292:17-21 (2001).
Morgan et al., "Breakpoints of the t(11;18)(q21;q21) in mucosa-associated lymphoid tissue (MALT) lymphoma lie within or near the previously undescribed gene MALT1 in chromosome 18," *Cancer Res.*, 59:6205-6213 (1999).
Mossessova and Lima, "Ulp1-SUMO crystal structure and genetic analysis reveal conserved interactions and a regulatory element essential for cell growth in yeast," *Mol. Cell.*, 5:865-876 (2000).
Muller et al., "Conjugation with the ubiquitin-related modifier SUMO-1 regulates the partitioning of PML within the nucleus," *EMBO J.*, 17:61-70 (1998).
Muller et al., "SUMO, ubiguitin's mysterious cousin," *Nature Reviews*, 2:202-210 (2001).
Nassar, "Management of urinary tract infections," *J. Med. Liban.* 48:278-282 (2000).
Nicholson, "From bench to clinic with apoptosis-based therapeutic agents," *Nature*, 407:810-816 (2000).
Orth et al., "Disruption of signaling by *Yersinia* effector YopJ, a ubiguitin-like protein protease," *Science*, 290:1594-1597 (2000).
Reed, "Apoptosis," *Meth. Enz.*, vol. 322, Chapters 1-5, pp. 3-62, Chapters 15-17, pp. 177-201, Chapters 24-25, pp. 255-274 (2000).
Renard et al., "Development of a sensitive multi-well colorimetric assay for active NF-κB," *Nucleic Acids Res.*, 29:E21 (2001).
Rich et al., "Defying death after DNA damage," *Nature*, 407:777-783 (2000).
Rodriguez et al., "SUMO-1 modification activates the transcriptional response of p53," *EMBO J.*, 18:6455-6461 (1999).
Ruscher et al., "A fluorescence based non-radioactive electrophoretic mobility shift assay," *J. Biotech.*, 78:163-170 (2000).
Rychlewski et al., "Comparison of sequence profiles. Strategies for structural predictions using sequence information," *Protein Sci.*, 9:232-241 (2000).
Savill and Fadok, "Corpse clearance defines the meaning of cell death," *Nature*, 407:784-788 (2000).
Schwienhorst et al., "SUMO conjugation and deconjugation," *Mol. Gen. Genet.*, 263:771-786 (2000).
Schreck et al., "The NF-κB transcription factor induces DNA bending which is modulate by its 65-kD subunit," *Nucleic Acids Res.*, 18:6497-6502 (1990).
Shuker et al., "Discovering high-affinity ligands for proteins: SAR by NMR," *Science*, 274:1531-1534 (1996).
Smith and Bailey, "Human African trypanosomiasis in south-eastern Uganda: clinical diversity and isoenzyme profiles," *Ann. Trop. Med. Parasitol.*, 91:851-856 (1997).
Strasser et al., "Apoptosis signaling," *Annu. Rev. Biochem.*, 69:217-245 (2000).
Su et al., "DNA damage and activated caspase-3 expression in neurons and astrocytes: evidence for apoptosis in frontotemporal dementia," *Exp. Neurol.*, 163:9-19 (2000).
Sun et al., "Autoregulation of the NF-κB transactivator RelA (p65) by multiple cytoplasmic inhibitors containing ankyrin motifs," *Proc. Natl. Acad. Sci. USA*, 91:1346-1350 (1994).
Tatusova and Madden, "BLAST2 Sequences, a new tool for comparing protein and nucleotide sequences," *FEMS Microbiol. Lett.*, 174:247-250 (1999).
Uren et al., "Identification of paracaspases and metacaspases: two ancient families of caspase-like proteins, one of which plays a key role in MALT lymphoma," *Mol. Cell*, 6:961-967 (2000).
Vaux et al., "An evolutionary perspective on apoptosis," *Cell*, 76:777-779 (1994).
Wang et al., "Role of PML in cell growth and the retinoic acid pathway," *Science*, 279:1547-1551 (1998).
Weinberger et al., "Recent trends in protein biochip technology," *Pharmacogenomics*, 1:395-416 (2000).
Xu et al., "Assays for studying Bax-induced lethality in the yeast *Saccharomyces cerevisiae,*" *Meth. Enz.*, 332:283-296 (2000).
Yamamura et al., "*Methods in Neurotransmitter Receptor Analysis,*"Raven Press, (New York, 1990).
Yew, "Ubiguitin-mediated proteolysis of vertebrate G1-and S-phase regulators," *J. Cell Physiol.*, 187:1-10 (2001).
Yuan and Yankner, "Apoptosis in the nervous system," *Nature*, 407:802-809 (2000).
Zabel et al., "Nuclear uptake control of NF-κB by MAD-3, an I-κB protein present in the nucleus," *EMBO J.*, 12:201-211 (1993).
Zhong et al., "Role of SUMO-1-modified PML in nuclear body formation," *Blood*, 95:2748-2752 (2000).
dbj: BA000007.
dbj: BA000012.

* cited by examiner

A

```
            *                     *
278  HWLLVIVDIQARRLVYFDSLYNY-VMSPEDMEKDLQSFAQQLDQVYPAYDSQKFSVKIAA  343
     HW L+ VD++ R + YFDS          P+ + K LQ+ A + D++    D  +
465  HWSLISVDVRRRTITYFDSQRTLNRRCPKHIAKYLQAEAVKKDRL----DFHQGWKGYFK  520

*
344  KEVIQKGSGSSCGAWCCQFL-HWYLRDPFTDALNDLP  407
        V ++ + S CGA+  Q+  H L  PF+    D+P
521  MNVARQNNDSDCGAFVLQYCKHLALSQPFSFTQQDMP  557
```

B

```
128      GDEIPLISEKQS--LSKVLLNDENNELSDGTNFWDKNRQLTT--------
1        GSLVPELNEKDDDQVQKALASRENTQLMNRDNIEITVRDFKTLAPRRWLN

168      DE-IACYLQKIAANAKNTQVNYPTGLYVPYSTRTHLEDALNENIKSDPSW
51       DTIIEFFMKYIEKSTPNTVA-FNSFFYTNLSERGYQGVRRWMKRKKTQID

217      PNEVQLFPINTGG-HWILVSLQKIVNKKNNKLQIKCVIFNSLRALGYDKE
100      KLDKIFTPINLNQSHWALG----IIDLKKKT------IGYVDSLSNGPN

266      NSLKRVINSFNSELMGEMSNNNIKVHLNEPEIIFLHADLQQYLSQSCGAF
139      AMSFAILTDLQKYVMEESKHTIGEDFDLIHLDC-----PQQPNGYDCGIY

316      VCMAAQEVIEQRESNSDSAPYTLLKNHADRFKKYSAEEQYE
184      VCMNT-------LYGSADAPLDFDYKDAIRMRRFIAHLILT
```

C

```
427  VFRNGNQDEVLSEAFRLTITRKD--IQTLNHLNWLNDEIINFYMNMLMERSKEKGLPS-V  483
       + + +  +            +D + +  +WL D ++ Y N L R +E+    +
489  ALPPMSPERIDVDNLPFPQDVEDPELPQVTETSWLLDGHLHAYTNDLARRLQEESNAHLL  548

484  HAFNTFFFTKLKTA----GYQAVKRWTKKVDVFSVDILLVPIHL-GVHWCLAVVDFRKKN  538
     H  ++    T L +        A++R        + I +PI+   VHW L VVD R  +
549  HFADSQIVTMLNSEDEAQRNVALRRLVGDAVNPAPPIAFMPINRDNVHWSLLVVDRRDNH  608

539  ---ITYYDSMGGINNEACRILLQYLKQESIDKKRKEFDTNGWQLFSKKSQIPQQMNGSDC  595
        +YDSMG  +        + Q  +      +       K     Q +G  C
609  SPAAYHYDSMGTPHPH-----QHWHAQMA------AWRLGLDASQVYKMPTAIQPDGYSC  657

596  GMFACKYADCITKDRP  611
     G             + +
658  GDHVLTGIEVLAHRVI  673
```

```
456    LNWLNDEIINFYMNMLMERSK---EKGLPSVHAFNTFFFTKLKTAGYQAVKRWTKKVDVF 512
         L DE I     L ++ +            +       L+   Q   +    + +
1429   TQLLGDEHIQRDYEFLEQQLQQADPALAARTRLVDPSVSHLLRHMEQQDARGTLQSIYNR 1488

513    SV---DILLVPIHLGV------HWCLAVVDFRKKNI---TYYDSMGGINNEACRILLQYL 560
         +    D L VP++ GV       HW L +VD R      +YDS+
1489   NAGPSDFLFVPVNDGVGIDRGTHWSLLLVDRRDPERAVAYHYDSIQQNE---------- 1537
                                                 *
561    KQESIDKKRKEFDTNGWQLFSKKSQIPQQMNGSDCGMFACKYADCITK 608
         Q   D    ++    T           + QQ N DCG+F           + +
1538   -QRYNDAPARKLATRLDATLV-TPDMAQQKNAVDCGVFVVDGTRELVR 1583
```

E

```
105    LVPIHLG-VHWCLAVVDFRKK-NITYYDSMGGINNEACRILLQYLKQESIDKKRKEFDTN 162
         ++P++ G  HW L +       K NI +          E       + + +       +
488    IIPLNTGHKHWLLLMASKDDKGNINFM--YNDPYGEPLESRPKVTEYITEIYPDAKITDL 545

163    GWQLFSKKSQIPQQMNGSDCGMFACKYADCITKDRPINFTQQ---HMPYFRKRMVWEIL 218
                     QQ N DCG+F C A  ++K + I  T++         RK     +L
546    ---------NTKQQENVYDCGVFVCDSAIKLSKGQKILTTEESKDQGINLRKAQANTLL 595
```

F

```
2      SLVPELNEKDDDQVQKALASRENTQLMNRDNIEITVRDFKTLAPRRWLNDTIIEFFMKYI 61
         S +  L  +  +QV K     ++      ++    IEI  D TL    WLND II+++    I
1570   SKIKTLPSEQLNQVLKIWSTNSRQLIIENYLIEIYTHDLHTLKDSNWLNDNIIDYYFNLI 1391

62     EKSTPNTVAFNSFFYTNLSERGYQGVRRWMKRKKTQIDKLDKIFTPINLNQSHWALGIID 121
         K+ PN   + +  FYT L +RGYQGV  RW KRKK   +   ++KI TPIN+     HWAL +ID
1390   MKANPNVFGWTTHFYTTLVQRGYQGVARWAKRKKINVFTMEKILTPINIGNMHWALAVID 1211

122    LKKKTIGYVDSLSNGPNAMSFAILTDLQKYVMEESKH--TIGEDFDLI-HLDCPQQPNGY 178
         KKTI Y DSL    N+ +    +   L  Y+ EE+K         +G ++  LI H++   PQQ NG
1210   NIKKTITYYDSLGGTHNSGNPQAVQTLAHYMKEEAKRLGVMGNEYKLIPHMEAPQQKNGS 1031

179    DCGIYVCMNTLYGSADAPLDFDYKDAIRMRRFIAHLILTDAL 220
         DCG++ C   Y SA+ PL +   D    +RR + +  IL + L
1030   DCGVFTCTAARYISANKPLSYSQNDMKIIRRRMVYEILDNRL 905
```

G

```
23       ENTQLMNRDNIEITVRDFKTLAPRRWLNDTIIEFFM----KYIEKST--------PNTVA 70
          EN  L+ + N+ +        K L    RWLND +I F++         +Y E+ T         P
332347   ENRVLIEKFNVPLLYSQIKCLIDTRWLNDEVINFYLSMLQEYNEQHTKNNSLTFIPKIFT 332526

71       FNSFFYTNLSERG---YQGVRRWMKRKKTQIDKLDKIFTPINLNQSHWALGIIDLKKKTI 127
          F++FF+ +L+ +    G   Y V RW KRK+  I     D I  P+++    +HW LG I +K K I
332527   FSTFFFQSLNFNGSYNYSKVSRWTKRKQVDIFSFDLILIPLHVGGNHWTLGSIHMKDKKI 332706

128      GYVDSLSNGPNAMSFAILTDLQKYVMEESKHTIGEDFDL 166
           DSL NG N   F       +++Y+++E K    +D D+
332707   CLYDSL-NGSNKKFFEY---MRRYIVDEMKDKKQKDLDI 332811
```

FIGURE 1 (cont.)

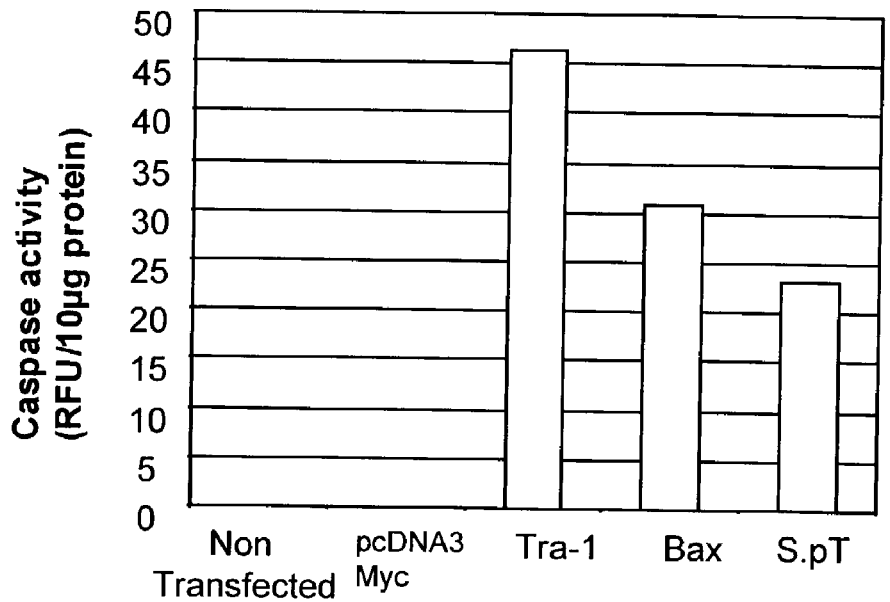
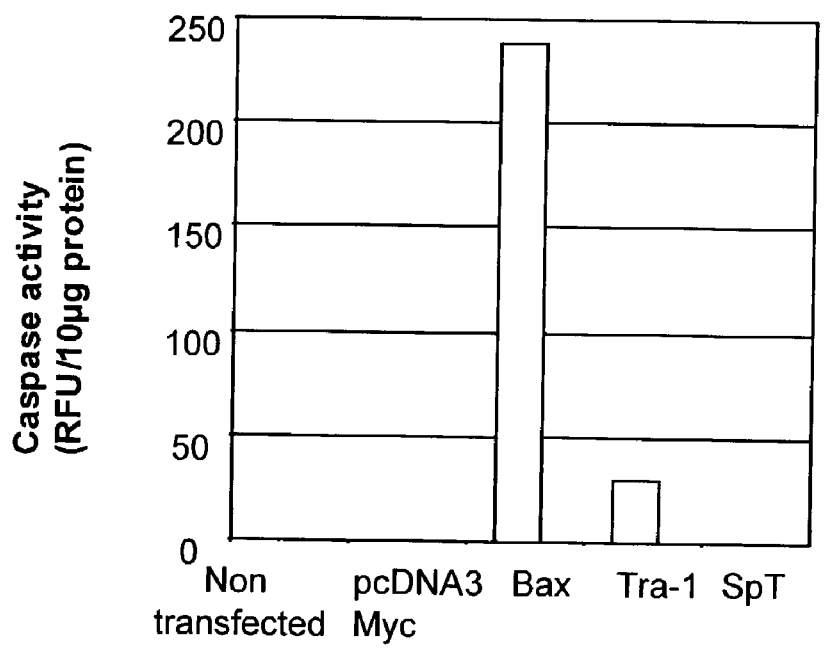
Figure 2

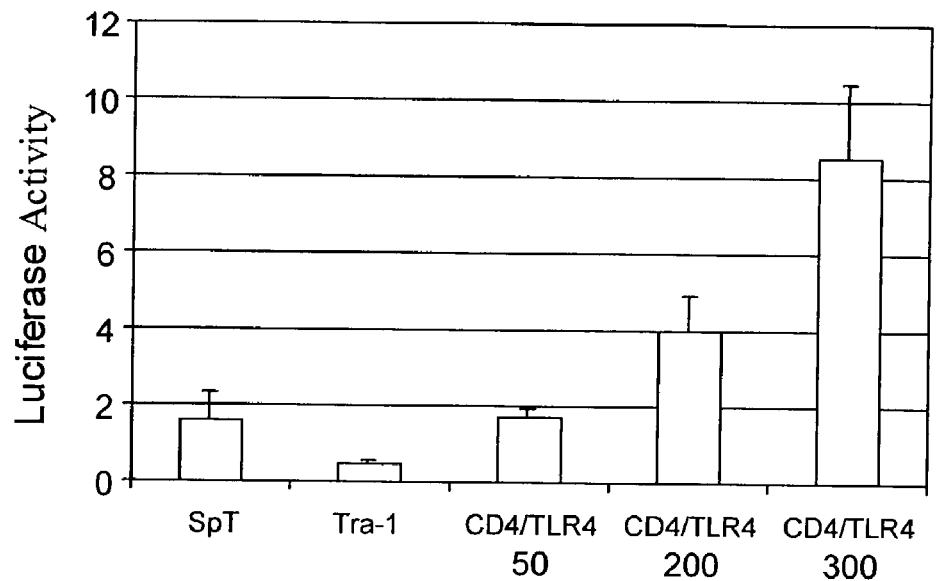
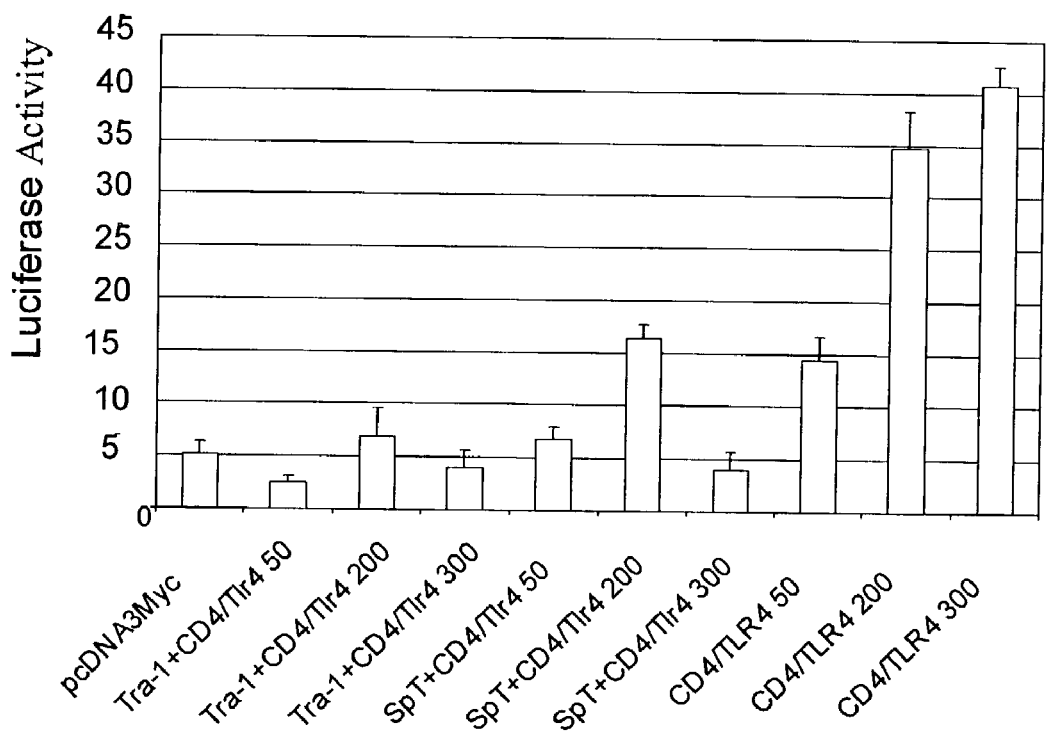
FIGURE 3

US 7,750,134 B2

SEQUENCE LISTING

<160> NUMBER OF SEQ ID NOS: 59

<210> SEQ ID NO 1
<211> LENGTH: 1212
<212> TYPE: DNA
<213> ORGANISM: Eschericia coli
<220> FEATURE:
<221> NAME/KEY: CDS
<222> LOCATION: (1)..(1209)

<400> SEQUENCE: 1

```
atg atg gtt aca gtt gtc agc aat tat tgt caa tta tct caa acg caa     48
Met Met Val Thr Val Val Ser Asn Tyr Cys Gln Leu Ser Gln Thr Gln
1               5                   10                  15 ctc agt cag aca ttt gca gaa aaa ttt act gtg acc gag gaa tta ctg     96
Leu Ser Gln Thr Phe Ala Glu Lys Phe Thr Val Thr Glu Glu Leu Leu
            20                  25                  30 cag tct tta aaa aaa aca gcg tta tcc gga gat gaa gaa agc att gag    144
Gln Ser Leu Lys Lys Thr Ala Leu Ser Gly Asp Glu Glu Ser Ile Glu
        35                  40                  45 tta ctg cat aat att gcg tta ggt tat gat aaa ttt ggg aaa gaa gct    192
Leu Leu His Asn Ile Ala Leu Gly Tyr Asp Lys Phe Gly Lys Glu Ala
    50                  55                  60 gaa gat att ctt tac cat att gtt aga acc cca aca aat gag acc cta    240
Glu Asp Ile Leu Tyr His Ile Val Arg Thr Pro Thr Asn Glu Thr Leu
65                  70                  75                  80 tcg att atc cga ctt atc aaa aat gct tgt tta aaa tta tat aat ctg    288
Ser Ile Ile Arg Leu Ile Lys Asn Ala Cys Leu Lys Leu Tyr Asn Leu
                85                  90                  95 gca cat atc gca acc aac tcc ccc ctc aaa tca cat gat tca gat gat    336
Ala His Ile Ala Thr Asn Ser Pro Leu Lys Ser His Asp Ser Asp Asp
            100                 105                 110 ctc ctg ttc aaa aaa cta ttc tcc cct tcg aaa tta atg aca att atc    384
Leu Leu Phe Lys Lys Leu Phe Ser Pro Ser Lys Leu Met Thr Ile Ile
        115                 120                 125 ggt gat gaa att cct ctt ata tct gaa aaa cag tcg ctt tca aag gtg    432
Gly Asp Glu Ile Pro Leu Ile Ser Glu Lys Gln Ser Leu Ser Lys Val
    130                 135                 140 ctt tta aat gat gag aat aat gaa ctg agt gat ggt aca aac ttc tgg    480
Leu Leu Asn Asp Glu Asn Asn Glu Leu Ser Asp Gly Thr Asn Phe Trp
145                 150                 155                 160 gat aaa aat cgt caa tta acc aca gat gaa ata gct tgc tat ctt cag    528
Asp Lys Asn Arg Gln Leu Thr Thr Asp Glu Ile Ala Cys Tyr Leu Gln
                165                 170                 175 aag atc gcc gct aat gca aaa aat act caa gtc aat tat cct act ggt    576
Lys Ile Ala Ala Asn Ala Lys Asn Thr Gln Val Asn Tyr Pro Thr Gly
            180                 185                 190 ctc tac gtc ccc tac tcc acc aga act cac ctg gaa gac gct ctc aat    624
Leu Tyr Val Pro Tyr Ser Thr Arg Thr His Leu Glu Asp Ala Leu Asn
        195                 200                 205 gaa aat att aag agc gat cca tca tgg ccg aat gaa gtc cag tta ttc    672
Glu Asn Ile Lys Ser Asp Pro Ser Trp Pro Asn Glu Val Gln Leu Phe
    210                 215                 220 ccc ata aat act ggc gga cac tgg ata tta gtt tcg cta cag aaa ata    720
Pro Ile Asn Thr Gly Gly His Trp Ile Leu Val Ser Leu Gln Lys Ile
225                 230                 235                 240 gta aat aaa aaa aat aat aaa cta caa ata aaa tgc gtc ata ttc aac    768
Val Asn Lys Lys Asn Asn Lys Leu Gln Ile Lys Cys Val Ile Phe Asn
                245                 250                 255
```

```
tca ttg cgt gca cta ggc tat gat aaa gaa aat tca ctt aag cgt gtc      816
Ser Leu Arg Ala Leu Gly Tyr Asp Lys Glu Asn Ser Leu Lys Arg Val
        260                 265                 270 att aat agt ttt aat tct gaa ctc atg gga gaa atg tcg aat aat aat      864
Ile Asn Ser Phe Asn Ser Glu Leu Met Gly Glu Met Ser Asn Asn Asn
            275                 280                 285 ata aaa gtt cat tta aat gaa cca gag ata ata ttt tta cat gcc gat      912
Ile Lys Val His Leu Asn Glu Pro Glu Ile Ile Phe Leu His Ala Asp
        290                 295                 300 ctt cag caa tac tta agc caa agt tgc ggt gca ttt gtg tgc atg gca      960
Leu Gln Gln Tyr Leu Ser Gln Ser Cys Gly Ala Phe Val Cys Met Ala
305                 310                 315                 320 gcc cag gaa gtg att gaa caa agg gaa agc aat tct gac agc gcc ccc     1008
Ala Gln Glu Val Ile Glu Gln Arg Glu Ser Asn Ser Asp Ser Ala Pro
                325                 330                 335 tat acg tta tta aaa aac cat gct gac aga ttt aaa aaa tat tca gca     1056
Tyr Thr Leu Leu Lys Asn His Ala Asp Arg Phe Lys Lys Tyr Ser Ala
            340                 345                 350 gaa gag cag tac gaa att gat ttt caa cat cga ctg gca aac aga aat     1104
Glu Glu Gln Tyr Glu Ile Asp Phe Gln His Arg Leu Ala Asn Arg Asn
        355                 360                 365 tgt tat tta gat aaa tat ggc gat gca aat atc aat cat tat tat aga     1152
Cys Tyr Leu Asp Lys Tyr Gly Asp Ala Asn Ile Asn His Tyr Tyr Arg
370                 375                 380 aac tta gaa ata aaa cac tca caa ccc aaa aat aga gca tcc ggc aaa     1200
Asn Leu Glu Ile Lys His Ser Gln Pro Lys Asn Arg Ala Ser Gly Lys
385                 390                 395                 400 aga gtg agt taa                                                     1212
Arg Val Ser <210> SEQ ID NO 2
<211> LENGTH: 403
<212> TYPE: PRT
<213> ORGANISM: Eschericia coli

<400> SEQUENCE: 2

Met Met Val Thr Val Val Ser Asn Tyr Cys Gln Leu Ser Gln Thr Gln
1               5                   10                  15

Leu Ser Gln Thr Phe Ala Glu Lys Phe Thr Val Thr Glu Glu Leu Leu
            20                  25                  30

Gln Ser Leu Lys Lys Thr Ala Leu Ser Gly Asp Glu Glu Ser Ile Glu
        35                  40                  45

Leu Leu His Asn Ile Ala Leu Gly Tyr Asp Lys Phe Gly Lys Glu Ala
    50                  55                  60

Glu Asp Ile Leu Tyr His Ile Val Arg Thr Pro Thr Asn Glu Thr Leu
65                  70                  75                  80

Ser Ile Ile Arg Leu Ile Lys Asn Ala Cys Leu Lys Leu Tyr Asn Leu
                85                  90                  95

Ala His Ile Ala Thr Asn Ser Pro Leu Lys Ser His Asp Ser Asp Asp
            100                 105                 110

Leu Leu Phe Lys Lys Leu Phe Ser Pro Ser Lys Leu Met Thr Ile Ile
        115                 120                 125

Gly Asp Glu Ile Pro Leu Ile Ser Glu Lys Gln Ser Leu Ser Lys Val
    130                 135                 140

Leu Leu Asn Asp Glu Asn Asn Glu Leu Ser Asp Gly Thr Asn Phe Trp
145                 150                 155                 160

Asp Lys Asn Arg Gln Leu Thr Thr Asp Glu Ile Ala Cys Tyr Leu Gln
                165                 170                 175
```

```
Lys Ile Ala Ala Asn Ala Lys Asn Thr Gln Val Asn Tyr Pro Thr Gly
            180                 185                 190

Leu Tyr Val Pro Tyr Ser Thr Arg Thr His Leu Glu Asp Ala Leu Asn
        195                 200                 205

Glu Asn Ile Lys Ser Asp Pro Ser Trp Pro Asn Glu Val Gln Leu Phe
        210                 215                 220

Pro Ile Asn Thr Gly Gly His Trp Ile Leu Val Ser Leu Gln Lys Ile
225                 230                 235                 240

Val Asn Lys Lys Asn Lys Leu Gln Ile Lys Cys Val Ile Phe Asn
            245                 250                 255

Ser Leu Arg Ala Leu Gly Tyr Asp Lys Glu Asn Ser Leu Lys Arg Val
            260                 265                 270

Ile Asn Ser Phe Asn Ser Glu Leu Met Gly Glu Met Ser Asn Asn Asn
            275                 280                 285

Ile Lys Val His Leu Asn Glu Pro Glu Ile Ile Phe Leu His Ala Asp
            290                 295                 300

Leu Gln Gln Tyr Leu Ser Gln Ser Cys Gly Ala Phe Val Cys Met Ala
305                 310                 315                 320

Ala Gln Glu Val Ile Glu Gln Arg Glu Ser Asn Ser Asp Ser Ala Pro
            325                 330                 335

Tyr Thr Leu Leu Lys Asn His Ala Asp Arg Phe Lys Lys Tyr Ser Ala
            340                 345                 350

Glu Glu Gln Tyr Glu Ile Asp Phe Gln His Arg Leu Ala Asn Arg Asn
            355                 360                 365

Cys Tyr Leu Asp Lys Tyr Gly Asp Ala Asn Ile Asn His Tyr Tyr Arg
            370                 375                 380

Asn Leu Glu Ile Lys His Ser Gln Pro Lys Asn Arg Ala Ser Gly Lys
385                 390                 395                 400

Arg Val Ser

<210> SEQ ID NO 3
<211> LENGTH: 1023
<212> TYPE: DNA
<213> ORGANISM: Salmonella paratyphi
<220> FEATURE:
<221> NAME/KEY: CDS
<222> LOCATION: (1)..(1020)

<400> SEQUENCE: 3 atg aat ata tgt gta aat tca ctt tac cga ttg agc aca ccg caa ttt    48
Met Asn Ile Cys Val Asn Ser Leu Tyr Arg Leu Ser Thr Pro Gln Phe
1               5                   10                  15 cac agt tta tat tca gaa gag gtg agc gat gag gcg ctt gcg ttg ttg    96
His Ser Leu Tyr Ser Glu Glu Val Ser Asp Glu Ala Leu Ala Leu Leu
            20                  25                  30 ttt agc gcc gta gag aac ggt gat cag aat tgt att gat ctg tta tgc   144
Phe Ser Ala Val Glu Asn Gly Asp Gln Asn Cys Ile Asp Leu Leu Cys
        35                  40                  45 aat ctt gcg tta cgc aat gat aac ctg gga cat aga gtt gag aaa ttt   192
Asn Leu Ala Leu Arg Asn Asp Asn Leu Gly His Arg Val Glu Lys Phe
    50                  55                  60 ctt ttt gat ctc ttt agc gga aaa aga tcg gga tca cca gac ata gac   240
Leu Phe Asp Leu Phe Ser Gly Lys Arg Ser Gly Ser Pro Asp Ile Asp
65                  70                  75                  80 aaa aaa atc aat cag gct tgc ctt gta tta cat caa atc gcc aat aac   288
Lys Lys Ile Asn Gln Ala Cys Leu Val Leu His Gln Ile Ala Asn Asn
                85                  90                  95
```

| | | |
|---|---|---|
| gat ata aca aaa gat aat act gag tgg aaa aag cta cat gcc cct tcc<br>Asp Ile Thr Lys Asp Asn Thr Glu Trp Lys Lys Leu His Ala Pro Ser<br>100 105 110 | | 336 |
| aga tta ctt tat atg gcc ggt tcc gcg aca acc gac ctt tct aaa aaa<br>Arg Leu Leu Tyr Met Ala Gly Ser Ala Thr Thr Asp Leu Ser Lys Lys<br>115 120 125 | | 384 |
| ata gga ata gca cat aaa att atg ggc gac cag ttc gct cag aca gat<br>Ile Gly Ile Ala His Lys Ile Met Gly Asp Gln Phe Ala Gln Thr Asp<br>130 135 140 | | 432 |
| caa gaa cag gta gga gtt gaa aat ctt tgg tgt agt gcg cga atg ttg<br>Gln Glu Gln Val Gly Val Glu Asn Leu Trp Cys Ser Ala Arg Met Leu<br>145 150 155 160 | | 480 |
| tcg tca gat gag cta gca gcc gca acg cta ggt ctg gtt caa gaa tca<br>Ser Ser Asp Glu Leu Ala Ala Ala Thr Leu Gly Leu Val Gln Glu Ser<br>165 170 175 | | 528 |
| cct ctt ctc tcg gta aac tat cct att ggg ctt att cat cct acc acc<br>Pro Leu Leu Ser Val Asn Tyr Pro Ile Gly Leu Ile His Pro Thr Thr<br>180 185 190 | | 576 |
| aaa gaa aat ata tta cgc act cag cta ctt gaa aag atg gct caa tca<br>Lys Glu Asn Ile Leu Arg Thr Gln Leu Leu Glu Lys Met Ala Gln Ser<br>195 200 205 | | 624 |
| gga tta tct gaa aat gaa gtc ttt ctg ata aat aca gga gat cac tgg<br>Gly Leu Ser Glu Asn Glu Val Phe Leu Ile Asn Thr Gly Asp His Trp<br>210 215 220 | | 672 |
| ctt atc tgt tta ttt tat aaa ctt gca gaa aaa ata aaa tgc ctt ata<br>Leu Ile Cys Leu Phe Tyr Lys Leu Ala Glu Lys Ile Lys Cys Leu Ile<br>225 230 235 240 | | 720 |
| ttt aat act tat cat gat tta aat gaa aat act aag caa gag att ata<br>Phe Asn Thr Tyr His Asp Leu Asn Glu Asn Thr Lys Gln Glu Ile Ile<br>245 250 255 | | 768 |
| gaa gca gca aaa att aca ggc ata tca gaa aac gaa gat att gat ttt<br>Glu Ala Ala Lys Ile Thr Gly Ile Ser Glu Asn Glu Asp Ile Asp Phe<br>260 265 270 | | 816 |
| att gaa acc aat tta caa aat aat gta ccc aac ggc tgt ggt cta ttt<br>Ile Glu Thr Asn Leu Gln Asn Asn Val Pro Asn Gly Cys Gly Leu Phe<br>275 280 285 | | 864 |
| tgt tac cat aca att caa ctc tta tcg aat gca gga caa aac gat cct<br>Cys Tyr His Thr Ile Gln Leu Leu Ser Asn Ala Gly Gln Asn Asp Pro<br>290 295 300 | | 912 |
| gct acc aca cta cga gaa ttt gcg gaa aat ttc tta acg ctt tca gta<br>Ala Thr Thr Leu Arg Glu Phe Ala Glu Asn Phe Leu Thr Leu Ser Val<br>305 310 315 320 | | 960 |
| gag gaa caa aca cta ttt aac acc caa acc cgg cga caa ata tat gaa<br>Glu Glu Gln Thr Leu Phe Asn Thr Gln Thr Arg Arg Gln Ile Tyr Glu<br>325 330 335 | | 1008 |
| tac agt ctc cag taa<br>Tyr Ser Leu Gln<br>340 | | 1023 |

<210> SEQ ID NO 4
<211> LENGTH: 340
<212> TYPE: PRT
<213> ORGANISM: Salmonella paratyphi

<400> SEQUENCE: 4

Met Asn Ile Cys Val Asn Ser Leu Tyr Arg Leu Ser Thr Pro Gln Phe
1               5                   10                  15

His Ser Leu Tyr Ser Glu Glu Val Ser Asp Glu Ala Leu Ala Leu Leu
            20                  25                  30

```
Phe Ser Ala Val Glu Asn Gly Asp Gln Asn Cys Ile Asp Leu Leu Cys
         35                  40                  45

Asn Leu Ala Leu Arg Asn Asp Asn Leu Gly His Arg Val Glu Lys Phe
 50                  55                  60

Leu Phe Asp Leu Phe Ser Gly Lys Arg Ser Gly Ser Pro Asp Ile Asp
65                  70                  75                  80

Lys Lys Ile Asn Gln Ala Cys Leu Val Leu His Gln Ile Ala Asn Asn
             85                  90                  95

Asp Ile Thr Lys Asp Asn Thr Glu Trp Lys Lys Leu His Ala Pro Ser
            100                 105                 110

Arg Leu Leu Tyr Met Ala Gly Ser Ala Thr Thr Asp Leu Ser Lys Lys
            115                 120                 125

Ile Gly Ile Ala His Lys Ile Met Gly Asp Gln Phe Ala Gln Thr Asp
            130                 135                 140

Gln Glu Gln Val Gly Val Glu Asn Leu Trp Cys Ser Ala Arg Met Leu
145                 150                 155                 160

Ser Ser Asp Glu Leu Ala Ala Thr Leu Gly Leu Val Gln Glu Ser
                165                 170                 175

Pro Leu Leu Ser Val Asn Tyr Pro Ile Gly Leu Ile His Pro Thr Thr
                180                 185                 190

Lys Glu Asn Ile Leu Arg Thr Gln Leu Leu Glu Lys Met Ala Gln Ser
            195                 200                 205

Gly Leu Ser Glu Asn Glu Val Phe Leu Ile Asn Thr Gly Asp His Trp
            210                 215                 220

Leu Ile Cys Leu Phe Tyr Lys Leu Ala Glu Lys Ile Lys Cys Leu Ile
225                 230                 235                 240

Phe Asn Thr Tyr His Asp Leu Asn Glu Asn Thr Lys Gln Glu Ile Ile
                245                 250                 255

Glu Ala Ala Lys Ile Thr Gly Ile Ser Glu Asn Glu Asp Ile Asp Phe
                260                 265                 270

Ile Glu Thr Asn Leu Gln Asn Asn Val Pro Asn Gly Cys Gly Leu Phe
            275                 280                 285

Cys Tyr His Thr Ile Gln Leu Leu Ser Asn Ala Gly Asn Asp Pro
            290                 295                 300

Ala Thr Thr Leu Arg Glu Phe Ala Glu Asn Phe Leu Thr Leu Ser Val
305                 310                 315                 320

Glu Glu Gln Thr Leu Phe Asn Thr Gln Thr Arg Arg Gln Ile Tyr Glu
                325                 330                 335

Tyr Ser Leu Gln
        340

<210> SEQ ID NO 5
<211> LENGTH: 954
<212> TYPE: DNA
<213> ORGANISM: Salmonella enteriditis
<220> FEATURE:
<221> NAME/KEY: CDS
<222> LOCATION: (1)..(951)

<400> SEQUENCE: 5 gtg agc gat gag gcg ctt gcg ttg ttg att ggc gaa gta gag aac ggt    48
Val Ser Asp Glu Ala Leu Ala Leu Leu Ile Gly Glu Val Glu Asn Gly
 1               5                  10                  15 aat cag aat tgt att gat ctg tta tgc aat ctt gcg tta cgc aac gat    96
Asn Gln Asn Cys Ile Asp Leu Leu Cys Asn Leu Ala Leu Arg Asn Asp
             20                  25                  30
```

```
gac ctg gga cat aaa gtt gag aaa tta ctt ttt gat ctc ttt agc gga      144
Asp Leu Gly His Lys Val Glu Lys Leu Leu Phe Asp Leu Phe Ser Gly
         35                  40                  45 aaa aga tcg gga tca cca gat ata gac aaa aaa atc aat cag gct tgc      192
Lys Arg Ser Gly Ser Pro Asp Ile Asp Lys Lys Ile Asn Gln Ala Cys
 50                  55                  60 ctt gta tta cat caa atc gcc aat aac gat ata aca aaa aat aat act      240
Leu Val Leu His Gln Ile Ala Asn Asn Asp Ile Thr Lys Asn Asn Thr
 65                  70                  75                  80 gag tgg aaa aag cta cat gcc cct tcc aga tta ctt tat atg gcc ggt      288
Glu Trp Lys Lys Leu His Ala Pro Ser Arg Leu Leu Tyr Met Ala Gly
                 85                  90                  95 tca gcg aca acc gac ctt tct aaa aaa ata gga ata gca cat aaa att      336
Ser Ala Thr Thr Asp Leu Ser Lys Lys Ile Gly Ile Ala His Lys Ile
            100                 105                 110 atg ggc gac cag ttc gct cag aca gat caa gaa cag gta gga gtt gaa      384
Met Gly Asp Gln Phe Ala Gln Thr Asp Gln Glu Gln Val Gly Val Glu
                115                 120                 125 aat ctt tgg tgt ggt gcg cga atg ttg tcg tca gat gag ctg gca gct      432
Asn Leu Trp Cys Gly Ala Arg Met Leu Ser Ser Asp Glu Leu Ala Ala
130                 135                 140 gca acg caa ggt ctg gtt caa gaa tca cct ctt ctc tcg gta aac tat      480
Ala Thr Gln Gly Leu Val Gln Glu Ser Pro Leu Leu Ser Val Asn Tyr
145                 150                 155                 160 cct att ggg ctg att cat cct acc acc aaa gaa aat ata tta agc act      528
Pro Ile Gly Leu Ile His Pro Thr Thr Lys Glu Asn Ile Leu Ser Thr
                165                 170                 175 cag cta ctt gaa aag att gct caa tca gga tta tct cac aat gaa gtc      576
Gln Leu Leu Glu Lys Ile Ala Gln Ser Gly Leu Ser His Asn Glu Val
            180                 185                 190 ttc ctg gta aat aca gga gat cac tgg ctt ctc tgt tta ttt tat aaa      624
Phe Leu Val Asn Thr Gly Asp His Trp Leu Leu Cys Leu Phe Tyr Lys
                195                 200                 205 ctt gca gaa aaa ata aaa tgc ctt ata ttt aat act tat tat gat tta      672
Leu Ala Glu Lys Ile Lys Cys Leu Ile Phe Asn Thr Tyr Tyr Asp Leu
210                 215                 220 aat gaa aat act aag caa gag att ata gaa gca gca aaa att gca ggt      720
Asn Glu Asn Thr Lys Gln Glu Ile Ile Glu Ala Ala Lys Ile Ala Gly
225                 230                 235                 240 ata tca gaa aac gaa aat att gat ttt att gaa act aat tta caa aat      768
Ile Ser Glu Asn Glu Asn Ile Asp Phe Ile Glu Thr Asn Leu Gln Asn
                245                 250                 255 aat gta ccc aac ggc tgt ggt cta ttt tgt tac cat gca att caa ctc      816
Asn Val Pro Asn Gly Cys Gly Leu Phe Cys Tyr His Ala Ile Gln Leu
            260                 265                 270 tta tcg aat gca gga caa aac gat cct gct acc aca cta cga gag ttt      864
Leu Ser Asn Ala Gly Gln Asn Asp Pro Ala Thr Thr Leu Arg Glu Phe
        275                 280                 285 gcg gaa aat ttc tta acg ctt tca gta gag gaa caa aca cta ttt aac      912
Ala Glu Asn Phe Leu Thr Leu Ser Val Glu Glu Gln Thr Leu Phe Asn
                290                 295                 300 acc caa acc cgg cga caa ata tat gaa tac agt ctc cag taa              954
Thr Gln Thr Arg Arg Gln Ile Tyr Glu Tyr Ser Leu Gln
305                 310                 315

<210> SEQ ID NO 6
<211> LENGTH: 317
<212> TYPE: PRT
<213> ORGANISM: Salmonella enteriditis

<400> SEQUENCE: 6
```

```
Val Ser Asp Glu Ala Leu Ala Leu Leu Ile Gly Glu Val Glu Asn Gly
1               5                   10                  15

Asn Gln Asn Cys Ile Asp Leu Leu Cys Asn Leu Ala Leu Arg Asn Asp
            20                  25                  30

Asp Leu Gly His Lys Val Glu Lys Leu Leu Phe Asp Leu Phe Ser Gly
        35                  40                  45

Lys Arg Ser Gly Ser Pro Asp Ile Asp Lys Lys Ile Asn Gln Ala Cys
    50                  55                  60

Leu Val Leu His Gln Ile Ala Asn Asn Asp Ile Thr Lys Asn Asn Thr
65                  70                  75                  80

Glu Trp Lys Lys Leu His Ala Pro Ser Arg Leu Leu Tyr Met Ala Gly
                85                  90                  95

Ser Ala Thr Thr Asp Leu Ser Lys Lys Ile Gly Ile Ala His Lys Ile
                100                 105                 110

Met Gly Asp Gln Phe Ala Gln Thr Asp Gln Glu Gln Val Gly Val Glu
            115                 120                 125

Asn Leu Trp Cys Gly Ala Arg Met Leu Ser Ser Asp Glu Leu Ala Ala
130                 135                 140

Ala Thr Gln Gly Leu Val Gln Glu Ser Pro Leu Leu Ser Val Asn Tyr
145                 150                 155                 160

Pro Ile Gly Leu Ile His Pro Thr Thr Lys Glu Asn Ile Leu Ser Thr
                165                 170                 175

Gln Leu Leu Glu Lys Ile Ala Gln Ser Gly Leu Ser His Asn Glu Val
            180                 185                 190

Phe Leu Val Asn Thr Gly Asp His Trp Leu Leu Cys Leu Phe Tyr Lys
        195                 200                 205

Leu Ala Glu Lys Ile Lys Cys Leu Ile Phe Asn Thr Tyr Tyr Asp Leu
    210                 215                 220

Asn Glu Asn Thr Lys Gln Glu Ile Ile Glu Ala Ala Lys Ile Ala Gly
225                 230                 235                 240

Ile Ser Glu Asn Glu Asn Ile Asp Phe Ile Glu Thr Asn Leu Gln Asn
                245                 250                 255

Asn Val Pro Asn Gly Cys Gly Leu Phe Cys Tyr His Ala Ile Gln Leu
            260                 265                 270

Leu Ser Asn Ala Gly Gln Asn Asp Pro Ala Thr Thr Leu Arg Glu Phe
        275                 280                 285

Ala Glu Asn Phe Leu Thr Leu Ser Val Glu Gln Thr Leu Phe Asn
    290                 295                 300

Thr Gln Thr Arg Arg Gln Ile Tyr Glu Tyr Ser Leu Gln
305                 310                 315

<210> SEQ ID NO 7

<400> SEQUENCE: 7

000

<210> SEQ ID NO 8
<211> LENGTH: 327
<212> TYPE: PRT
<213> ORGANISM: Salmonella typhimurium

<400> SEQUENCE: 8

Val Asn Ser Leu Tyr Arg Leu Ser Ile Pro Gln Phe His Ser Leu Tyr
1               5                   10                  15
```

```
Thr Glu Glu Val Ser Asp Glu Ala Leu Thr Leu Leu Phe Ser Ala Val
         20                  25                  30

Glu Asn Gly Asp Gln Asn Cys Ile Asp Leu Leu Cys Asn Leu Ala Leu
         35                  40                  45

Arg Asn Asp Asp Leu Gly His Arg Val Glu Lys Phe Leu Phe Asp Leu
 50                  55                  60

Phe Ser Gly Lys Arg Thr Gly Ser Ser Asp Ile Asp Lys Lys Ile Asn
 65                  70                  75                  80

Gln Ala Cys Leu Val Leu His Gln Ile Ala Asn Asn Asp Ile Thr Lys
                 85                  90                  95

Asp Asn Thr Glu Trp Lys Lys Leu His Ala Pro Ser Arg Leu Leu Tyr
                100                 105                 110

Met Ala Gly Ser Ala Thr Thr Asp Leu Ser Lys Lys Ile Gly Ile Ala
            115                 120                 125

His Lys Ile Met Gly Asp Gln Phe Ala Gln Thr Asp Gln Glu Gln Val
        130                 135                 140

Gly Val Glu Asn Leu Trp Cys Gly Ala Arg Met Leu Ser Ser Asp Glu
145                 150                 155                 160

Leu Ala Ala Ala Thr Gln Gly Leu Val Gln Glu Ser Pro Leu Leu Ser
                165                 170                 175

Val Asn Tyr Pro Ile Gly Leu Ile His Pro Thr Thr Lys Glu Asn Ile
            180                 185                 190

Leu Ser Thr Gln Leu Leu Glu Lys Ile Ala Gln Ser Gly Leu Ser His
        195                 200                 205

Asn Glu Val Phe Leu Val Asn Thr Gly Asp His Trp Leu Leu Cys Leu
210                 215                 220

Phe Tyr Lys Leu Ala Glu Lys Ile Lys Cys Leu Ile Phe Asn Thr Tyr
225                 230                 235                 240

Tyr Asp Leu Asn Glu Asn Thr Lys Gln Glu Ile Ile Glu Ala Ala Lys
                245                 250                 255

Ile Ala Gly Ile Ser Glu Ser Asp Glu Val Asn Phe Ile Glu Met Asn
            260                 265                 270

Leu Gln Asn Asn Val Pro Asn Gly Cys Gly Leu Phe Cys Tyr His Thr
        275                 280                 285

Ile Gln Leu Leu Ser Asn Ala Gly Gln Asn Asp Pro Ala Thr Thr Leu
290                 295                 300

Arg Glu Phe Ala Glu Asn Phe Leu Thr Leu Ser Val Glu Glu Gln Ala
305                 310                 315                 320

Leu Phe Asn Thr Gln Thr Arg
                325
```

<210> SEQ ID NO 9
<211> LENGTH: 1023
<212> TYPE: DNA
<213> ORGANISM: Salmonella typhi
<220> FEATURE:
<221> NAME/KEY: CDS
<222> LOCATION: (1)..(1020)

<400> SEQUENCE: 9

```
atg aat ata tgt gta aat tca ctt tac cga ttg agc aca ccg caa ttt    48
Met Asn Ile Cys Val Asn Ser Leu Tyr Arg Leu Ser Thr Pro Gln Phe
1               5                   10                  15 cac agt tta tat tca gaa gag gtg agc gat gag gcg ctt gcg ttg ttg    96
His Ser Leu Tyr Ser Glu Glu Val Ser Asp Glu Ala Leu Ala Leu Leu
            20                  25                  30
```

```
ttt agc gcc gta gag aac ggt gat cag aat tgt att gat ctg tta tgc    144
Phe Ser Ala Val Glu Asn Gly Asp Gln Asn Cys Ile Asp Leu Leu Cys
        35                  40                  45 aat ctt gcg tta cgc aat gat aac ctg gga cat aga gtt gag aaa ttt    192
Asn Leu Ala Leu Arg Asn Asp Asn Leu Gly His Arg Val Glu Lys Phe
 50                  55                  60 ctt ttt gat ctc ttt agc gga aaa aga tcg gga tca cca gac ata gac    240
Leu Phe Asp Leu Phe Ser Gly Lys Arg Ser Gly Ser Pro Asp Ile Asp
65                  70                  75                  80 aaa aaa atc aat cag gct tgc ctt gta tta cat caa atc gcc aat aac    288
Lys Lys Ile Asn Gln Ala Cys Leu Val Leu His Gln Ile Ala Asn Asn
                85                  90                  95 gat ata aca aaa gat aat act gag tgg aaa aag cta cat gcc cct tcc    336
Asp Ile Thr Lys Asp Asn Thr Glu Trp Lys Lys Leu His Ala Pro Ser
            100                 105                 110 aga tta ctt tat atg gcc ggt tcc gcg aca acc gac ctt tct aaa aaa    384
Arg Leu Leu Tyr Met Ala Gly Ser Ala Thr Thr Asp Leu Ser Lys Lys
        115                 120                 125 ata gga ata gca cat aaa att atg ggc gac cag ttc gct cag aca gat    432
Ile Gly Ile Ala His Lys Ile Met Gly Asp Gln Phe Ala Gln Thr Asp
130                 135                 140 caa gaa cag gta gga gtt gaa aat ctt tgg tgt agt gcg cga atg ttg    480
Gln Glu Gln Val Gly Val Glu Asn Leu Trp Cys Ser Ala Arg Met Leu
145                 150                 155                 160 tcg tca gat gag cta gca gcc gca acg cta ggt ctg gtt caa gaa tca    528
Ser Ser Asp Glu Leu Ala Ala Ala Thr Leu Gly Leu Val Gln Glu Ser
                165                 170                 175 cct ctt ctc tcg gta aac tat cct att ggg ctt att cat cct acc acc    576
Pro Leu Leu Ser Val Asn Tyr Pro Ile Gly Leu Ile His Pro Thr Thr
            180                 185                 190 aaa gaa aat ata tta cgc act cag cta ctt gaa aag atg gct caa tca    624
Lys Glu Asn Ile Leu Arg Thr Gln Leu Leu Glu Lys Met Ala Gln Ser
        195                 200                 205 gga tta tct gaa aat gaa gtc ttt ctg ata aat aca gga gat cac tgg    672
Gly Leu Ser Glu Asn Glu Val Phe Leu Ile Asn Thr Gly Asp His Trp
210                 215                 220 ctt atc tgt tta ttt tat aaa ctt gca gaa aaa ata aaa tgc ctt ata    720
Leu Ile Cys Leu Phe Tyr Lys Leu Ala Glu Lys Ile Lys Cys Leu Ile
225                 230                 235                 240 ttt aat act tat cat gat tta aat gaa aat act aag caa gag att ata    768
Phe Asn Thr Tyr His Asp Leu Asn Glu Asn Thr Lys Gln Glu Ile Ile
                245                 250                 255 gaa gca gca aaa att aca ggc ata tca gaa aac gaa gat att gat ttt    816
Glu Ala Ala Lys Ile Thr Gly Ile Ser Glu Asn Glu Asp Ile Asp Phe
            260                 265                 270 att gaa acc aat tta caa aat aat gta ccc aac ggc tgt ggt cta ttt    864
Ile Glu Thr Asn Leu Gln Asn Asn Val Pro Asn Gly Cys Gly Leu Phe
        275                 280                 285 tgt tac cat aca att caa ctc tta tcg aat gca gga caa aac gat cct    912
Cys Tyr His Thr Ile Gln Leu Leu Ser Asn Ala Gly Gln Asn Asp Pro
290                 295                 300 gct acc aca cta cga gaa ttt gcg gaa aat ttc tta acg ctt tca gta    960
Ala Thr Thr Leu Arg Glu Phe Ala Glu Asn Phe Leu Thr Leu Ser Val
305                 310                 315                 320 gag gaa caa aca cta ttt aac acc caa acc cgg cga caa ata tat gaa    1008
Glu Glu Gln Thr Leu Phe Asn Thr Gln Thr Arg Arg Gln Ile Tyr Glu
                325                 330                 335 tac agt ctc cag taa                                                1023
Tyr Ser Leu Gln
            340
```

<210> SEQ ID NO 10
<211> LENGTH: 340
<212> TYPE: PRT
<213> ORGANISM: Salmonella typhi

<400> SEQUENCE: 10

Met Asn Ile Cys Val Asn Ser Leu Tyr Arg Leu Ser Thr Pro Gln Phe
1               5                   10                  15

His Ser Leu Tyr Ser Glu Glu Val Ser Asp Glu Ala Leu Ala Leu Leu
            20                  25                  30

Phe Ser Ala Val Glu Asn Gly Asp Gln Asn Cys Ile Asp Leu Leu Cys
        35                  40                  45

Asn Leu Ala Leu Arg Asn Asp Asn Leu Gly His Arg Val Glu Lys Phe
50                  55                  60

Leu Phe Asp Leu Phe Ser Gly Lys Arg Ser Gly Ser Pro Asp Ile Asp
65                  70                  75                  80

Lys Lys Ile Asn Gln Ala Cys Leu Val Leu His Gln Ile Ala Asn Asn
                85                  90                  95

Asp Ile Thr Lys Asp Asn Thr Glu Trp Lys Lys Leu His Ala Pro Ser
            100                 105                 110

Arg Leu Leu Tyr Met Ala Gly Ser Ala Thr Thr Asp Leu Ser Lys Lys
        115                 120                 125

Ile Gly Ile Ala His Lys Ile Met Gly Asp Gln Phe Ala Gln Thr Asp
130                 135                 140

Gln Glu Gln Val Gly Val Glu Asn Leu Trp Cys Ser Ala Arg Met Leu
145                 150                 155                 160

Ser Ser Asp Glu Leu Ala Ala Ala Thr Leu Gly Leu Val Gln Glu Ser
                165                 170                 175

Pro Leu Leu Ser Val Asn Tyr Pro Ile Gly Leu Ile His Pro Thr Thr
            180                 185                 190

Lys Glu Asn Ile Leu Arg Thr Gln Leu Leu Glu Lys Met Ala Gln Ser
        195                 200                 205

Gly Leu Ser Glu Asn Glu Val Phe Leu Ile Asn Thr Gly Asp His Trp
210                 215                 220

Leu Ile Cys Leu Phe Tyr Lys Leu Ala Glu Lys Ile Lys Cys Leu Ile
225                 230                 235                 240

Phe Asn Thr Tyr His Asp Leu Asn Glu Asn Thr Lys Gln Glu Ile Ile
                245                 250                 255

Glu Ala Ala Lys Ile Thr Gly Ile Ser Glu Asn Glu Asp Ile Asp Phe
            260                 265                 270

Ile Glu Thr Asn Leu Gln Asn Asn Val Pro Asn Gly Cys Gly Leu Phe
        275                 280                 285

Cys Tyr His Thr Ile Gln Leu Leu Ser Asn Ala Gly Gln Asn Asp Pro
290                 295                 300

Ala Thr Thr Leu Arg Glu Phe Ala Glu Asn Phe Leu Thr Leu Ser Val
305                 310                 315                 320

Glu Glu Gln Thr Leu Phe Asn Thr Gln Thr Arg Arg Gln Ile Tyr Glu
                325                 330                 335

Tyr Ser Leu Gln
            340

<210> SEQ ID NO 11
<211> LENGTH: 2196
<212> TYPE: DNA

<213> ORGANISM: Pseudomonas syringae
<220> FEATURE:
<221> NAME/KEY: CDS
<222> LOCATION: (1)..(2193)

<400> SEQUENCE: 11

```
atg tgg aat ttt aat aac tgg agc aaa ggc ttg gac gct tat cag aga      48
Met Trp Asn Phe Asn Asn Trp Ser Lys Gly Leu Asp Ala Tyr Gln Arg
1               5                   10                  15 ctc cag gaa acg caa agt aaa ctt cat gag ttt ctt tct tct gat aca      96
Leu Gln Glu Thr Gln Ser Lys Leu His Glu Phe Leu Ser Ser Asp Thr
            20                  25                  30 aca tcc tca gtc caa ccc gat ggg ggg ggc gcg cac gac ctg ccg caa     144
Thr Ser Ser Val Gln Pro Asp Gly Gly Gly Ala His Asp Leu Pro Gln
        35                  40                  45 aga cag cga tat tct att cag caa gct gag tct cag ggc agg cgg ctc     192
Arg Gln Arg Tyr Ser Ile Gln Gln Ala Glu Ser Gln Gly Arg Arg Leu
    50                  55                  60 gta gat caa gca gaa cta caa acg cag gtt gag cgc cgc ttt tca aaa     240
Val Asp Gln Ala Glu Leu Gln Thr Gln Val Glu Arg Arg Phe Ser Lys
65                  70                  75                  80 aag tct gag aca aga tat gta acg gag gtt caa ttt gtt cca gat cac     288
Lys Ser Glu Thr Arg Tyr Val Thr Glu Val Gln Phe Val Pro Asp His
                85                  90                  95 ctt gag gat act gag tat cga tac agc tct aga aaa gtc ccc tat tgt     336
Leu Glu Asp Thr Glu Tyr Arg Tyr Ser Ser Arg Lys Val Pro Tyr Cys
            100                 105                 110 gag gat ata gca ctc att gaa aga ttt tgc gag ggt gct ctg cta ggt     384
Glu Asp Ile Ala Leu Ile Glu Arg Phe Cys Glu Gly Ala Leu Leu Gly
        115                 120                 125 ggt agc aac tct aac acc gtg gac ttt tat aaa aat cag ttg atc tct     432
Gly Ser Asn Ser Asn Thr Val Asp Phe Tyr Lys Asn Gln Leu Ile Ser
    130                 135                 140 att agt gac tat ctt cag cga cag cac atg cca gcg att aac gca cgt     480
Ile Ser Asp Tyr Leu Gln Arg Gln His Met Pro Ala Ile Asn Ala Arg
145                 150                 155                 160 tta ttc tct gat agt ctt gaa agc gat tta aaa cag tat gcg ttt caa     528
Leu Phe Ser Asp Ser Leu Glu Ser Asp Leu Lys Gln Tyr Ala Phe Gln
                165                 170                 175 aac aat cgc agt gat acg ctg gca att ata ggt cac tta cga cgt att     576
Asn Asn Arg Ser Asp Thr Leu Ala Ile Ile Gly His Leu Arg Arg Ile
            180                 185                 190 gaa tct aac aaa cac ggg gtc agt gct att ctg cct ttc aaa aca aaa     624
Glu Ser Asn Lys His Gly Val Ser Ala Ile Leu Pro Phe Lys Thr Lys
        195                 200                 205 agt tca gat tta gac gaa tgg tta atc gat caa gtg ttt tcc gac gaa     672
Ser Ser Asp Leu Asp Glu Trp Leu Ile Asp Gln Val Phe Ser Asp Glu
    210                 215                 220 aac cag act act tcc tca tat aga tca act ttg cgc gcg ctc agt cat     720
Asn Gln Thr Thr Ser Ser Tyr Arg Ser Thr Leu Arg Ala Leu Ser His
225                 230                 235                 240 tgg ctc gca gca caa gaa aag ccg ggg ctg tgt gat ccg gac tat ctc     768
Trp Leu Ala Ala Gln Glu Lys Pro Gly Leu Cys Asp Pro Asp Tyr Leu
                245                 250                 255 cat tcc cat gaa ttg acg gaa gat gtg ctg aag ttc agc tgt ttg cca     816
His Ser His Glu Leu Thr Glu Asp Val Leu Lys Phe Ser Cys Leu Pro
            260                 265                 270 ggc cgt cac caa tgt agc gcg gcg ttg caa cac atg cga aac tat gac     864
Gly Arg His Gln Cys Ser Ala Ala Leu Gln His Met Arg Asn Tyr Asp
        275                 280                 285
```

-continued

| | | |
|---|---|---|
| ctt ggt agt aaa gtt cgc cta aag aag caa cgt gat acc cgt aat atc<br>Leu Gly Ser Lys Val Arg Leu Lys Lys Gln Arg Asp Thr Arg Asn Ile<br>290                        295                      300 | 912 | |
| cca gac gag gac caa acg tta atc tcg cac tac caa aaa att gct aac<br>Pro Asp Glu Asp Gln Thr Leu Ile Ser His Tyr Gln Lys Ile Ala Asn<br>305                      310                      315                  320 | 960 | |
| gat gcc ttg gta ata aaa aat agt aaa gcc gga aaa aaa acg aat cgt<br>Asp Ala Leu Val Ile Lys Asn Ser Lys Ala Gly Lys Lys Thr Asn Arg<br>                    325                      330                      335 | 1008 | |
| gat cct cat gga aga acg agc gtt gac aag tac gcg tct gta cta cgc<br>Asp Pro His Gly Arg Thr Ser Val Asp Lys Tyr Ala Ser Val Leu Arg<br>                    340                      345                      350 | 1056 | |
| tca ttc agc gcg tgg ctt aag gag gag gga aaa gga agc ttg tca act<br>Ser Phe Ser Ala Trp Leu Lys Glu Glu Gly Lys Gly Ser Leu Ser Thr<br>                355                      360                      365 | 1104 | |
| ctt ctt cac gat cca gag ttg gat acg tat agg gat tta tgg acg cac<br>Leu Leu His Asp Pro Glu Leu Asp Thr Tyr Arg Asp Leu Trp Thr His<br>370                        375                      380 | 1152 | |
| aac aaa agc tct tct aat gcc aaa acg gtt gta acc ctg cta ata aaa<br>Asn Lys Ser Ser Ser Asn Ala Lys Thr Val Val Thr Leu Leu Ile Lys<br>385                        390                      395                  400 | 1200 | |
| ttg cgt gaa ata ttt cca ccc ttc tca gta gaa gcg gta caa gaa cct<br>Leu Arg Glu Ile Phe Pro Pro Phe Ser Val Glu Ala Val Gln Glu Pro<br>                          405                      410                      415 | 1248 | |
| agt cac tcc tct ttt acg ttg cca aat tca gag tgg tca ggt tgg ggc<br>Ser His Ser Ser Phe Thr Leu Pro Asn Ser Glu Trp Ser Gly Trp Gly<br>                    420                      425                      430 | 1296 | |
| tgg aat cca gat acg ccg caa tac ccc cct caa agt cca gct tcg acc<br>Trp Asn Pro Asp Thr Pro Gln Tyr Pro Pro Gln Ser Pro Ala Ser Thr<br>                435                      440                      445 | 1344 | |
| ttc aac gga ctc tcc tcc ctg agt gat tac ggc cgc gaa ttc gac ctc<br>Phe Asn Gly Leu Ser Ser Leu Ser Asp Tyr Gly Arg Glu Phe Asp Leu<br>450                        455                      460 | 1392 | |
| aat acg ccc cag caa gag cag ccg tgg agc acc tat ggg gac tat ggc<br>Asn Thr Pro Gln Gln Glu Gln Pro Trp Ser Thr Tyr Gly Asp Tyr Gly<br>465                        470                      475                  480 | 1440 | |
| act cag gct aca atg gag cac tcg gcc ctg ccc ccc atg agt ccc gag<br>Thr Gln Ala Thr Met Glu His Ser Ala Leu Pro Pro Met Ser Pro Glu<br>                    485                      490                      495 | 1488 | |
| agg atc gat gtg gac aat ctg ccg ttt ccc cag gac gtc gaa gac ccc<br>Arg Ile Asp Val Asp Asn Leu Pro Phe Pro Gln Asp Val Glu Asp Pro<br>                        500                      505                      510 | 1536 | |
| gag ctg cct caa gtg act gag act tcg tgg ctg cta gac gga cat ttg<br>Glu Leu Pro Gln Val Thr Glu Thr Ser Trp Leu Leu Asp Gly His Leu<br>                515                      520                      525 | 1584 | |
| cac gcc tac acc aac gac cta gct cgc cga ttg caa gag gag tcc aat<br>His Ala Tyr Thr Asn Asp Leu Ala Arg Arg Leu Gln Glu Glu Ser Asn<br>530                        535                      540 | 1632 | |
| gcc cat tta ctc cac ttt gcc gac tcg caa ata gtc act atg ctg aac<br>Ala His Leu Leu His Phe Ala Asp Ser Gln Ile Val Thr Met Leu Asn<br>545                        550                      555                  560 | 1680 | |
| tcc gag gat gaa gca cag aga aac gtt gcg ttg cgc cgt cta gtc gga<br>Ser Glu Asp Glu Ala Gln Arg Asn Val Ala Leu Arg Arg Leu Val Gly<br>                        565                      570                      575 | 1728 | |
| gac gca gtc aac cct gcc cca ccc atc gcg ttc atg ccc atc aac cga<br>Asp Ala Val Asn Pro Ala Pro Pro Ile Ala Phe Met Pro Ile Asn Arg<br>                    580                      585                      590 | 1776 | |
| gat aac gtc cat tgg tcg ctt ctc gtc gtc gac cgt cga gat aac cac<br>Asp Asn Val His Trp Ser Leu Leu Val Val Asp Arg Arg Asp Asn His<br>                595                      600                      605 | 1824 | |

| | | |
|---|---|---|
| tcg cct gca gcc tac cat tac gat tcc atg gga act ccg cat cca cat<br>Ser Pro Ala Ala Tyr His Tyr Asp Ser Met Gly Thr Pro His Pro His<br>610                                615                         620 | | 1872 |
| cag cac tgg cat gcc caa atg gca gcc tgg cgc ctg ggc ctt gat gct<br>Gln His Trp His Ala Gln Met Ala Ala Trp Arg Leu Gly Leu Asp Ala<br>625                               630                         635                    640 | | 1920 |
| tcg caa gtc tat aaa atg ccc acc gcc ata cag ccg gac ggt tat tct<br>Ser Gln Val Tyr Lys Met Pro Thr Ala Ile Gln Pro Asp Gly Tyr Ser<br>                      645                         650                         655 | | 1968 |
| tgc ggc gat cat gtg ctg acc ggt ata gag gtg ttg gct cat agg gtg<br>Cys Gly Asp His Val Leu Thr Gly Ile Glu Val Leu Ala His Arg Val<br>                 660                         665                         670 | | 2016 |
| atc gac ggc atg ttc gat tac gcg ggc ggc aag gac ctg agc gat atc<br>Ile Asp Gly Met Phe Asp Tyr Ala Gly Gly Lys Asp Leu Ser Asp Ile<br>675                                680                         685 | | 2064 |
| aag cca gac cgc gac ttc atc agg gat cgt ctt gcc cca gcg gat caa<br>Lys Pro Asp Arg Asp Phe Ile Arg Asp Arg Leu Ala Pro Ala Asp Gln<br>690                                695                         700 | | 2112 |
| gcg cca gca gaa agc agc gtc agg tca gtt ccc gag ccg ccc gtc gaa<br>Ala Pro Ala Glu Ser Ser Val Arg Ser Val Pro Glu Pro Pro Val Glu<br>705                                710                         715                    720 | | 2160 |
| cag aag aaa aag aaa agc aag tgg tgg aag ttg tag<br>Gln Lys Lys Lys Lys Ser Lys Trp Trp Lys Leu<br>                      725                         730 | | 2196 |

<210> SEQ ID NO 12
<211> LENGTH: 731
<212> TYPE: PRT
<213> ORGANISM: Pseudomonas syringae

<400> SEQUENCE: 12

Met Trp Asn Phe Asn Asn Trp Ser Lys Gly Leu Asp Ala Tyr Gln Arg
1               5                   10                  15

Leu Gln Glu Thr Gln Ser Lys Leu His Glu Phe Leu Ser Ser Asp Thr
            20                  25                  30

Thr Ser Ser Val Gln Pro Asp Gly Gly Gly Ala His Asp Leu Pro Gln
        35                  40                  45

Arg Gln Arg Tyr Ser Ile Gln Gln Ala Glu Ser Gln Gly Arg Arg Leu
    50                  55                  60

Val Asp Gln Ala Glu Leu Gln Thr Gln Val Glu Arg Arg Phe Ser Lys
65                  70                  75                  80

Lys Ser Glu Thr Arg Tyr Val Thr Glu Val Gln Phe Val Pro Asp His
                85                  90                  95

Leu Glu Asp Thr Glu Tyr Arg Tyr Ser Ser Arg Lys Val Pro Tyr Cys
            100                 105                 110

Glu Asp Ile Ala Leu Ile Glu Arg Phe Cys Glu Gly Ala Leu Leu Gly
        115                 120                 125

Gly Ser Asn Ser Asn Thr Val Asp Phe Tyr Lys Asn Gln Leu Ile Ser
    130                 135                 140

Ile Ser Asp Tyr Leu Gln Arg Gln His Met Pro Ala Ile Asn Ala Arg
145                 150                 155                 160

Leu Phe Ser Asp Ser Leu Glu Ser Asp Leu Lys Gln Tyr Ala Phe Gln
                165                 170                 175

Asn Asn Arg Ser Asp Thr Leu Ala Ile Ile Gly His Leu Arg Arg Ile
            180                 185                 190

Glu Ser Asn Lys His Gly Val Ser Ala Ile Leu Pro Phe Lys Thr Lys
        195                 200                 205

```
Ser Ser Asp Leu Asp Glu Trp Leu Ile Asp Gln Val Phe Ser Asp Glu
    210                 215                 220

Asn Gln Thr Thr Ser Ser Tyr Arg Ser Thr Leu Arg Ala Leu Ser His
225                 230                 235                 240

Trp Leu Ala Ala Gln Glu Lys Pro Gly Leu Cys Asp Pro Asp Tyr Leu
                245                 250                 255

His Ser His Glu Leu Thr Glu Asp Val Leu Lys Phe Ser Cys Leu Pro
            260                 265                 270

Gly Arg His Gln Cys Ser Ala Ala Leu Gln His Met Arg Asn Tyr Asp
        275                 280                 285

Leu Gly Ser Lys Val Arg Leu Lys Lys Gln Arg Asp Thr Arg Asn Ile
    290                 295                 300

Pro Asp Glu Asp Gln Thr Leu Ile Ser His Tyr Gln Lys Ile Ala Asn
305                 310                 315                 320

Asp Ala Leu Val Ile Lys Asn Ser Lys Ala Gly Lys Lys Thr Asn Arg
                325                 330                 335

Asp Pro His Gly Arg Thr Ser Val Asp Lys Tyr Ala Ser Val Leu Arg
            340                 345                 350

Ser Phe Ser Ala Trp Leu Lys Glu Glu Gly Lys Gly Ser Leu Ser Thr
        355                 360                 365

Leu Leu His Asp Pro Glu Leu Asp Thr Tyr Arg Asp Leu Trp Thr His
    370                 375                 380

Asn Lys Ser Ser Ser Asn Ala Lys Thr Val Val Thr Leu Leu Ile Lys
385                 390                 395                 400

Leu Arg Glu Ile Phe Pro Pro Phe Ser Val Glu Ala Val Gln Glu Pro
                405                 410                 415

Ser His Ser Ser Phe Thr Leu Pro Asn Ser Glu Trp Ser Gly Trp Gly
            420                 425                 430

Trp Asn Pro Asp Thr Pro Gln Tyr Pro Pro Gln Ser Pro Ala Ser Thr
        435                 440                 445

Phe Asn Gly Leu Ser Ser Leu Ser Asp Tyr Gly Arg Glu Phe Asp Leu
    450                 455                 460

Asn Thr Pro Gln Gln Glu Gln Pro Trp Ser Thr Tyr Gly Asp Tyr Gly
465                 470                 475                 480

Thr Gln Ala Thr Met Glu His Ser Ala Leu Pro Pro Met Ser Pro Glu
                485                 490                 495

Arg Ile Asp Val Asp Asn Leu Pro Phe Pro Gln Asp Val Glu Asp Pro
            500                 505                 510

Glu Leu Pro Gln Val Thr Glu Thr Ser Trp Leu Leu Asp Gly His Leu
        515                 520                 525

His Ala Tyr Thr Asn Asp Leu Ala Arg Arg Leu Gln Glu Glu Ser Asn
    530                 535                 540

Ala His Leu Leu His Phe Ala Asp Ser Gln Ile Val Thr Met Leu Asn
545                 550                 555                 560

Ser Glu Asp Glu Ala Gln Arg Asn Val Ala Leu Arg Arg Leu Val Gly
                565                 570                 575

Asp Ala Val Asn Pro Ala Pro Pro Ile Ala Phe Met Pro Ile Asn Arg
            580                 585                 590

Asp Asn Val His Trp Ser Leu Leu Val Val Asp Arg Arg Asp Asn His
        595                 600                 605

Ser Pro Ala Ala Tyr His Tyr Asp Ser Met Gly Thr Pro His Pro His
    610                 615                 620
```

```
Gln His Trp His Ala Gln Met Ala Ala Trp Arg Leu Gly Leu Asp Ala
625                 630                 635                 640

Ser Gln Val Tyr Lys Met Pro Thr Ala Ile Gln Pro Asp Gly Tyr Ser
            645                 650                 655

Cys Gly Asp His Val Leu Thr Gly Ile Glu Val Leu Ala His Arg Val
        660                 665                 670

Ile Asp Gly Met Phe Asp Tyr Ala Gly Gly Lys Asp Leu Ser Asp Ile
    675                 680                 685

Lys Pro Asp Arg Asp Phe Ile Arg Asp Arg Leu Ala Pro Ala Asp Gln
690                 695                 700

Ala Pro Ala Glu Ser Ser Val Arg Ser Val Pro Glu Pro Val Glu
705                 710                 715                 720

Gln Lys Lys Lys Ser Lys Trp Trp Lys Leu
                725                 730

<210> SEQ ID NO 13
<211> LENGTH: 1257
<212> TYPE: DNA
<213> ORGANISM: Chlamydia trachomatis
<220> FEATURE:
<221> NAME/KEY: CDS
<222> LOCATION: (1)..(1254)

<400> SEQUENCE: 13 atg ttg tct ccc acc aac tca act tca aag aag gca cct gtt cct cct      48
Met Leu Ser Pro Thr Asn Ser Thr Ser Lys Lys Ala Pro Val Pro Pro
1               5                   10                  15 cag gat tcg tcg aaa cca gtt ctt atc tct gaa gaa cct caa aac caa      96
Gln Asp Ser Ser Lys Pro Val Leu Ile Ser Glu Glu Pro Gln Asn Gln
            20                  25                  30 ctt tta caa aaa gta gct cgt aca gct tta gct gtt ctt ctt gtt gtt     144
Leu Leu Gln Lys Val Ala Arg Thr Ala Leu Ala Val Leu Leu Val Val
        35                  40                  45 gtt act tta gga ttg att ctc ctc ttt tac tcc ttt tct gat cta caa     192
Val Thr Leu Gly Leu Ile Leu Leu Phe Tyr Ser Phe Ser Asp Leu Gln
    50                  55                  60 tcc ttc cct tgg tgc tgc caa aca cgc cct tct act aag gag caa cct     240
Ser Phe Pro Trp Cys Cys Gln Thr Arg Pro Ser Thr Lys Glu Gln Pro
65                  70                  75                  80 acc atc tct att cca gta cct ctt ccg tcc cct cct ctt gcc gta ccg     288
Thr Ile Ser Ile Pro Val Pro Leu Pro Ser Pro Pro Leu Ala Val Pro
                85                  90                  95 cgt cct agt act ccc ccc cct ccc gtc ata tca cgt cct agc acg cct     336
Arg Pro Ser Thr Pro Pro Pro Pro Val Ile Ser Arg Pro Ser Thr Pro
            100                 105                 110 ccc gca cca acc cct gct ata tca cct cct agt act cct tct gct cca     384
Pro Ala Pro Thr Pro Ala Ile Ser Pro Pro Ser Thr Pro Ser Ala Pro
        115                 120                 125 aag ccc tct aca cct cct cct ctt cct cct aag gct ccc aaa cca gtt     432
Lys Pro Ser Thr Pro Pro Pro Leu Pro Pro Lys Ala Pro Lys Pro Val
    130                 135                 140 aaa acg caa gaa gac ctc ctt ccc ttt gtt ccg gag caa gtg ttt gta     480
Lys Thr Gln Glu Asp Leu Leu Pro Phe Val Pro Glu Gln Val Phe Val
145                 150                 155                 160 gag atg tat gaa gat atg gct cga cga tgg atc atc gaa gcg ttg gtt     528
Glu Met Tyr Glu Asp Met Ala Arg Arg Trp Ile Ile Glu Ala Leu Val
                165                 170                 175 cct gct tgg gat tct gac att att ttc aag tgt cta tgc tat ttc cac     576
Pro Ala Trp Asp Ser Asp Ile Ile Phe Lys Cys Leu Cys Tyr Phe His
            180                 185                 190
```

```
acc ctt tac caa ggt ctc att cct ctg gag acc ttc ccc cca gct acc        624
Thr Leu Tyr Gln Gly Leu Ile Pro Leu Glu Thr Phe Pro Pro Ala Thr
        195                 200                 205 ata ttc aac ttt aaa cag aaa atc atc tcg att tta gaa gac aaa aaa        672
Ile Phe Asn Phe Lys Gln Lys Ile Ile Ser Ile Leu Glu Asp Lys Lys
    210                 215                 220 gct gtt tta cga ggg gag cct atc aaa ggc tct ctg cct atc tgc tgt        720
Ala Val Leu Arg Gly Glu Pro Ile Lys Gly Ser Leu Pro Ile Cys Cys
225                 230                 235                 240 tcg gaa gag aat tac cgc cgc cat tta cac gga aca acc ctc ctc cct        768
Ser Glu Glu Asn Tyr Arg Arg His Leu His Gly Thr Thr Leu Leu Pro
                245                 250                 255 gtg ttt atg tgg tat cac cct act cca aaa aca ctc tcg gat acc atg        816
Val Phe Met Trp Tyr His Pro Thr Pro Lys Thr Leu Ser Asp Thr Met
            260                 265                 270 cag act atg aaa cag cta gct ata aaa gga tct gta gga gcg agt cac        864
Gln Thr Met Lys Gln Leu Ala Ile Lys Gly Ser Val Gly Ala Ser His
        275                 280                 285 tgg cta ctt gtt att gtc gat att caa gct cgt cgg ttg gtc tat ttt        912
Trp Leu Leu Val Ile Val Asp Ile Gln Ala Arg Arg Leu Val Tyr Phe
    290                 295                 300 gat agt tta tac aac tat gtg atg tct cca gaa gat atg gaa aaa gat        960
Asp Ser Leu Tyr Asn Tyr Val Met Ser Pro Glu Asp Met Glu Lys Asp
305                 310                 315                 320 ctt caa tcc ttt gct caa caa cta gac cag gtg tat cct gcc tat gac       1008
Leu Gln Ser Phe Ala Gln Gln Leu Asp Gln Val Tyr Pro Ala Tyr Asp
                325                 330                 335 agc cag aaa ttc tct gta aag att gca gca aag gag gta atc caa aaa       1056
Ser Gln Lys Phe Ser Val Lys Ile Ala Ala Lys Glu Val Ile Gln Lys
            340                 345                 350 ggc tcc gga tcc agc tgc ggc gct tgg tgc tgt caa ttt tta cac tgg       1104
Gly Ser Gly Ser Ser Cys Gly Ala Trp Cys Cys Gln Phe Leu His Trp
        355                 360                 365 tat ttg aga gat ccc ttt aca gac gct ttg aat gat ctc ccc gtt gat       1152
Tyr Leu Arg Asp Pro Phe Thr Asp Ala Leu Asn Asp Leu Pro Val Asp
    370                 375                 380 tct gta gaa cgc cat gaa aac cta gcc tca ttt gtc cag gct tgc gaa       1200
Ser Val Glu Arg His Glu Asn Leu Ala Ser Phe Val Gln Ala Cys Glu
385                 390                 395                 400 gcg gct gtt cag gat ctc cca gag ctt ttt tgg cct gaa gca aaa gct       1248
Ala Ala Val Gln Asp Leu Pro Glu Leu Phe Trp Pro Glu Ala Lys Ala
                405                 410                 415 ctt ttc taa                                                           1257
Leu Phe <210> SEQ ID NO 14
<211> LENGTH: 418
<212> TYPE: PRT
<213> ORGANISM: Chlamydia trachomatis

<400> SEQUENCE: 14

Met Leu Ser Pro Thr Asn Ser Thr Ser Lys Lys Ala Pro Val Pro Pro
1               5                   10                  15

Gln Asp Ser Ser Lys Pro Val Leu Ile Ser Glu Glu Pro Gln Asn Gln
            20                  25                  30

Leu Leu Gln Lys Val Ala Arg Thr Ala Leu Ala Val Leu Leu Val Val
        35                  40                  45

Val Thr Leu Gly Leu Ile Leu Leu Phe Tyr Ser Phe Ser Asp Leu Gln
    50                  55                  60
```

```
Ser Phe Pro Trp Cys Cys Gln Thr Arg Pro Ser Thr Lys Glu Gln Pro
 65                  70                  75                  80

Thr Ile Ser Ile Pro Val Pro Leu Pro Ser Pro Pro Leu Ala Val Pro
             85                  90                  95

Arg Pro Ser Thr Pro Pro Pro Val Ile Ser Arg Pro Ser Thr Pro
                100                 105                 110

Pro Ala Pro Thr Pro Ala Ile Ser Pro Pro Ser Thr Pro Ser Ala Pro
                115                 120                 125

Lys Pro Ser Thr Pro Pro Leu Pro Pro Lys Ala Pro Lys Pro Val
130                 135                 140

Lys Thr Gln Glu Asp Leu Leu Pro Phe Val Pro Gln Val Phe Val
145                 150                 155                 160

Glu Met Tyr Glu Asp Met Ala Arg Arg Trp Ile Ile Glu Ala Leu Val
                165                 170                 175

Pro Ala Trp Asp Ser Asp Ile Ile Phe Lys Cys Leu Cys Tyr Phe His
                180                 185                 190

Thr Leu Tyr Gln Gly Leu Ile Pro Leu Glu Thr Phe Pro Pro Ala Thr
                195                 200                 205

Ile Phe Asn Phe Lys Gln Lys Ile Ser Ile Leu Glu Asp Lys Lys
210                 215                 220

Ala Val Leu Arg Gly Glu Pro Ile Lys Gly Ser Leu Pro Ile Cys Cys
225                 230                 235                 240

Ser Glu Glu Asn Tyr Arg Arg His Leu His Gly Thr Thr Leu Leu Pro
                245                 250                 255

Val Phe Met Trp Tyr His Pro Thr Pro Lys Thr Leu Ser Asp Thr Met
                260                 265                 270

Gln Thr Met Lys Gln Leu Ala Ile Lys Gly Ser Val Gly Ala Ser His
                275                 280                 285

Trp Leu Leu Val Ile Val Asp Ile Gln Ala Arg Arg Leu Val Tyr Phe
290                 295                 300

Asp Ser Leu Tyr Asn Tyr Val Met Ser Pro Glu Asp Met Glu Lys Asp
305                 310                 315                 320

Leu Gln Ser Phe Ala Gln Gln Leu Asp Gln Val Tyr Pro Ala Tyr Asp
                325                 330                 335

Ser Gln Lys Phe Ser Val Lys Ile Ala Ala Lys Glu Val Ile Gln Lys
                340                 345                 350

Gly Ser Gly Ser Ser Cys Gly Ala Trp Cys Cys Gln Phe Leu His Trp
                355                 360                 365

Tyr Leu Arg Asp Pro Phe Thr Asp Ala Leu Asn Asp Leu Pro Val Asp
370                 375                 380

Ser Val Glu Arg His Glu Asn Leu Ala Ser Phe Val Gln Ala Cys Glu
385                 390                 395                 400

Ala Ala Val Gln Asp Leu Pro Glu Leu Phe Trp Pro Glu Ala Lys Ala
                405                 410                 415

Leu Phe

<210> SEQ ID NO 15
<211> LENGTH: 1110
<212> TYPE: DNA
<213> ORGANISM: Chlamydia muridarum
<220> FEATURE:
<221> NAME/KEY: CDS
<222> LOCATION: (1)..(1107)

<400> SEQUENCE: 15
```

```
atg gca aaa att tct agt ttt tcc tca ctg ccg act ttt gat gca cca      48
Met Ala Lys Ile Ser Ser Phe Ser Ser Leu Pro Thr Phe Asp Ala Pro
1               5                   10                  15 aaa tct cct ccc tct ttg ttt tct caa agc agt cta tta ggg aaa atc      96
Lys Ser Pro Pro Ser Leu Phe Ser Gln Ser Ser Leu Leu Gly Lys Ile
            20                  25                  30 gct aga ata atc gtt gct tta ttt ttg att ctt gtt tct tta ggt ctt     144
Ala Arg Ile Ile Val Ala Leu Phe Leu Ile Leu Val Ser Leu Gly Leu
        35                  40                  45 atc ctt atc gct tat agg ttc tcc gat ctg tta aac tgc aaa ttt tgt     192
Ile Leu Ile Ala Tyr Arg Phe Ser Asp Leu Leu Asn Cys Lys Phe Cys
50                  55                  60 ata acc aaa act acc gaa tta ccc ata cct tct act aag ata ccg ata     240
Ile Thr Lys Thr Thr Glu Leu Pro Ile Pro Ser Thr Lys Ile Pro Ile
65                  70                  75                  80 tct agt cct cca gtt cct acg act cca cct tat caa aaa aag gaa cct     288
Ser Ser Pro Pro Val Pro Thr Thr Pro Pro Tyr Gln Lys Lys Glu Pro
                85                  90                  95 act ctt ccc caa aaa aat cca aaa att tcc gag aat tta ctc tcc caa     336
Thr Leu Pro Gln Lys Asn Pro Lys Ile Ser Glu Asn Leu Leu Ser Gln
            100                 105                 110 gag gta gtg cag gat tac tta agc tct ggt cga cta ccc gaa ctt gct     384
Glu Val Val Gln Asp Tyr Leu Ser Ser Gly Arg Leu Pro Glu Leu Ala
        115                 120                 125 atc ttg gat aat tct caa atg ttt cag ttt atg tgc gtt tta cac gat     432
Ile Leu Asp Asn Ser Gln Met Phe Gln Phe Met Cys Val Leu His Asp
130                 135                 140 caa tat cct aag ctt ttg cct aac gat tgc tta att cca tta act att     480
Gln Tyr Pro Lys Leu Leu Pro Asn Asp Cys Leu Ile Pro Leu Thr Ile
145                 150                 155                 160 ttc aac tat cgc gag gaa att tgt aat acc att caa gac aag tta aaa     528
Phe Asn Tyr Arg Glu Glu Ile Cys Asn Thr Ile Gln Asp Lys Leu Lys
                165                 170                 175 gct gat caa ggt caa tac tgc tct ctt gga gat cta caa tgc ccc ata     576
Ala Asp Gln Gly Gln Tyr Cys Ser Leu Gly Asp Leu Gln Cys Pro Ile
            180                 185                 190 act tgt tct cct gaa aat tac cat cag cta ttg caa cag tct cgt gta     624
Thr Cys Ser Pro Glu Asn Tyr His Gln Leu Leu Gln Gln Ser Arg Val
        195                 200                 205 ctg ccc ttc tta ctt tgg tat gat cct gag ccc aca aac cat caa caa     672
Leu Pro Phe Leu Leu Trp Tyr Asp Pro Glu Pro Thr Asn His Gln Gln
210                 215                 220 act ctt gaa aaa atg caa gag att gct tcc caa ggg act cca gga aat     720
Thr Leu Glu Lys Met Gln Glu Ile Ala Ser Gln Gly Thr Pro Gly Asn
225                 230                 235                 240 agt cac tgg aca gta att gtt gta gac ttg gat gct cgg tgc atc act     768
Ser His Trp Thr Val Ile Val Val Asp Leu Asp Ala Arg Cys Ile Thr
                245                 250                 255 tat ttt gat agc tta gtt aat tat atc gcc tca aca gat gag atg gaa     816
Tyr Phe Asp Ser Leu Val Asn Tyr Ile Ala Ser Thr Asp Glu Met Glu
            260                 265                 270 cgt cga atg aaa agt tta gct tgt tgt ctt gca aat ata ggg cta tgt     864
Arg Arg Met Lys Ser Leu Ala Cys Cys Leu Ala Asn Ile Gly Leu Cys
        275                 280                 285 aaa aac aac ggc tgt cct ttt gat gtg cac gtc gcc gtt aac gaa tct     912
Lys Asn Asn Gly Cys Pro Phe Asp Val His Val Ala Val Asn Glu Ser
290                 295                 300 tta caa aac tgg atg gga tcc tgt tgt ggt ctg tgg tgc tgc caa tac     960
Leu Gln Asn Trp Met Gly Ser Cys Cys Gly Leu Trp Cys Cys Gln Tyr
```

```
                305                 310                 315                 320
atg aag tgg tat atg gac cat tct cat aca gga att ttg caa aaa att     1008
Met Lys Trp Tyr Met Asp His Ser His Thr Gly Ile Leu Gln Lys Ile
            325                 330                 335 cct gat tcc ctg gca tat aaa act ctc ctt ctc caa tca cta cac tct     1056
Pro Asp Ser Leu Ala Tyr Lys Thr Leu Leu Leu Gln Ser Leu His Ser
        340                 345                 350 act ttt gaa aag ctt atg aaa aaa tac gcc gat ctt tcg tgg cca aca     1104
Thr Phe Glu Lys Leu Met Lys Lys Tyr Ala Asp Leu Ser Trp Pro Thr
    355                 360                 365 act tag                                                              1110
Thr

<210> SEQ ID NO 16
<211> LENGTH: 369
<212> TYPE: PRT
<213> ORGANISM: Chlamydia muridarum

<400> SEQUENCE: 16

Met Ala Lys Ile Ser Ser Phe Ser Ser Leu Pro Thr Phe Asp Ala Pro
1               5                   10                  15

Lys Ser

```
Lys Asn Asn Gly Cys Pro Phe Asp Val His Val Ala Val Asn Glu Ser
    290                 295                 300

Leu Gln Asn Trp Met Gly Ser Cys Cys Gly Leu Trp Cys Cys Gln Tyr
305                 310                 315                 320

Met Lys Trp Tyr Met Asp His Ser His Thr Gly Ile Leu Gln Lys Ile
                325                 330                 335

Pro Asp Ser Leu Ala Tyr Lys Thr Leu Leu Gln Ser Leu His Ser
            340                 345                 350

Thr Phe Glu Lys Leu Met Lys Lys Tyr Ala Asp Leu Ser Trp Pro Thr
        355                 360                 365

Thr

<210> SEQ ID NO 17
<211> LENGTH: 5247
<212> TYPE: DNA
<213> ORGANISM: Mesorhizobium loti
<220> FEATURE:
<221> NAME/KEY: CDS
<222> LOCATION: (1)..(5244)

<400> SEQUENCE: 17 gtg gac cag cga aaa att aca tcc cgt gta aca gct ttg ccg cag gtg    48
Val Asp Gln Arg Lys Ile Thr Ser Arg Val Thr Ala Leu Pro Gln Val
1               5                  10                  15 cag gac gcc ggc ttg gaa gag ggg caa gcg gtc cag gcc cgg caa gtg    96
Gln Asp Ala Gly Leu Glu Glu Gly Gln Ala Val Gln Ala Arg Gln Val
            20                  25                  30 ggc ttt gag cag cac ctt gcc gag gcc cgg agg ctg ttc gat caa gct   144
Gly Phe Glu Gln His Leu Ala Glu Ala Arg Arg Leu Phe Asp Gln Ala
        35                  40                  45 gac gag tcg cca acc aat cca gag gag ctt ctg cga ctg gaa cag ggg   192
Asp Glu Ser Pro Thr Asn Pro Glu Glu Leu Leu Arg Leu Glu Gln Gly
    50                  55                  60 ttc cgc gaa gtg ctt cag cga cgg cag gat gat caa gtg gcc gag gcg   240
Phe Arg Glu Val Leu Gln Arg Arg Gln Asp Asp Gln Val Ala Glu Ala
65                  70                  75                  80 ctc cgg ccg ctg ttc gat gat cga gct gac gag ccg cca gcc aat cca   288
Leu Arg Pro Leu Phe Asp Asp Arg Ala Asp Glu Pro Pro Ala Asn Pro
                85                  90                  95 gag gag ctt ctg cga ctg gaa cag ggg ttc cgc gaa gtg ctt cag cga   336
Glu Glu Leu Leu Arg Leu Glu Gln Gly Phe Arg Glu Val Leu Gln Arg
            100                 105                 110 cgg cag gat gat caa gcc gtc tcg tct ttt ttc agc gac cca ggg atg   384
Arg Gln Asp Asp Gln Ala Val Ser Ser Phe Phe Ser Asp Pro Gly Met
        115                 120                 125 ccc gct gga ccg ggt gac cac aac agc atc gtg acg gac gct ttc gca   432
Pro Ala Gly Pro Gly Asp His Asn Ser Ile Val Thr Asp Ala Phe Ala
    130                 135                 140 gcg gcc ggc tct ggg cac gcc gga gtt gag gcc gcc gcc ccg cca gtc   480
Ala Ala Gly Ser Gly His Ala Gly Val Glu Ala Ala Ala Pro Pro Val
145                 150                 155                 160 ttg gct gcc agc caa cag cag atc cgg ccc tcg ccg gat gcg ctt gac   528
Leu Ala Ala Ser Gln Gln Gln Ile Arg Pro Ser Pro Asp Ala Leu Asp
                165                 170                 175 cag ggc aac cac ctg cca ccc cag ggg ggc atc atc aac aat gaa cat   576
Gln Gly Asn His Leu Pro Pro Gln Gly Gly Ile Ile Asn Asn Glu His
            180                 185                 190 tcg acg gcg ccg ttg cgg cca gcg aag agg cag agg gcc gtg gat agg   624
Ser Thr Ala Pro Leu Arg Pro Ala Lys Arg Gln Arg Ala Val Asp Arg
        195                 200                 205
```

```
ccg caa gcc gtc gcc att cag cag cag ctg agc gaa atc ggc aat tca        672
Pro Gln Ala Val Ala Ile Gln Gln Gln Leu Ser Glu Ile Gly Asn Ser
    210                 215                 220 ggc ggc cgc gtg ccg ata cag ccc ccc acg cag cag ttg ggt gaa ttg        720
Gly Gly Arg Val Pro Ile Gln Pro Pro Thr Gln Gln Leu Gly Glu Leu
225                 230                 235                 240 cca ttg caa ggg gta ccg gtt caa ggg aca ggg tcc gaa cac atc gga        768
Pro Leu Gln Gly Val Pro Val Gln Gly Thr Gly Ser Glu His Ile Gly
                245                 250                 255 agg ctg cat gcg ggg gcc gcg ccc tca gca agg tcc gag gcg ccc ccg        816
Arg Leu His Ala Gly Ala Ala Pro Ser Ala Arg Ser Glu Ala Pro Pro
            260                 265                 270 gct gcg atc gag gac tcc ata aac gtt tcg ttc gcc gtc ccc aaa gac        864
Ala Ala Ile Glu Asp Ser Ile Asn Val Ser Phe Ala Val Pro Lys Asp
        275                 280                 285 ttt tcc cat ggg act caa cgc gtc cca gac gcg atg ctc cct ttc ttg        912
Phe Ser His Gly Thr Gln Arg Val Pro Asp Ala Met Leu Pro Phe Leu
    290                 295                 300 gac cgc cct ggc ccc ttg ccg gat gct ggc caa gcg cgg caa gcg ggc        960
Asp Arg Pro Gly Pro Leu Pro Asp Ala Gly Gln Ala Arg Gln Ala Gly
305                 310                 315                 320 ttt gag cag cac gtg gcc gag ccg cgc cga gcc gac ccg gtt gcg agt       1008
Phe Glu Gln His Val Ala Glu Pro Arg Arg Ala Asp Pro Val Ala Ser
                325                 330                 335 ggc gcc cgt gct tcc cgc tat cac cat ctg tcc gac gaa cac cgg gac       1056
Gly Ala Arg Ala Ser Arg Tyr His His Leu Ser Asp Glu His Arg Asp
            340                 345                 350 ctt att gat aga gcg atc gcc cac tcc cag gaa aaa tat agc gag acc       1104
Leu Ile Asp Arg Ala Ile Ala His Ser Gln Glu Lys Tyr Ser Glu Thr
        355                 360                 365 acg gcc cga aaa tac acg ttt gca ctt agc cgg ttg gcg aat gat ctc       1152
Thr Ala Arg Lys Tyr Thr Phe Ala Leu Ser Arg Leu Ala Asn Asp Leu
    370                 375                 380 agc gct cgt ggc caa gca atc gat cta aga aat cac aaa tcc ctg gtc       1200
Ser Ala Arg Gly Gln Ala Ile Asp Leu Arg Asn His Lys Ser Leu Val
385                 390                 395                 400 gat cac gtc ggt gct ttc ttt ccg aaa gac gtt gat atg aag agc gct       1248
Asp His Val Gly Ala Phe Phe Pro Lys Asp Val Asp Met Lys Ser Ala
                405                 410                 415 ttg aag gcc ctg cgt gcg tat cat gag ccg ggc tat tca gcg act gct       1296
Leu Lys Ala Leu Arg Ala Tyr His Glu Pro Gly Tyr Ser Ala Thr Ala
            420                 425                 430 ggc ggc cct gct gcc agc tat ccc cat ctg tcc gcc gaa cac cgg gac       1344
Gly Gly Pro Ala Ala Ser Tyr Pro His Leu Ser Ala Glu His Arg Asp
        435                 440                 445 gtt att gac aag gcg atc gac cgc gct gcg gct cag caa aac cag agc       1392
Val Ile Asp Lys Ala Ile Asp Arg Ala Ala Ala Gln Gln Asn Gln Ser
    450                 455                 460 gcg gac acg ctg cga ata tac tcg aat gcg ctt cgc cga ttg gcg aat       1440
Ala Asp Thr Leu Arg Ile Tyr Ser Asn Ala Leu Arg Arg Leu Ala Asn
465                 470                 475                 480 gat ctc ggc gct cgt ggc caa gcg act gat cta aaa aat cac caa tcc       1488
Asp Leu Gly Ala Arg Gly Gln Ala Thr Asp Leu Lys Asn His Gln Ser
                485                 490                 495 ctg gtc gat cac ctc gat act ttc ttt ccg aat gac cag aac att aaa       1536
Leu Val Asp His Leu Asp Thr Phe Phe Pro Asn Asp Gln Asn Ile Lys
            500                 505                 510 acg gcg ttg aac gtc cta cgt gcg tat cat gat ccg ggc aat gca gcg       1584
Thr Ala Leu Asn Val Leu Arg Ala Tyr His Asp Pro Gly Asn Ala Ala
```

-continued

|     |     |     |     |     | 515 |     |     |     |     | 520 |     |     |     |     | 525 |     |      |
|-----|-----|-----|-----|-----|-----|-----|-----|-----|-----|-----|-----|-----|-----|-----|-----|-----|------|
| act | ggc | tgg | tgg | cca | gcg | gcg | gtg | ccg | tca | aag | gca | gat | gcg | cgt | atc |     | 1632 |
| Thr | Gly | Trp | Trp | Pro | Ala | Ala | Val | Pro | Ser | Lys | Ala | Asp | Ala | Arg | Ile |     |      |
|     | 530 |     |     |     |     | 535 |     |     |     |     | 540 |     |     |     |     |     |      |
| ctg | gaa | aaa | tta | agc | agt | gac | agc | ggg | ttg | gcc | tta | agc | acc | cgt | gtc |     | 1680 |
| Leu | Glu | Lys | Leu | Ser | Ser | Asp | Ser | Gly | Leu | Ala | Leu | Ser | Thr | Arg | Val |     |      |
| 545 |     |     |     |     | 550 |     |     |     |     | 555 |     |     |     |     | 560 |     |      |
| gtc | tat | ggt | cgt | ctt | ctt | cgc | aga | ttt | tct | gag | gag | ctc | gag | agt | cgg |     | 1728 |
| Val | Tyr | Gly | Arg | Leu | Leu | Arg | Arg | Phe | Ser | Glu | Glu | Leu | Glu | Ser | Arg |     |      |
|     |     |     |     |     | 565 |     |     |     |     | 570 |     |     |     |     | 575 |     |      |
| ggc | cag | acg | atc | tct | ggg | ctg | gat | cac | aat | tcg | cgg | acc | gaa | ctc | gcc |     | 1776 |
| Gly | Gln | Thr | Ile | Ser | Gly | Leu | Asp | His | Asn | Ser | Arg | Thr | Glu | Leu | Ala |     |      |
|     |     |     | 580 |     |     |     |     | 585 |     |     |     |     | 590 |     |     |     |      |
| gag | gcg | ttg | ttt | cca | ggc | aac | aag | aaa | ctc | cgc | ttc | gcg | ctg | cag | cgg |     | 1824 |
| Glu | Ala | Leu | Phe | Pro | Gly | Asn | Lys | Lys | Leu | Arg | Phe | Ala | Leu | Gln | Arg |     |      |
|     | 595 |     |     |     |     | 600 |     |     |     |     | 605 |     |     |     |     |     |      |
| gtt | cac | aat | gcg | gag | gtt | ccc | gag | gcc | ttg | cgg | ccg | ctg | ttc | gat | aat |     | 1872 |
| Val | His | Asn | Ala | Glu | Val | Pro | Glu | Ala | Leu | Arg | Pro | Leu | Phe | Asp | Asn |     |      |
| 610 |     |     |     |     | 615 |     |     |     |     | 620 |     |     |     |     |     |     |      |
| cga | gct | gac | aag | ccg | cca | acc | aat | cca | gag | gag | ctt | ctg | cga | ctg | gaa |     | 1920 |
| Arg | Ala | Asp | Lys | Pro | Pro | Thr | Asn | Pro | Glu | Glu | Leu | Leu | Arg | Leu | Glu |     |      |
| 625 |     |     |     |     | 630 |     |     |     |     | 635 |     |     |     |     | 640 |     |      |
| cag | ggg | ttc | cgc | gaa | gtg | ctt | cag | cag | cgg | cag | ggt | gat | caa | gcc | gcc |     | 1968 |
| Gln | Gly | Phe | Arg | Glu | Val | Leu | Gln | Gln | Arg | Gln | Gly | Asp | Gln | Ala | Ala |     |      |
|     |     |     |     | 645 |     |     |     |     | 650 |     |     |     |     | 655 |     |     |      |
| tcg | tct | ttg | ttc | ggc | aac | cca | ggg | atg | ccc | gct | gga | ccg | gag | gat | cct |     | 2016 |
| Ser | Ser | Leu | Phe | Gly | Asn | Pro | Gly | Met | Pro | Ala | Gly | Pro | Glu | Asp | Pro |     |      |
|     |     | 660 |     |     |     |     | 665 |     |     |     |     | 670 |     |     |     |     |      |
| aac | aga | agc | gtg | tcg | gac | gct | ttc | gca | agc | tct | ggg | cac | gcc | gga | gtt |     | 2064 |
| Asn | Arg | Ser | Val | Ser | Asp | Ala | Phe | Ala | Ser | Ser | Gly | His | Ala | Gly | Val |     |      |
|     |     | 675 |     |     |     |     | 680 |     |     |     |     | 685 |     |     |     |     |      |
| gag | gcc | gcc | gcc | ccg | cca | gtc | ttg | gct | gcc | agc | caa | cag | cag | atc | cgg |     | 2112 |
| Glu | Ala | Ala | Ala | Pro | Pro | Val | Leu | Ala | Ala | Ser | Gln | Gln | Gln | Ile | Arg |     |      |
|     | 690 |     |     |     |     | 695 |     |     |     |     | 700 |     |     |     |     |     |      |
| ccc | tgg | ccg | gat | gcg | ttt | gac | caa | ggc | aac | cac | ctg | cca | ccc | gag | cgg |     | 2160 |
| Pro | Trp | Pro | Asp | Ala | Phe | Asp | Gln | Gly | Asn | His | Leu | Pro | Pro | Glu | Arg |     |      |
| 705 |     |     |     |     | 710 |     |     |     |     | 715 |     |     |     |     | 720 |     |      |
| gtg | atc | atc | aac | aat | gaa | cat | gac | aca | gcg | ctg | ttg | cgg | cca | gcg | gag |     | 2208 |
| Val | Ile | Ile | Asn | Asn | Glu | His | Asp | Thr | Ala | Leu | Leu | Arg | Pro | Ala | Glu |     |      |
|     |     |     |     | 725 |     |     |     |     | 730 |     |     |     |     | 735 |     |     |      |
| agg | cag | agg | gcc | ctg | aat | acg | ccg | caa | gcc | gcc | gcc | att | cag | cag | ccg |     | 2256 |
| Arg | Gln | Arg | Ala | Leu | Asn | Thr | Pro | Gln | Ala | Ala | Ala | Ile | Gln | Gln | Pro |     |      |
|     |     |     | 740 |     |     |     |     | 745 |     |     |     |     | 750 |     |     |     |      |
| ctg | agc | gaa | atc | ggc | aat | tca | ggc | ggc | cgc | gtg | ccg | atg | cag | ccc | ccc |     | 2304 |
| Leu | Ser | Glu | Ile | Gly | Asn | Ser | Gly | Gly | Arg | Val | Pro | Met | Gln | Pro | Pro |     |      |
|     | 755 |     |     |     |     | 760 |     |     |     |     | 765 |     |     |     |     |     |      |
| acg | cag | cag | ttg | ggt | gaa | ttg | cca | ttg | gaa | ggg | gta | ccg | gtt | caa | cgg |     | 2352 |
| Thr | Gln | Gln | Leu | Gly | Glu | Leu | Pro | Leu | Glu | Gly | Val | Pro | Val | Gln | Arg |     |      |
| 770 |     |     |     |     | 775 |     |     |     |     | 780 |     |     |     |     |     |     |      |
| aca | ggg | tcc | gaa | cac | atc | gga | agg | ctg | cat | gcg | gag | gcc | gcg | ccc | tcc |     | 2400 |
| Thr | Gly | Ser | Glu | His | Ile | Gly | Arg | Leu | His | Ala | Glu | Ala | Ala | Pro | Ser |     |      |
| 785 |     |     |     |     | 790 |     |     |     |     | 795 |     |     |     |     | 800 |     |      |
| gca | agg | gct | gag | gca | ccc | ccc | gct | gcc | atc | gag | aac | tcc | ata | aac | gtc |     | 2448 |
| Ala | Arg | Ala | Glu | Ala | Pro | Pro | Ala | Ala | Ile | Glu | Asn | Ser | Ile | Asn | Val |     |      |
|     |     |     |     | 805 |     |     |     |     | 810 |     |     |     |     | 815 |     |     |      |
| tca | ttc | gcc | gtc | ccc | aaa | ggc | ttc | tcc | cat | ggg | act | caa | cgc | gtc | cca |     | 2496 |
| Ser | Phe | Ala | Val | Pro | Lys | Gly | Phe | Ser | His | Gly | Thr | Gln | Arg | Val | Pro |     |      |
|     |     | 820 |     |     |     |     | 825 |     |     |     |     | 830 |     |     |     |     |      |
| gac | gcg | atg | ctc | tct | ttc | ttg | gac | cgc | cct | ggc | ccc | ttg | ccg | gat | gct |     | 2544 |

```
                                                              -continued

Asp Ala Met Leu Ser Phe Leu Asp Arg Pro Gly Pro Leu Pro Asp Ala
        835                 840                 845 ggc caa gcg cgg caa gcg ggt ttt gag cag cac gtg gcc gag ccg cgc      2592
Gly Gln Ala Arg Gln Ala Gly Phe Glu Gln His Val Ala Glu Pro Arg
850                 855                 860 cga gcc gaa cct gtc gcg agt ggc gcc cgt gcc acc ggc tat cgc cat      2640
Arg Ala Glu Pro Val Ala Ser Gly Ala Arg Ala Thr Gly Tyr Arg His
865                 870                 875                 880 ttg tcc gac gaa cac cgc gac ctt atc gat aag gcg atc gcc cac gct      2688
Leu Ser Asp Glu His Arg Asp Leu Ile Asp Lys Ala Ile Ala His Ala
                885                 890                 895 gcg gct cag caa aaa tat agc gag agc acg gtc cta aaa tac agg tat      2736
Ala Ala Gln Gln Lys Tyr Ser Glu Ser Thr Val Leu Lys Tyr Arg Tyr
        900                 905                 910 gca ctt cgc cga ttg gca aat gat ctc ggc gct cgt ggc caa gcg act      2784
Ala Leu Arg Arg Leu Ala Asn Asp Leu Gly Ala Arg Gly Gln Ala Thr
            915                 920                 925 gat cta aaa aat cac caa tcc ctg gtc gat cac ctc gat gct ttc ttt      2832
Asp Leu Lys Asn His Gln Ser Leu Val Asp His Leu Asp Ala Phe Phe
        930                 935                 940 ccg aaa aac gat gat atg aag agg gcg ttg aac gtc ctg cgt gcc tat      2880
Pro Lys Asn Asp Asp Met Lys Arg Ala Leu Asn Val Leu Arg Ala Tyr
945                 950                 955                 960 cat gag ccg ggc tat tca gcg act gtt ggt gcc ccg gct aac cgc tat      2928
His Glu Pro Gly Tyr Ser Ala Thr Val Gly Ala Pro Ala Asn Arg Tyr
                965                 970                 975 ccc cac ttg tcc gac gaa cac cgg gac gtg att gat aag gcg atc gcc      2976
Pro His Leu Ser Asp Glu His Arg Asp Val Ile Asp Lys Ala Ile Ala
            980                 985                 990 cat gct gag gct cag caa cac cat  agc gcg ccg acg ctc  cga ata tac    3024
His Ala Glu Ala Gln Gln His His  Ser Ala Pro Thr Leu  Arg Ile Tyr
        995                 1000                1005 tcg aat  gcg ctt cgc cga ttg  gcg aat gat ctc ggt  gct cgt ggc       3069
Ser Asn Ala Leu Arg Arg Leu  Ala Asn Asp Leu Gly  Ala Arg Gly
    1010                1015                1020 caa gcg  act gat cta aaa aat  cac caa tcc ctg gtc  gat cac ctc       3114
Gln Ala Thr Asp Leu Lys Asn  His Gln Ser Leu Val  Asp His Leu
    1025                1030                1035 aat acc  ttc ttt ccg aaa gac  act gac ata agg gat  ata agg ccg       3159
Asn Thr Phe Phe Pro Lys Asp  Thr Asp Ile Arg Asp  Ile Arg Pro
    1040                1045                1050 gcg ttg  aac gtc ctg cgt gcg  tat cat gag ccg ggc  tat tca gcg       3204
Ala Leu Asn Val Leu Arg Ala  Tyr His Glu Pro Gly  Tyr Ser Ala
    1055                1060                1065 act ggc  cgg tgg cca gtg acg  gtg cct tca aag gca  gat gcg cat       3249
Thr Gly Arg Trp Pro Val Thr  Val Pro Ser Lys Ala  Asp Ala His
    1070                1075                1080 gtc ttg  gaa caa gtg acc agt  gac agc agc ttg gcc  cca agc acc       3294
Val Leu Glu Gln Val Thr Ser  Asp Ser Ser Leu Ala  Pro Ser Thr
    1085                1090                1095 cgt gtt  gtc tat ggt cat agt  ctt cgc aga ttt tct  gag gcg ctt       3339
Arg Val Val Tyr Gly His Ser  Leu Arg Arg Phe Ser  Glu Ala Leu
    1100                1105                1110 gac agg  cgg ggc cgg acg atc  tct ggg ctg gat cat  gat tcg cgg       3384
Asp Arg Arg Gly Arg Thr Ile  Ser Gly Leu Asp His  Asp Ser Arg
    1115                1120                1125 atc gaa  ttc gcc gag gtg tta  ttt cca ggc aac gat  tat ctc cgc       3429
Ile Glu Phe Ala Glu Val Leu  Phe Pro Gly Asn Asp  Tyr Leu Arg
    1130                1135                1140
```

```
tgg gcg ctt gaa cgg gtt cgc gat gcg aag cct gcg tca gac agg      3474
Trp Ala Leu Glu Arg Val Arg Asp Ala Lys Pro Ala Ser Asp Arg
    1145            1150                1155 atc gtg gcg gac gct ttg gca gcg gcc ggc tct ggg cac gcc gga      3519
Ile Val Ala Asp Ala Leu Ala Ala Ala Gly Ser Gly His Ala Gly
1160            1165                1170 gtt gag gcc gcc gcc ccg cca gtc ttg gct gcc agc caa cag cag      3564
Val Glu Ala Ala Ala Pro Pro Val Leu Ala Ala Ser Gln Gln Gln
    1175            1180                1185 atc cgg ccc tgg ccg gat gcg ctt gac cag ggc aac ctc ctg cca      3609
Ile Arg Pro Trp Pro Asp Ala Leu Asp Gln Gly Asn Leu Leu Pro
1190            1195                1200 ccc gag cgg ttc atc atc aac aat gaa cat tcg acg gcg ccg ttg      3654
Pro Glu Arg Phe Ile Ile Asn Asn Glu His Ser Thr Ala Pro Leu
    1205            1210                1215 cgg ccg gcg gag agg cag agg gcc ctg aat acg cca caa gcc gcc      3699
Arg Pro Ala Glu Arg Gln Arg Ala Leu Asn Thr Pro Gln Ala Ala
1220            1225                1230 gcc att cag cag cag ccg agc gaa atc ggc aat tca ggc ggc cgc      3744
Ala Ile Gln Gln Gln Pro Ser Glu Ile Gly Asn Ser Gly Gly Arg
    1235            1240                1245 atg ccg atg cag ccc ccc atg tgg caa ttg ggt gaa ttg cca ttg      3789
Met Pro Met Gln Pro Pro Met Trp Gln Leu Gly Glu Leu Pro Leu
1250            1255                1260 caa ggg gta ccg gtt caa ggg aca ggg tcc gaa cac atc gga agg      3834
Gln Gly Val Pro Val Gln Gly Thr Gly Ser Glu His Ile Gly Arg
    1265            1270                1275 ctg cat gcg ggg gcc gcg ccc tca gca agg tcc gag gcg ccc ccg      3879
Leu His Ala Gly Ala Ala Pro Ser Ala Arg Ser Glu Ala Pro Pro
1280            1285                1290 gct gcg atc gag gac tcc ata aat gtt tcg ttc gcc gtg ccc aaa      3924
Ala Ala Ile Glu Asp Ser Ile Asn Val Ser Phe Ala Val Pro Lys
    1295            1300                1305 ggc ttc tcc cat gtg act caa cgc gtc cca gag gcg atg ctc tct      3969
Gly Phe Ser His Val Thr Gln Arg Val Pro Glu Ala Met Leu Ser
1310            1315                1320 tcc ttg tac cat tat ggc ctc ttg ccg gac gcg gac aag ccg gaa      4014
Ser Leu Tyr His Tyr Gly Leu Leu Pro Asp Ala Asp Lys Pro Glu
    1325            1330                1335 tgg aac tac gag att aaa ggc cac ggc tac acc gcc cgg agg cca      4059
Trp Asn Tyr Glu Ile Lys Gly His Gly Tyr Thr Ala Arg Arg Pro
1340            1345                1350 gag gag ggc aac gac gtt tgg ctc ctc cat cgc gga gcg ata agg      4104
Glu Glu Gly Asn Asp Val Trp Leu Leu His Arg Gly Ala Ile Arg
    1355            1360                1365 gaa gct gga gcg gca gca gta ccg gca agg gct ccg gga ccc gcc      4149
Glu Ala Gly Ala Ala Ala Val Pro Ala Arg Ala Pro Gly Pro Ala
1370            1375                1380 ttg cca gcg acc gcc agg ctc tca gac acc cat ctc ggg gtt ccg      4194
Leu Pro Ala Thr Ala Arg Leu Ser Asp Thr His Leu Gly Val Pro
    1385            1390                1395 ttg gtc gat ctg acc acc tcc tcc gat gca cac atc gaa gcc ctt      4239
Leu Val Asp Leu Thr Thr Ser Ser Asp Ala His Ile Glu Ala Leu
1400            1405                1410 ccg tca ggc tcg tcc aat ctc ccc cgg ggg gcg gtg ctc ggg gcc      4284
Pro Ser Gly Ser Ser Asn Leu Pro Arg Gly Ala Val Leu Gly Ala
    1415            1420                1425 acc caa ctg ctg ggc gac gaa cat atc cag agg gat tac gaa ttc      4329
Thr Gln Leu Leu Gly Asp Glu His Ile Gln Arg Asp Tyr Glu Phe
1430            1435                1440
```

-continued

| | | |
|---|---|---|
| ctc gag cag cag ctg cag cag gcc gat cca gcg ctc gcc gcc cgg<br>Leu Glu Gln Gln Leu Gln Gln Ala Asp Pro Ala Leu Ala Ala Arg<br>1445                      1450                    1455 | 4374 |
| acg cgg ctg gtc gat ccg tcg gtc tcc cat ctg ctg cgc cac atg<br>Thr Arg Leu Val Asp Pro Ser Val Ser His Leu Leu Arg His Met<br>1460                      1465                    1470 | 4419 |
| gag cag caa gac gcg cga ggc aca ttg cag tcg att tat aat cga<br>Glu Gln Gln Asp Ala Arg Gly Thr Leu Gln Ser Ile Tyr Asn Arg<br>1475                      1480                    1485 | 4464 |
| aac gcc ggc cca tcc gac ttc ctg ttc gtg cca gtg aac gat ggg<br>Asn Ala Gly Pro Ser Asp Phe Leu Phe Val Pro Val Asn Asp Gly<br>1490                      1495                    1500 | 4509 |
| gtg ggt att gac cgc ggc acc cat tgg tcg ctg ctc gta gat<br>Val Gly Ile Asp Arg Gly Thr His Trp Ser Leu Leu Leu Val Asp<br>1505                      1510                    1515 | 4554 |
| cgc cgc gat ccg gaa aga gcg gtc gcc tat cac tac gac tcc atc<br>Arg Arg Asp Pro Glu Arg Ala Val Ala Tyr His Tyr Asp Ser Ile<br>1520                      1525                    1530 | 4599 |
| cag caa aat gaa cag cga tac aac gac gcg cct gca cga aag ctc<br>Gln Gln Asn Glu Gln Arg Tyr Asn Asp Ala Pro Ala Arg Lys Leu<br>1535                      1540                    1545 | 4644 |
| gct aca aga ctg gac gcg acc ctg gta aca ccc gac atg gcg cag<br>Ala Thr Arg Leu Asp Ala Thr Leu Val Thr Pro Asp Met Ala Gln<br>1550                      1555                    1560 | 4689 |
| cag aaa aac gct gtt gac tgc ggc gtc ttc gtg gtg gac ggc acg<br>Gln Lys Asn Ala Val Asp Cys Gly Val Phe Val Val Asp Gly Thr<br>1565                      1570                    1575 | 4734 |
| cgc gag ctg gtt cgt cga ttg gcg aac gaa gag cgg cca gac cag<br>Arg Glu Leu Val Arg Arg Leu Ala Asn Glu Glu Arg Pro Asp Gln<br>1580                      1585                    1590 | 4779 |
| cag ctg ccg ctg cac ctc aac tac ctc gtc gcc gat cgg cag gcg<br>Gln Leu Pro Leu His Leu Asn Tyr Leu Val Ala Asp Arg Gln Ala<br>1595                      1600                    1605 | 4824 |
| ctg caa aac cga ctg aga gag ggg cgc ttg ccg cac gag ctt gcc<br>Leu Gln Asn Arg Leu Arg Glu Gly Arg Leu Pro His Glu Leu Ala<br>1610                      1615                    1620 | 4869 |
| gca agc cct gcc gaa gct ttg gca gca ccc ggg tcg cag gtg caa<br>Ala Ser Pro Ala Glu Ala Leu Ala Ala Pro Gly Ser Gln Val Gln<br>1625                      1630                    1635 | 4914 |
| cac gcc gcc ttg caa gag cag caa gcc aga cag gtc gcg cca gcg<br>His Ala Ala Leu Gln Glu Gln Gln Ala Arg Gln Val Ala Pro Ala<br>1640                      1645                    1650 | 4959 |
| ccg ttg gaa cgg cac ttg ggc aag acg cgc gag gcc gag gac aag<br>Pro Leu Glu Arg His Leu Gly Lys Thr Arg Glu Ala Glu Asp Lys<br>1655                      1660                    1665 | 5004 |
| ctg acg agt aca ctg gac agg agc aac cgc gtg aac agc ggg ggc<br>Leu Thr Ser Thr Leu Asp Arg Ser Asn Arg Val Asn Ser Gly Gly<br>1670                      1675                    1680 | 5049 |
| gtc gtc atc aac act gaa cgt tac aca gcg ccg ttg aga ccg gcg<br>Val Val Ile Asn Thr Glu Arg Tyr Thr Ala Pro Leu Arg Pro Ala<br>1685                      1690                    1695 | 5094 |
| aaa agg cag agg act gac aat tcg caa agc ctc gcc atc ggg cgg<br>Lys Arg Gln Arg Thr Asp Asn Ser Gln Ser Leu Ala Ile Gly Arg<br>1700                      1705                    1710 | 5139 |
| cag ccg agc gaa gca aac aca acg tcc atc ggc caa gcc tcc gat<br>Gln Pro Ser Glu Ala Asn Thr Thr Ser Ile Gly Gln Ala Ser Asp<br>1715                      1720                    1725 | 5184 |
| caa gcc cga gcg gac cta atg gct tcc tcc aga agc aga gag cgc<br>Gln Ala Arg Ala Asp Leu Met Ala Ser Ser Arg Ser Arg Glu Arg | 5229 |

```
                1730            1735            1740
tcc gac gcg gga cgt tga                                        5247
Ser Asp Ala Gly Arg
    1745

<210> SEQ ID NO 18
<211> LENGTH: 1748
<212> TYPE: PRT
<213> ORGANISM: Mesorhizobium loti

<400> SEQUENCE: 18

Val Asp Gln Arg Lys Ile Thr Ser Arg Val Thr Ala Leu Pro Gln Val
1               5                   10                  15

Gln Asp Ala Gly Leu Glu Glu Gly Gln Ala Val Gln Ala Arg Gln Val
            20                  25                  30

Gly Phe Glu Gln His Leu Ala Glu Ala Arg Arg Leu Phe Asp Gln Ala
        35                  40                  45

Asp Glu Ser Pro Thr Asn Pro Glu Glu Leu Leu Arg Leu Glu Gln Gly
    50                  55                  60

Phe Arg Glu Val Leu Gln Arg Arg Gln Asp Asp Gln Val Ala Glu Ala
65                  70                  75                  80

Leu Arg Pro Leu Phe Asp Asp Arg Ala Asp Glu Pro Pro Ala Asn Pro
                85                  90                  95

Glu Glu Leu Leu Arg Leu Glu Gln Gly Phe Arg Glu Val Leu Gln Arg
            100                 105                 110

Arg Gln Asp Asp Gln Ala Val Ser Ser Phe Phe Ser Asp Pro Gly Met
        115                 120                 125

Pro Ala Gly Pro Gly Asp His Asn Ser Ile Val Thr Asp Ala Phe Ala
    130                 135                 140

Ala Ala Gly Ser Gly His Ala Gly Val Glu Ala Ala Pro Pro Val
145                 150                 155                 160

Leu Ala Ala Ser Gln Gln Ile Arg Pro Ser Pro Asp Ala Leu Asp
                165                 170                 175

Gln Gly Asn His Leu Pro Pro Gln Gly Gly Ile Ile Asn Asn Glu His
            180                 185                 190

Ser Thr Ala Pro Leu Arg Pro Ala Lys Arg Gln Arg Ala Val Asp Arg
        195                 200                 205

Pro Gln Ala Val Ala Ile Gln Gln Gln Leu Ser Glu Ile Gly Asn Ser
    210                 215                 220

Gly Gly Arg Val Pro Ile Gln Pro Pro Thr Gln Leu Gly Glu Leu
225                 230                 235                 240

Pro Leu Gln Gly Val Pro Val Gln Gly Thr Gly Ser Glu His Ile Gly
                245                 250                 255

Arg Leu His Ala Gly Ala Ala Pro Ser Ala Arg Ser Glu Ala Pro Pro
            260                 265                 270

Ala Ala Ile Glu Asp Ser Ile Asn Val Ser Phe Ala Val Pro Lys Asp
        275                 280                 285

Phe Ser His Gly Thr Gln Arg Val Pro Asp Ala Met Leu Pro Phe Leu
    290                 295                 300

Asp Arg Pro Gly Pro Leu Pro Asp Ala Gly Gln Ala Arg Gln Ala Gly
305                 310                 315                 320

Phe Glu Gln His Val Ala Glu Pro Arg Ala Asp Pro Val Ala Ser
                325                 330                 335

Gly Ala Arg Ala Ser Arg Tyr His His Leu Ser Asp Glu His Arg Asp
            340                 345                 350
```

```
Leu Ile Asp Arg Ala Ile Ala His Ser Gln Glu Lys Tyr Ser Glu Thr
        355                 360                 365

Thr Ala Arg Lys Tyr Thr Phe Ala Leu Ser Arg Leu Ala Asn Asp Leu
    370                 375                 380

Ser Ala Arg Gly Gln Ala Ile Asp Leu Arg Asn His Lys Ser Leu Val
385                 390                 395                 400

Asp His Val Gly Ala Phe Phe Pro Lys Asp Val Asp Met Lys Ser Ala
                405                 410                 415

Leu Lys Ala Leu Arg Ala Tyr His Glu Pro Gly Tyr Ser Ala Thr Ala
            420                 425                 430

Gly Gly Pro Ala Ala Ser Tyr Pro His Leu Ser Ala Glu His Arg Asp
        435                 440                 445

Val Ile Asp Lys Ala Ile Asp Arg Ala Ala Ala Gln Gln Asn Gln Ser
    450                 455                 460

Ala Asp Thr Leu Arg Ile Tyr Ser Asn Ala Leu Arg Arg Leu Ala Asn
465                 470                 475                 480

Asp Leu Gly Ala Arg Gly Gln Ala Thr Asp Leu Lys Asn His Gln Ser
                485                 490                 495

Leu Val Asp His Leu Asp Thr Phe Phe Pro Asn Asp Gln Asn Ile Lys
            500                 505                 510

Thr Ala Leu Asn Val Leu Arg Ala Tyr His Asp Pro Gly Asn Ala Ala
        515                 520                 525

Thr Gly Trp Trp Pro Ala Ala Val Pro Ser Lys Ala Asp Ala Arg Ile
    530                 535                 540

Leu Glu Lys Leu Ser Ser Asp Ser Gly Leu Ala Leu Ser Thr Arg Val
545                 550                 555                 560

Val Tyr Gly Arg Leu Leu Arg Arg Phe Ser Glu Glu Leu Glu Ser Arg
                565                 570                 575

Gly Gln Thr Ile Ser Gly Leu Asp His Asn Ser Arg Thr Glu Leu Ala
            580                 585                 590

Glu Ala Leu Phe Pro Gly Asn Lys Lys Leu Arg Phe Ala Leu Gln Arg
        595                 600                 605

Val His Asn Ala Glu Val Pro Glu Ala Leu Arg Pro Leu Phe Asp Asn
    610                 615                 620

Arg Ala Asp Lys Pro Pro Thr Asn Pro Glu Glu Leu Leu Arg Leu Glu
625                 630                 635                 640

Gln Gly Phe Arg Glu Val Leu Gln Gln Arg Gln Gly Asp Gln Ala Ala
                645                 650                 655

Ser Ser Leu Phe Gly Asn Pro Gly Met Pro Ala Gly Pro Glu Asp Pro
            660                 665                 670

Asn Arg Ser Val Ser Asp Ala Phe Ala Ser Ser Gly His Ala Gly Val
        675                 680                 685

Glu Ala Ala Ala Pro Pro Val Leu Ala Ala Ser Gln Gln Gln Ile Arg
    690                 695                 700

Pro Trp Pro Asp Ala Phe Asp Gln Gly Asn His Leu Pro Pro Glu Arg
705                 710                 715                 720

Val Ile Ile Asn Asn Glu His Asp Thr Ala Leu Leu Arg Pro Ala Glu
                725                 730                 735

Arg Gln Arg Ala Leu Asn Thr Pro Gln Ala Ala Ile Gln Gln Pro
            740                 745                 750

Leu Ser Glu Ile Gly Asn Ser Gly Gly Arg Val Pro Met Gln Pro Pro
        755                 760                 765
```

-continued

```
Thr Gln Gln Leu Gly Glu Leu Pro Leu Glu Gly Val Pro Val Gln Arg
    770                 775                 780
Thr Gly Ser Glu His Ile Gly Arg Leu His Ala Glu Ala Ala Pro Ser
785                 790                 795                 800
Ala Arg Ala Glu Ala Pro Pro Ala Ala Ile Glu Asn Ser Ile Asn Val
                805                 810                 815
Ser Phe Ala Val Pro Lys Gly Phe Ser His Gly Thr Gln Arg Val Pro
            820                 825                 830
Asp Ala Met Leu Ser Phe Leu Asp Arg Pro Gly Pro Leu Pro Asp Ala
        835                 840                 845
Gly Gln Ala Arg Gln Ala Gly Phe Glu Gln His Val Ala Glu Pro Arg
    850                 855                 860
Arg Ala Glu Pro Val Ala Ser Gly Ala Arg Ala Thr Gly Tyr Arg His
865                 870                 875                 880
Leu Ser Asp Glu His Arg Asp Leu Ile Asp Lys Ala Ile Ala His Ala
                885                 890                 895
Ala Ala Gln Gln Lys Tyr Ser Glu Ser Thr Val Leu Lys Tyr Arg Tyr
            900                 905                 910
Ala Leu Arg Arg Leu Ala Asn Asp Leu Gly Ala Arg Gly Gln Ala Thr
        915                 920                 925
Asp Leu Lys Asn His Gln Ser Leu Val Asp His Leu Asp Ala Phe Phe
    930                 935                 940
Pro Lys Asn Asp Asp Met Lys Arg Ala Leu Asn Val Leu Arg Ala Tyr
945                 950                 955                 960
His Glu Pro Gly Tyr Ser Ala Thr Val Gly Ala Pro Ala Asn Arg Tyr
                965                 970                 975
Pro His Leu Ser Asp Glu His Arg Asp Val Ile Asp Lys Ala Ile Ala
            980                 985                 990
His Ala Glu Ala Gln Gln His His Ser Ala Pro Thr Leu Arg Ile Tyr
        995                 1000                1005
Ser Asn Ala Leu Arg Arg Leu Ala Asn Asp Leu Gly Ala Arg Gly
        1010                1015                1020
Gln Ala Thr Asp Leu Lys Asn His Gln Ser Leu Val Asp His Leu
        1025                1030                1035
Asn Thr Phe Phe Pro Lys Asp Thr Asp Ile Arg Asp Ile Arg Pro
        1040                1045                1050
Ala Leu Asn Val Leu Arg Ala Tyr His Glu Pro Gly Tyr Ser Ala
        1055                1060                1065
Thr Gly Arg Trp Pro Val Thr Val Pro Ser Lys Ala Asp Ala His
        1070                1075                1080
Val Leu Glu Gln Val Thr Ser Asp Ser Ser Leu Ala Pro Ser Thr
        1085                1090                1095
Arg Val Val Tyr Gly His Ser Leu Arg Arg Phe Ser Glu Ala Leu
        1100                1105                1110
Asp Arg Arg Gly Arg Thr Ile Ser Gly Leu Asp His Asp Ser Arg
        1115                1120                1125
Ile Glu Phe Ala Glu Val Leu Phe Pro Gly Asn Asp Tyr Leu Arg
        1130                1135                1140
Trp Ala Leu Glu Arg Val Arg Asp Ala Lys Pro Ala Ser Asp Arg
        1145                1150                1155
Ile Val Ala Asp Ala Leu Ala Ala Ala Gly Ser Gly His Ala Gly
        1160                1165                1170
Val Glu Ala Ala Ala Pro Pro Val Leu Ala Ala Ser Gln Gln Gln
```

-continued

```
            1175                1180                1185

Ile Arg Pro Trp Pro Asp Ala Leu Asp Gln Gly Asn Leu Leu Pro
    1190                1195                1200

Pro Glu Arg Phe Ile Ile Asn Asn Glu His Ser Thr Ala Pro Leu
    1205                1210                1215

Arg Pro Ala Glu Arg Gln Arg Ala Leu Asn Thr Pro Gln Ala Ala
    1220                1225                1230

Ala Ile Gln Gln Gln Pro Ser Glu Ile Gly Asn Ser Gly Gly Arg
    1235                1240                1245

Met Pro Met Gln Pro Pro Met Trp Gln Leu Gly Glu Leu Pro Leu
    1250                1255                1260

Gln Gly Val Pro Val Gln Gly Thr Gly Ser Glu His Ile Gly Arg
    1265                1270                1275

Leu His Ala Gly Ala Ala Pro Ser Ala Arg Ser Glu Ala Pro Pro
    1280                1285                1290

Ala Ala Ile Glu Asp Ser Ile Asn Val Ser Phe Ala Val Pro Lys
    1295                1300                1305

Gly Phe Ser His Val Thr Gln Arg Val Pro Glu Ala Met Leu Ser
    1310                1315                1320

Ser Leu Tyr His Tyr Gly Leu Leu Pro Asp Ala Asp Lys Pro Glu
    1325                1330                1335

Trp Asn Tyr Glu Ile Lys Gly His Gly Tyr Thr Ala Arg Arg Pro
    1340                1345                1350

Glu Glu Gly Asn Asp Val Trp Leu Leu His Arg Gly Ala Ile Arg
    1355                1360                1365

Glu Ala Gly Ala Ala Ala Val Pro Ala Arg Ala Pro Gly Pro Ala
    1370                1375                1380

Leu Pro Ala Thr Ala Arg Leu Ser Asp Thr His Leu Gly Val Pro
    1385                1390                1395

Leu Val Asp Leu Thr Thr Ser Ser Asp Ala His Ile Glu Ala Leu
    1400                1405                1410

Pro Ser Gly Ser Ser Asn Leu Pro Arg Gly Ala Val Leu Gly Ala
    1415                1420                1425

Thr Gln Leu Leu Gly Asp Glu His Ile Gln Arg Asp Tyr Glu Phe
    1430                1435                1440

Leu Glu Gln Gln Leu Gln Gln Ala Asp Pro Ala Leu Ala Ala Arg
    1445                1450                1455

Thr Arg Leu Val Asp Pro Ser Val Ser His Leu Leu Arg His Met
    1460                1465                1470

Glu Gln Gln Asp Ala Arg Gly Thr Leu Gln Ser Ile Tyr Asn Arg
    1475                1480                1485

Asn Ala Gly Pro Ser Asp Phe Leu Phe Val Pro Val Asn Asp Gly
    1490                1495                1500

Val Gly Ile Asp Arg Gly Thr His Trp Ser Leu Leu Leu Val Asp
    1505                1510                1515

Arg Arg Asp Pro Glu Arg Ala Val Ala Tyr His Tyr Asp Ser Ile
    1520                1525                1530

Gln Gln Asn Glu Gln Arg Tyr Asn Asp Ala Pro Ala Arg Lys Leu
    1535                1540                1545

Ala Thr Arg Leu Asp Ala Thr Leu Val Thr Pro Asp Met Ala Gln
    1550                1555                1560

Gln Lys Asn Ala Val Asp Cys Gly Val Phe Val Val Asp Gly Thr
    1565                1570                1575
```

```
Arg Glu  Leu Val Arg Arg Leu  Ala Asn Glu Glu Arg  Pro Asp Gln
    1580             1585                 1590

Gln Leu  Pro Leu His Leu Asn  Tyr Leu Val Ala Asp  Arg Gln Ala
    1595             1600                 1605

Leu Gln  Asn Arg Leu Arg Glu  Gly Arg Leu Pro His  Glu Leu Ala
    1610             1615                 1620

Ala Ser  Pro Ala Glu Ala Leu  Ala Ala Pro Gly Ser  Gln Val Gln
    1625             1630                 1635

His Ala  Ala Leu Gln Glu Gln  Gln Ala Arg Gln Val  Ala Pro Ala
    1640             1645                 1650

Pro Leu  Glu Arg His Leu Gly  Lys Thr Arg Glu Ala  Glu Asp Lys
    1655             1660                 1665

Leu Thr  Ser Thr Leu Asp Arg  Ser Asn Arg Val Asn  Ser Gly Gly
    1670             1675                 1680

Val Val  Ile Asn Thr Glu Arg  Tyr Thr Ala Pro Leu  Arg Pro Ala
    1685             1690                 1695

Lys Arg  Gln Arg Thr Asp Asn  Ser Gln Ser Leu Ala  Ile Gly Arg
    1700             1705                 1710

Gln Pro  Ser Glu Ala Asn Thr  Thr Ser Ile Gly Gln  Ala Ser Asp
    1715             1720                 1725

Gln Ala  Arg Ala Asp Leu Met  Ala Ser Ser Arg Ser  Arg Glu Arg
    1730             1735                 1740

Ser Asp  Ala Gly Arg
    1745

<210> SEQ ID NO 19
<211> LENGTH: 1902
<212> TYPE: DNA
<213> ORGANISM: Rickettsia conorii
<220> FEATURE:
<221> NAME/KEY: CDS
<222> LOCATION: (1)..(1899)

<400> SEQUENCE: 19 atg gct gag tct att ata ttt act ctt tta ctt gga ggt gaa gat cgg      48
Met Ala Glu Ser Ile Ile Phe Thr Leu Leu Leu Gly Gly Glu Asp Arg
1               5                   10                  15 ata tta gag aaa ata aac aag cag gaa act caa aat aaa ctg cct att      96
Ile Leu Glu Lys Ile Asn Lys Gln Glu Thr Gln Asn Lys Leu Pro Ile
            20                  25                  30 atc cgg cta gaa gtt aat aaa gca tca cat ata ccc gat aaa gaa cgt     144
Ile Arg Leu Glu Val Asn Lys Ala Ser His Ile Pro Asp Lys Glu Arg
        35                  40                  45 att ttt tcg gag atc tta caa gaa tcc cac aaa aag ggc aaa aca ccg     192
Ile Phe Ser Glu Ile Leu Gln Glu Ser His Lys Lys Gly Lys Thr Pro
    50                  55                  60 att ttt aat att caa ctt aat aac aat aat ata caa ccc att ttt acg     240
Ile Phe Asn Ile Gln Leu Asn Asn Asn Asn Ile Gln Pro Ile Phe Thr
65                  70                  75                  80 gta caa gat tta att aat tta caa aat tta aat ata aaa act act att     288
Val Gln Asp Leu Ile Asn Leu Gln Asn Leu Asn Ile Lys Thr Thr Ile
                85                  90                  95 act ttt gat caa tat aat tca tta ccc caa aat tct gaa cta gaa gct     336
Thr Phe Asp Gln Tyr Asn Ser Leu Pro Gln Asn Ser Glu Leu Glu Ala
            100                 105                 110 tat tgg aag caa att atg aaa aaa gtt gat cat gtt ttt ttt aca aat     384
Tyr Trp Lys Gln Ile Met Lys Lys Val Asp His Val Phe Phe Thr Asn
        115                 120                 125
```

-continued

| | | |
|---|---|---|
| gaa gca gat caa aat tta tct ata gcc gat ggt ata gta cca aaa gat<br>Glu Ala Asp Gln Asn Leu Ser Ile Ala Asp Gly Ile Val Pro Lys Asp<br>130     135     140 | 432 |
| aaa gcc act aca att acg gat ata agt tta gta aca tct gtt ttt aac<br>Lys Ala Thr Thr Ile Thr Asp Ile Ser Leu Val Thr Ser Val Phe Asn<br>145     150     155     160 | 480 |
| aat ctt gta tct gat cgt aaa att gat caa tta ctt tcc ggt aca ata<br>Asn Leu Val Ser Asp Arg Lys Ile Asp Gln Leu Leu Ser Gly Thr Ile<br>     165     170     175 | 528 |
| cct gat aaa gaa aag cta gat aaa ata ata aaa aac gct aaa aat caa<br>Pro Asp Lys Glu Lys Leu Asp Lys Ile Ile Lys Asn Ala Lys Asn Gln<br>180     185     190 | 576 |
| ggc ggt aga gtg att ata gaa act tgg cct ctt tct gca gac gaa gca<br>Gly Gly Arg Val Ile Ile Glu Thr Trp Pro Leu Ser Ala Asp Glu Ala<br>195     200     205 | 624 |
| aca aat ctt atc act gct aaa ttc ggt att acc tct gaa gat caa att<br>Thr Asn Leu Ile Thr Ala Lys Phe Gly Ile Thr Ser Glu Asp Gln Ile<br>210     215     220 | 672 |
| tac gga ttg aaa ctc gaa att aat gaa atc tta aaa gat gca aat aat<br>Tyr Gly Leu Lys Leu Glu Ile Asn Glu Ile Leu Lys Asp Ala Asn Asn<br>225     230     235     240 | 720 |
| gct gct gaa aac tta aaa aaa tat gta tca caa ata tct agg caa ttt<br>Ala Ala Glu Asn Leu Lys Lys Tyr Val Ser Gln Ile Ser Arg Gln Phe<br>     245     250     255 | 768 |
| caa aaa gat tta ggt aaa act gag gta aat cct att gac ttt aat ttt<br>Gln Lys Asp Leu Gly Lys Thr Glu Val Asn Pro Ile Asp Phe Asn Phe<br>260     265     270 | 816 |
| att aat aca aag aaa gtt att aat gat aaa cct aag gat ata caa gta<br>Ile Asn Thr Lys Lys Val Ile Asn Asp Lys Pro Lys Asp Ile Gln Val<br>275     280     285 | 864 |
| gaa caa aca ata tca tat gaa cct cta aaa gca aac caa cca caa ccg<br>Glu Gln Thr Ile Ser Tyr Glu Pro Leu Lys Ala Asn Gln Pro Gln Pro<br>290     295     300 | 912 |
| caa ggt ttt ttt aaa aga att ttt aac tat ttt aaa gat ata ata act<br>Gln Gly Phe Phe Lys Arg Ile Phe Asn Tyr Phe Lys Asp Ile Ile Thr<br>305     310     315     320 | 960 |
| agt ttt aaa gaa gca ata ttc ggc aaa aaa gaa gaa cct aaa act cac<br>Ser Phe Lys Glu Ala Ile Phe Gly Lys Lys Glu Glu Pro Lys Thr His<br>     325     330     335 | 1008 |
| gaa tca aca act cca act acg gaa gca aag ccg aca ata aca gaa gaa<br>Glu Ser Thr Thr Pro Thr Thr Glu Ala Lys Pro Thr Ile Thr Glu Glu<br>340     345     350 | 1056 |
| cca cta acc act gtt gca tct tct ata aat cca ccg caa cag caa gct<br>Pro Leu Thr Thr Val Ala Ser Ser Ile Asn Pro Pro Gln Gln Gln Ala<br>355     360     365 | 1104 |
| ccc gct aat aat caa aaa cca tgg gaa aaa tta gga att cca cag gaa<br>Pro Ala Asn Asn Gln Lys Pro Trp Glu Lys Leu Gly Ile Pro Gln Glu<br>370     375     380 | 1152 |
| atg tat aag gaa tct cta aaa gca gaa caa caa tta gcc aaa cca gta<br>Met Tyr Lys Glu Ser Leu Lys Ala Glu Gln Gln Leu Ala Lys Pro Val<br>385     390     395     400 | 1200 |
| ata gag cca aaa ccg cag gta cct gaa aaa aaa tca tca ctg gtt ata<br>Ile Glu Pro Lys Pro Gln Val Pro Glu Lys Lys Ser Ser Leu Val Ile<br>     405     410     415 | 1248 |
| aat act gaa gat caa gtt ggt gtt tat aat aca gga aat ata aaa caa<br>Asn Thr Glu Asp Gln Val Gly Val Tyr Asn Thr Gly Asn Ile Lys Gln<br>420     425     430 | 1296 |
| cct act tat tta tac act gaa gat gat ata aaa aat ata ttg gaa gca<br>Pro Thr Tyr Leu Tyr Thr Glu Asp Asp Ile Lys Asn Ile Leu Glu Ala | 1344 |

```
                435                 440                 445
aat ata gat aag aat atg ttc tct ata ttt cat cat gcc tct tta gaa    1392
Asn Ile Asp Lys Asn Met Phe Ser Ile Phe His His Ala Ser Leu Glu
        450                 455                 460 gag ccg gaa ata cta aaa gat act ctt cgt gtt aca gta gag gat tta    1440
Glu Pro Glu Ile Leu Lys Asp Thr Leu Arg Val Thr Val Glu Asp Leu
465                 470                 475                 480 ata cta gat aat aag cct gca att ata cca cta aat aca gga cat aaa    1488
Ile Leu Asp Asn Lys Pro Ala Ile Ile Pro Leu Asn Thr Gly His Lys
                485                 490                 495 cat tgg tta ctc tta atg gct agt aaa gat gat aaa ggt aat ata aac    1536
His Trp Leu Leu Leu Met Ala Ser Lys Asp Asp Lys Gly Asn Ile Asn
            500                 505                 510 ttt atg tat aat gat ccc tat ggt gag cca ttg gaa tct cga cca aaa    1584
Phe Met Tyr Asn Asp Pro Tyr Gly Glu Pro Leu Glu Ser Arg Pro Lys
        515                 520                 525 gta aca gaa tat att acc gaa att tat ccc gat gca aaa ata aca gac    1632
Val Thr Glu Tyr Ile Thr Glu Ile Tyr Pro Asp Ala Lys Ile Thr Asp
530                 535                 540 cta aat act aag caa caa gaa aat gta tat gat tgc gga gtg ttc gta    1680
Leu Asn Thr Lys Gln Gln Glu Asn Val Tyr Asp Cys Gly Val Phe Val
545                 550                 555                 560 tgc gat agt gcg atc aaa ctc tct aaa ggg caa aaa att cta act act    1728
Cys Asp Ser Ala Ile Lys Leu Ser Lys Gly Gln Lys Ile Leu Thr Thr
                565                 570                 575 gaa gaa tct aaa gac caa ggt ata aat tta agg aaa gct caa gct aat    1776
Glu Glu Ser Lys Asp Gln Gly Ile Asn Leu Arg Lys Ala Gln Ala Asn
            580                 585                 590 aca tta tta ata cag caa caa gca ata gcg att gga cac gaa tca cgc    1824
Thr Leu Leu Ile Gln Gln Gln Ala Ile Ala Ile Gly His Glu Ser Arg
        595                 600                 605 aag aca tca tct aca aat aac aaa ttt cac aat ctt att aac agc cga    1872
Lys Thr Ser Ser Thr Asn Asn Lys Phe His Asn Leu Ile Asn Ser Arg
610                 615                 620 aaa aca aaa gat act gaa agg agt cgt tga                           1902
Lys Thr Lys Asp Thr Glu Arg Ser Arg
625                 630
```

<210> SEQ ID NO 20
<211> LENGTH: 633
<212> TYPE: PRT
<213> ORGANISM: Rickettsia conorii

<400> SEQUENCE: 20

```
Met Ala Glu Ser Ile Ile Phe Thr Leu Leu Leu Gly Gly Glu Asp Arg
1               5                   10                  15

Ile Leu Glu Lys Ile Asn Lys Gln Glu Thr Gln Asn Lys Leu Pro Ile
            20                  25                  30

Ile Arg Leu Glu Val Asn Lys Ala Ser His Ile Pro Asp Lys Glu Arg
        35                  40                  45

Ile Phe Ser Glu Ile Leu Gln Glu Ser His Lys Lys Gly Lys Thr Pro
    50                  55                  60

Ile Phe Asn Ile Gln Leu Asn Asn Asn Ile Gln Pro Ile Phe Thr
65                  70                  75                  80

Val Gln Asp Leu Ile Asn Leu Gln Asn Leu Asn Ile Lys Thr Thr Ile
                85                  90                  95

Thr Phe Asp Gln Tyr Asn Ser Leu Pro Gln Asn Ser Glu Leu Glu Ala
            100                 105                 110
```

-continued

Tyr Trp Lys Gln Ile Met Lys Lys Val Asp His Val Phe Phe Thr Asn
            115                 120                 125

Glu Ala Asp Gln Asn Leu Ser Ile Ala Asp Gly Ile Val Pro Lys Asp
        130                 135                 140

Lys Ala Thr Thr Ile Thr Asp Ile Ser Leu Val Thr Ser Val Phe Asn
145                 150                 155                 160

Asn Leu Val Ser Asp Arg Lys Ile Asp Gln Leu Leu Ser Gly Thr Ile
                165                 170                 175

Pro Asp Lys Glu Lys Leu Asp Lys Ile Ile Lys Asn Ala Lys Asn Gln
            180                 185                 190

Gly Gly Arg Val Ile Ile Glu Thr Trp Pro Leu Ser Ala Asp Glu Ala
        195                 200                 205

Thr Asn Leu Ile Thr Ala Lys Phe Gly Ile Thr Ser Glu Asp Gln Ile
    210                 215                 220

Tyr Gly Leu Lys Leu Glu Ile Asn Glu Ile Leu Lys Asp Ala Asn Asn
225                 230                 235                 240

Ala Ala Glu Asn Leu Lys Lys Tyr Val Ser Gln Ile Ser Arg Gln Phe
                245                 250                 255

Gln Lys Asp Leu Gly Lys Thr Glu Val Asn Pro Ile Asp Phe Asn Phe
            260                 265                 270

Ile Asn Thr Lys Lys Val Ile Asn Asp Lys Pro Lys Asp Ile Gln Val
        275                 280                 285

Glu Gln Thr Ile Ser Tyr Glu Pro Leu Lys Ala Asn Gln Pro Gln Pro
    290                 295                 300

Gln Gly Phe Phe Lys Arg Ile Phe Asn Tyr Phe Lys Asp Ile Ile Thr
305                 310                 315                 320

Ser Phe Lys Glu Ala Ile Phe Gly Lys Lys Glu Glu Pro Lys Thr His
                325                 330                 335

Glu Ser Thr Thr Pro Thr Thr Glu Ala Lys Pro Thr Ile Thr Glu Glu
            340                 345                 350

Pro Leu Thr Thr Val Ala Ser Ser Ile Asn Pro Pro Gln Gln Gln Ala
        355                 360                 365

Pro Ala Asn Asn Gln Lys Pro Trp Glu Lys Leu Gly Ile Pro Gln Glu
    370                 375                 380

Met Tyr Lys Glu Ser Leu Lys Ala Glu Gln Gln Leu Ala Lys Pro Val
385                 390                 395                 400

Ile Glu Pro Lys Pro Gln Val Pro Glu Lys Lys Ser Ser Leu Val Ile
                405                 410                 415

Asn Thr Glu Asp Gln Val Gly Val Tyr Asn Thr Gly Asn Ile Lys Gln
            420                 425                 430

Pro Thr Tyr Leu Tyr Thr Glu Asp Asp Ile Lys Asn Ile Leu Glu Ala
        435                 440                 445

Asn Ile Asp Lys Asn Met Phe Ser Ile Phe His His Ala Ser Leu Glu
    450                 455                 460

Glu Pro Glu Ile Leu Lys Asp Thr Leu Arg Val Thr Val Glu Asp Leu
465                 470                 475                 480

Ile Leu Asp Asn Lys Pro Ala Ile Ile Pro Leu Asn Thr Gly His Lys
                485                 490                 495

His Trp Leu Leu Leu Met Ala Ser Lys Asp Asp Lys Gly Asn Ile Asn
            500                 505                 510

Phe Met Tyr Asn Asp Pro Tyr Gly Glu Pro Leu Glu Ser Arg Pro Lys
        515                 520                 525

Val Thr Glu Tyr Ile Thr Glu Ile Tyr Pro Asp Ala Lys Ile Thr Asp

Leu Asn Thr Lys Gln Gln Glu Asn Val Tyr Asp Cys Gly Val Phe Val
545                 550                 555                 560

Cys Asp Ser Ala Ile Lys Leu Ser Lys Gly Gln Lys Ile Leu Thr Thr
                565                 570                 575

Glu Glu Ser Lys Asp Gln Gly Ile Asn Leu Arg Lys Ala Gln Ala Asn
            580                 585                 590

Thr Leu Leu Ile Gln Gln Gln Ala Ile Ala Ile Gly His Glu Ser Arg
        595                 600                 605

Lys Thr Ser Ser Thr Asn Asn Lys Phe His Asn Leu Ile Asn Ser Arg
        610                 615                 620

Lys Thr Lys Asp Thr Glu Arg Ser Arg
625                 630

<210> SEQ ID NO 21

<400> SEQUENCE: 21

000

<210> SEQ ID NO 22
<211> LENGTH: 222
<212> TYPE: PRT
<213> ORGANISM: Candida albicans

<400> SEQUENCE: 22

Ser Lys Ile Lys Thr Leu Pro Ser Glu Gln Leu Asn Gln Val Leu Lys
1               5                   10                  15

Ile Trp Ser Thr Asn Ser Arg Gln Leu Ile Ile Glu Asn Tyr Leu Ile
                20                  25                  30

Glu Ile Tyr Thr His Asp Leu His Thr Leu Lys Asp Ser Asn Trp Leu
            35                  40                  45

Asn Asp Asn Ile Ile Asp Tyr Tyr Phe Asn Leu Ile Met Lys Ala Asn
        50                  55                  60

Pro Asn Val Phe Gly Trp Thr Thr His Phe Tyr Thr Thr Leu Val Gln
65                  70                  75                  80

Arg Gly Tyr Gln Gly Val Ala Arg Trp Ala Lys Arg Lys Ile Asn
                85                  90                  95

Val Phe Thr Met Glu Lys Ile Leu Thr Pro Ile Asn Ile Gly Asn Met
                100                 105                 110

His Trp Ala Leu Ala Val Ile Asp Asn Ile Lys Lys Thr Ile Thr Tyr
            115                 120                 125

Tyr Asp Ser Leu Gly Gly Thr His Asn Ser Gly Asn Pro Gln Ala Val
        130                 135                 140

Gln Thr Leu Ala His Tyr Met Lys Glu Glu Lys Arg Leu Gly Val
145                 150                 155                 160

Met Gly Asn Glu Tyr Lys Leu Ile Pro His Met Glu Ala Pro Gln Gln
                165                 170                 175

Lys Asn Gly Ser Asp Cys Gly Val Phe Thr Cys Thr Ala Ala Arg Tyr
            180                 185                 190

Ile Ser Ala Asn Lys Pro Leu Ser Tyr Ser Gln Asn Asp Met Lys Ile
        195                 200                 205

Ile Arg Arg Arg Met Val Tyr Glu Ile Leu Asp Asn Arg Leu
210                 215                 220

<210> SEQ ID NO 23

<211> LENGTH: 2767
<212> TYPE: DNA
<213> ORGANISM: Plasmodium falciparium
<220> FEATURE:
<221> NAME/KEY: CDS
<222> LOCATION: (2)..(1507)

<400> SEQUENCE: 23

```
a aaa caa gat atg gat aat atg aaa cct tca aaa agt agt gtt aga aat      49
  Lys Gln Asp Met Asp Asn Met Lys Pro Ser Lys Ser Ser Val Arg Asn
  1               5                  10                  15 ata aat act atc cag aat gat cat aat aaa gaa gac gaa ata atg ttc         97
Ile Asn Thr Ile Gln Asn Asp His Asn Lys Glu Asp Glu Ile Met Phe
             20                  25                  30 aaa aca cat aca cag aat cat aat tct aca gaa aaa tta tat tat gaa        145
Lys Thr His Thr Gln Asn His Asn Ser Thr Glu Lys Leu Tyr Tyr Glu
         35                  40                  45 cat att ttt gaa gaa ata aat aag cac aca aat gat aca caa cat ttc        193
His Ile Phe Glu Glu Ile Asn Lys His Thr Asn Asp Thr Gln His Phe
     50                  55                  60 aaa gaa aat aca tct aat gct gta aca aat gta att aag gac acg aac        241
Lys Glu Asn Thr Ser Asn Ala Val Thr Asn Val Ile Lys Asp Thr Asn
 65                  70                  75                  80 gaa aaa att aat aat ata gat aat cat ata aca aat aaa aat agt gat        289
Glu Lys Ile Asn Asn Ile Asp Asn His Ile Thr Asn Lys Asn Ser Asp
                 85                  90                  95 ata caa aat gaa aaa gat tca tat gtg gaa tat gat atg tct tct aat        337
Ile Gln Asn Glu Lys Asp Ser Tyr Val Glu Tyr Asp Met Ser Ser Asn
             100                 105                 110 aaa tgt gat caa aat gat tta tta aat atc acc act cct ata aca gac        385
Lys Cys Asp Gln Asn Asp Leu Leu Asn Ile Thr Thr Pro Ile Thr Asp
         115                 120                 125 cat gat act aat gat ctt cat aat att aat agt aat aac tat tca aca        433
His Asp Thr Asn Asp Leu His Asn Ile Asn Ser Asn Asn Tyr Ser Thr
     130                 135                 140 aat tta aac aaa gaa gaa gtt ttt aat gaa gaa gct att aaa gat aat        481
Asn Leu Asn Lys Glu Glu Val Phe Asn Glu Glu Ala Ile Lys Asp Asn
145                 150                 155                 160 gat ata tta aaa aaa tta aga tat gaa tat aaa aac tta att aat ata        529
Asp Ile Leu Lys Lys Leu Arg Tyr Glu Tyr Lys Asn Leu Ile Asn Ile
                 165                 170                 175 att gat tca ttt att gat gaa aca cta aat tat gat cta gat aaa aat        577
Ile Asp Ser Phe Ile Asp Glu Thr Leu Asn Tyr Asp Leu Asp Lys Asn
             180                 185                 190 tct cct gtt tct aaa tta cat tta gat gaa aaa aat gac aaa atg tgt        625
Ser Pro Val Ser Lys Leu His Leu Asp Glu Lys Asn Asp Lys Met Cys
         195                 200                 205 aat gaa agt aag gat cat ttt tta aat aat aaa aat aat ttt aaa gat        673
Asn Glu Ser Lys Asp His Phe Leu Asn Asn Lys Asn Asn Phe Lys Asp
     210                 215                 220 aat gat gct gat gaa gta tac aat aat ata gat gat gac tat aaa aat        721
Asn Asp Ala Asp Glu Val Tyr Asn Asn Ile Asp Asp Asp Tyr Lys Asn
225                 230                 235                 240 agc atg aaa ttt att gag gat act tca tca gaa gat aaa aat aaa tat        769
Ser Met Lys Phe Ile Glu Asp Thr Ser Ser Glu Asp Lys Asn Lys Tyr
                 245                 250                 255 gtt atc tta aaa tat gat gaa gac tcc tta att gaa gct tta gaa aaa        817
Val Ile Leu Lys Tyr Asp Glu Asp Ser Leu Ile Glu Ala Leu Glu Lys
             260                 265                 270 tta cga att gat aaa aaa aag aaa gat aaa cta ata aaa tta aaa gag        865
Leu Arg Ile Asp Lys Lys Lys Lys Asp Lys Leu Ile Lys Leu Lys Glu
```

```
                    275                 280                 285
aaa tat cca gag gat ata gaa aaa gat gca tat gat gat gaa acc aaa      913
Lys Tyr Pro Glu Asp Ile Glu Lys Asp Ala Tyr Asp Asp Glu Thr Lys
    290                 295                 300 aaa aaa aaa att gat aaa aat ata ttt ttt aaa tgt agt aaa aaa gaa      961
Lys Lys Lys Ile Asp Lys Asn Ile Phe Phe Lys Cys Ser Lys Lys Glu
305                 310                 315                 320 tac tat gaa aaa gct ata att ata tta aat gaa aaa att gaa aat cga     1009
Tyr Tyr Glu Lys Ala Ile Ile Ile Leu Asn Glu Lys Ile Glu Asn Arg
                325                 330                 335 gtt tta att gaa aaa ttt aat gta ccc tta tta tat tca caa att aaa     1057
Val Leu Ile Glu Lys Phe Asn Val Pro Leu Leu Tyr Ser Gln Ile Lys
            340                 345                 350 tgt ctt ata gat acc aga tgg tta aat gac gaa gtc att aat ttc tat     1105
Cys Leu Ile Asp Thr Arg Trp Leu Asn Asp Glu Val Ile Asn Phe Tyr
        355                 360                 365 cta agt atg tta caa gaa tat aat gaa caa cat aca aaa aat aat tct     1153
Leu Ser Met Leu Gln Glu Tyr Asn Glu Gln His Thr Lys Asn Asn Ser
    370                 375                 380 ctt aca ttt ata ccg aaa att ttt act ttt agt act ttt ttt ttt caa     1201
Leu Thr Phe Ile Pro Lys Ile Phe Thr Phe Ser Thr Phe Phe Phe Gln
385                 390                 395                 400 tct tta aat ttt aat gga tca tat aat tat agc aaa gtc tca aga tgg     1249
Ser Leu Asn Phe Asn Gly Ser Tyr Asn Tyr Ser Lys Val Ser Arg Trp
                405                 410                 415 acc aaa aga aaa caa gtt gat ata ttt tct ttc gat tta att ctt ata     1297
Thr Lys Arg Lys Gln Val Asp Ile Phe Ser Phe Asp Leu Ile Leu Ile
            420                 425                 430 ccc tta cac gtg ggt gga aac cat tgg act ctt ggt tct atc cat atg     1345
Pro Leu His Val Gly Gly Asn His Trp Thr Leu Gly Ser Ile His Met
        435                 440                 445 aaa gac aaa aaa ata tgt tta tat gat tct ttg aat gga tca aat aaa     1393
Lys Asp Lys Lys Ile Cys Leu Tyr Asp Ser Leu Asn Gly Ser Asn Lys
    450                 455                 460 aag ttt ttt gaa tat atg aga aga tat ata gtt gat gaa atg aag gat     1441
Lys Phe Phe Glu Tyr Met Arg Arg Tyr Ile Val Asp Glu Met Lys Asp
465                 470                 475                 480 aaa aaa caa aag gat ttg gac ata tcc tta tgg act tat agt aaa gag     1489
Lys Lys Gln Lys Asp Leu Asp Ile Ser Leu Trp Thr Tyr Ser Lys Glu
                485                 490                 495 ggc gtt tct gag gta tct taatatataa aaagactgaa taaatgaaat            1537
Gly Val Ser Glu Val Ser
            500 aatgaacgaa cgtttaattg tatgatgtat ataaatatta ttatatatat gtatatgtat   1597 atatatatgt atatatgtgt atatgtatat atgtgtatat gtatatatgt gtgtatattt   1657 tatagaaagg aattccgcat caggagaatg gatatgattg tggtgtgttt acgtgtatgt   1717 ttgcaaagtg tttaagtttt aaccgggaat ttgattttaa tcaaagagat ataaaggaca   1777 ttcgattaaa aatggtataa aaataaaaca catatatata tatatatatg tgtatgcata   1837 atatttatgt gttatattac ataacattca actttaatat atataatata tatgttttc   1897 tttttataga cttatgagat atctcaaggt tgtttagtat tttaattata gacaactctt   1957 tttctaaact atttttatttt tattccccat atttttatta ttttaaatta tgaattttt   2017 tttttttttt ttatgggtta aatactatat attttttac atttctataa tatataaaag    2077 tattattaat ttttattata taatatataa atatattata tattatatat attatatata   2137 tttcatttca tttcactttta tttaatttaa tttaatttaa ttggtttttt tttttttttt  2197
```

-continued

```
tttttttttt aaaaagaaaa cattatttg aatatcataa agaatatttt aaaatatatg      2257
tataacttaa ttttataat tatttatggc ctaacaaata aatatattaa gttatttaaa      2317
tttaatatta tacaaattca tgggtacaaa caaacatata tcaagtttaa atttgaaaca      2377
taaaaatggg ataaaaaaaa aaaaatttat aacaaaaatg taaatacata catatatata     2437
tatatatatc tatttatttt aatatccttg tatattttg ataagaaact tttaataaat     2497
ttatattttc ttttcataac tttaataaaa agataatttg ttattattct ttaaacaaga     2557
taaatatgca acttcacaac cataatcgta aagaatatct cctttattct tgttcataat     2617
atcatgttca aatatacatt ttttcagctt actactaatt gtatttaagt cctgaaaaaa     2677
aataaaaata aaaataaaat aaaataaaat aaaaaaataa aataaaaaaa taaaataaaa     2737
aaataaaata aaataaaaaa aaaaaaaaaa                                      2767
```

<210> SEQ ID NO 24
<211> LENGTH: 502
<212> TYPE: PRT
<213> ORGANISM: Plasmodium falciparium

<400> SEQUENCE: 24

```
Lys Gln Asp Met Asp Asn Met Lys Pro Ser Lys Ser Ser Val Arg Asn
1               5                   10                  15

Ile Asn Thr Ile Gln Asn Asp His Asn Lys Glu Asp Glu Ile Met Phe
            20                  25                  30

Lys Thr His Thr Gln Asn His Asn Ser Thr Glu Lys Leu Tyr Tyr Glu
        35                  40                  45

His Ile Phe Glu Glu Ile Asn Lys His Thr Asn Asp Thr Gln His Phe
    50                  55                  60

Lys Glu Asn Thr Ser Asn Ala Val Thr Asn Val Ile Lys Asp Thr Asn
65                  70                  75                  80

Glu Lys Ile Asn Asn Ile Asp Asn His Ile Thr Asn Lys Asn Ser Asp
                85                  90                  95

Ile Gln Asn Glu Lys Asp Ser Tyr Val Glu Tyr Asp Met Ser Ser Asn
            100                 105                 110

Lys Cys Asp Gln Asn Asp Leu Leu Asn Ile Thr Thr Pro Ile Thr Asp
        115                 120                 125

His Asp Thr Asn Asp Leu His Asn Ile Asn Ser Asn Asn Tyr Ser Thr
    130                 135                 140

Asn Leu Asn Lys Glu Glu Val Phe Asn Glu Ala Ile Lys Asp Asn
145                 150                 155                 160

Asp Ile Leu Lys Lys Leu Arg Tyr Glu Tyr Lys Asn Leu Ile Asn Ile
                165                 170                 175

Ile Asp Ser Phe Ile Asp Glu Thr Leu Asn Tyr Asp Leu Asp Lys Asn
            180                 185                 190

Ser Pro Val Ser Lys Leu His Leu Asp Glu Lys Asn Asp Lys Met Cys
        195                 200                 205

Asn Glu Ser Lys Asp His Phe Leu Asn Asn Lys Asn Asn Phe Lys Asp
    210                 215                 220

Asn Asp Ala Asp Glu Val Tyr Asn Asn Ile Asp Asp Tyr Lys Asn
225                 230                 235                 240

Ser Met Lys Phe Ile Glu Asp Thr Ser Ser Glu Asp Lys Asn Lys Tyr
                245                 250                 255

Val Ile Leu Lys Tyr Asp Glu Asp Ser Leu Ile Glu Ala Leu Glu Lys
            260                 265                 270
```

```
Leu Arg Ile Asp Lys Lys Lys Asp Lys Leu Ile Lys Leu Lys Glu
        275                 280                 285

Lys Tyr Pro Glu Asp Ile Glu Lys Asp Ala Tyr Asp Asp Glu Thr Lys
        290                 295                 300

Lys Lys Lys Ile Asp Lys Asn Ile Phe Phe Lys Cys Ser Lys Lys Glu
305                 310                 315                 320

Tyr Tyr Glu Lys Ala Ile Ile Ile Leu Asn Glu Lys Ile Glu Asn Arg
                325                 330                 335

Val Leu Ile Glu Lys Phe Asn Val Pro Leu Leu Tyr Ser Gln Ile Lys
            340                 345                 350

Cys Leu Ile Asp Thr Arg Trp Leu Asn Asp Glu Val Ile Asn Phe Tyr
        355                 360                 365

Leu Ser Met Leu Gln Glu Tyr Asn Glu Gln His Thr Lys Asn Asn Ser
    370                 375                 380

Leu Thr Phe Ile Pro Lys Ile Phe Thr Phe Ser Thr Phe Phe Phe Gln
385                 390                 395                 400

Ser Leu Asn Phe Asn Gly Ser Tyr Asn Tyr Ser Lys Val Ser Arg Trp
                405                 410                 415

Thr Lys Arg Lys Gln Val Asp Ile Phe Ser Phe Asp Leu Ile Leu Ile
            420                 425                 430

Pro Leu His Val Gly Gly Asn His Trp Thr Leu Gly Ser Ile His Met
        435                 440                 445

Lys Asp Lys Lys Ile Cys Leu Tyr Asp Ser Leu Asn Gly Ser Asn Lys
    450                 455                 460

Lys Phe Phe Glu Tyr Met Arg Arg Tyr Ile Val Asp Glu Met Lys Asp
465                 470                 475                 480

Lys Lys Gln Lys Asp Leu Asp Ile Ser Leu Trp Thr Tyr Ser Lys Glu
                485                 490                 495

Gly Val Ser Glu Val Ser
            500

<210> SEQ ID NO 25
<211> LENGTH: 604
<212> TYPE: DNA
<213> ORGANISM: Trypanosoma brucei
<220> FEATURE:
<221> NAME/KEY: CDS
<222> LOCATION: (2)..(604)

<400> SEQUENCE: 25 t ttt gag aca act cta acg acg ggc aaa tgg gat agc tcg cga tct cag      49
  Phe Glu Thr Thr Leu Thr Thr Gly Lys Trp Asp Ser Ser Arg Ser Gln
  1               5                   10                  15 aac tct ggt gag cag gag agg gtt gct gtg tca ctc aag agc gga ata        97
Asn Ser Gly Glu Gln Glu Arg Val Ala Val Ser Leu Lys Ser Gly Ile
            20                  25                  30 gca ata acg tac cgg cag ttg tcg aca ttg gca cca ggc gtg tgg tta       145
Ala Ile Thr Tyr Arg Gln Leu Ser Thr Leu Ala Pro Gly Val Trp Leu
        35                  40                  45 aac gac caa att atc aac gcc tac ctg gga cta att tgt gac gag tat       193
Asn Asp Gln Ile Ile Asn Ala Tyr Leu Gly Leu Ile Cys Asp Glu Tyr
    50                  55                  60 aat gtg agg gct ggc tgt gaa gct gcg gtg tct atg ggg aca cat ttc       241
Asn Val Arg Ala Gly Cys Glu Ala Ala Val Ser Met Gly Thr His Phe
65                  70                  75                  80 tat gcc aaa gta cag caa gag atg cga ata gga aat gcc ggt ttg aac       289
Tyr Ala Lys Val Gln Gln Glu Met Arg Ile Gly Asn Ala Gly Leu Asn
```

```
ccc tcg tcg ggc gga ttc cca act ctt gag caa aac agt ggt gtc ctc    337
Pro Ser Ser Gly Gly Phe Pro Thr Leu Glu Gln Asn Ser Gly Val Leu
            100                 105                 110 cgt tgg ctg aaa agg cgt cgg cat atc ttg caa tcg ggt acc acc cgc    385
Arg Trp Leu Lys Arg Arg Arg His Ile Leu Gln Ser Gly Thr Thr Arg
            115                 120                 125 att gtg ctt gtg cct gtc aac ttg tgg cag tcg cac tgg aca ctt gcc    433
Ile Val Leu Val Pro Val Asn Leu Trp Gln Ser His Trp Thr Leu Ala
    130                 135                 140 gta ctt gat tgg gaa cga aac aga tgg aca tat tac gac agt ttg ctg    481
Val Leu Asp Trp Glu Arg Asn Arg Trp Thr Tyr Tyr Asp Ser Leu Leu
145                 150                 155                 160 tac gga aat gcc cct gtg cca cag gga agt act gtg ctt ggg gcg ctt    529
Tyr Gly Asn Ala Pro Val Pro Gln Gly Ser Thr Val Leu Gly Ala Leu
                165                 170                 175 cac cac aca ttt gaa gaa gcg cgg cgt att ttg tgt gat agt gac gat    577
His His Thr Phe Glu Glu Ala Arg Arg Ile Leu Cys Asp Ser Asp Asp
                180                 185                 190 gct aat agc aat cat acc gtt aag gct                                604
Ala Asn Ser Asn His Thr Val Lys Ala
            195                 200

<210> SEQ ID NO 26
<211> LENGTH: 201
<212> TYPE: PRT
<213> ORGANISM: Trypanosoma brucei

<400> SEQUENCE: 26

Phe Glu Thr Thr Leu Thr Thr Gly Lys Trp Asp Ser Ser Arg Ser Gln
1               5                   10                  15

Asn Ser Gly Glu Gln Glu Arg Val Ala Val Ser Leu Lys Ser Gly Ile
            20                  25                  30

Ala Ile Thr Tyr Arg Gln Leu Ser Thr Leu Ala Pro Gly Val Trp Leu
        35                  40                  45

Asn Asp Gln Ile Ile Asn Ala Tyr Leu Gly Leu Ile Cys Asp Glu Tyr
    50                  55                  60

Asn Val Arg Ala Gly Cys Glu Ala Ala Val Ser Met Gly Thr His Phe
65                  70                  75                  80

Tyr Ala Lys Val Gln Gln Glu Met Arg Ile Gly Asn Ala Gly Leu Asn
                85                  90                  95

Pro Ser Ser Gly Gly Phe Pro Thr Leu Glu Gln Asn Ser Gly Val Leu
            100                 105                 110

Arg Trp Leu Lys Arg Arg Arg His Ile Leu Gln Ser Gly Thr Thr Arg
            115                 120                 125

Ile Val Leu Val Pro Val Asn Leu Trp Gln Ser His Trp Thr Leu Ala
    130                 135                 140

Val Leu Asp Trp Glu Arg Asn Arg Trp Thr Tyr Tyr Asp Ser Leu Leu
145                 150                 155                 160

Tyr Gly Asn Ala Pro Val Pro Gln Gly Ser Thr Val Leu Gly Ala Leu
                165                 170                 175

His His Thr Phe Glu Glu Ala Arg Arg Ile Leu Cys Asp Ser Asp Asp
                180                 185                 190

Ala Asn Ser Asn His Thr Val Lys Ala
            195                 200

<210> SEQ ID NO 27
```

<211> LENGTH: 229
<212> TYPE: PRT
<213> ORGANISM: Eschericia coli

<400> SEQUENCE: 27

```
Gly Asp Glu Ile Pro Leu Ile Ser Glu Lys Gln Ser Leu Ser Lys Val
1               5                   10                  15

Leu Leu Asn Asp Glu Asn Asn Glu Leu Ser Asp Gly Thr Asn Phe Trp
                20                  25                  30

Asp Lys Asn Arg Gln Leu Thr Thr Asp Glu Ile Ala Cys Tyr Leu Gln
            35                  40                  45

Lys Ile Ala Ala Asn Ala Lys Asn Thr Gln Val Asn Tyr Pro Thr Gly
        50                  55                  60

Leu Tyr Val Pro Tyr Ser Thr Arg Thr His Leu Glu Asp Ala Leu Asn
65                  70                  75                  80

Glu Asn Ile Lys Ser Asp Pro Ser Trp Pro Asn Glu Val Gln Leu Phe
                85                  90                  95

Pro Ile Asn Thr Gly Gly His Trp Ile Leu Val Ser Leu Gln Lys Ile
                100                 105                 110

Val Asn Lys Lys Asn Asn Lys Leu Gln Ile Lys Cys Val Ile Phe Asn
            115                 120                 125

Ser Leu Arg Ala Leu Gly Tyr Asp Lys Glu Asn Ser Leu Lys Arg Val
130                 135                 140

Ile Asn Ser Phe Asn Ser Glu Leu Met Gly Glu Met Ser Asn Asn Asn
145                 150                 155                 160

Ile Lys Val His Leu Asn Glu Pro Glu Ile Ile Phe Leu His Ala Asp
                165                 170                 175

Leu Gln Gln Tyr Leu Ser Gln Ser Cys Gly Ala Phe Val Cys Met Ala
            180                 185                 190

Ala Gln Glu Val Ile Glu Gln Arg Ser Asn Ser Asp Ser Ala Pro
        195                 200                 205

Tyr Thr Leu Leu Lys Asn His Ala Asp Arg Phe Lys Lys Tyr Ser Ala
210                 215                 220

Glu Glu Gln Tyr Glu
225
```

<210> SEQ ID NO 28
<211> LENGTH: 207
<212> TYPE: PRT
<213> ORGANISM: Salmonella paratyphi

<400> SEQUENCE: 28

```
Gly Ser Ala Thr Thr Asp Leu Ser Lys Lys Ile Gly Ile Ala His Lys
1               5                   10                  15

Ile Met Gly Asp Gln Phe Ala Gln Thr Asp Gln Glu Gln Val Gly Val
                20                  25                  30

Glu Asn Leu Trp Cys Ser Ala Arg Met Leu Ser Ser Asp Glu Leu Ala
            35                  40                  45

Ala Ala Thr Leu Gly Leu Val Gln Glu Ser Pro Leu Leu Ser Val Asn
        50                  55                  60

Tyr Pro Ile Gly Leu Ile His Pro Thr Lys Glu Asn Ile Leu Arg
65                  70                  75                  80

Thr Gln Leu Leu Glu Lys Met Ala Gln Ser Gly Leu Ser Glu Asn Glu
                85                  90                  95

Val Phe Leu Ile Asn Thr Gly Asp His Trp Leu Ile Cys Leu Phe Tyr
                100                 105                 110
```

Lys Leu Ala Glu Lys Ile Lys Cys Leu Ile Phe Asn Thr Tyr His Asp
            115                 120                 125

Leu Asn Glu Asn Thr Lys Gln Glu Ile Ile Glu Ala Ala Lys Ile Thr
        130                 135                 140

Gly Ile Ser Glu Asn Glu Asp Ile Asp Phe Ile Glu Thr Asn Leu Gln
145                 150                 155                 160

Asn Asn Val Pro Asn Gly Cys Gly Leu Phe Cys Tyr His Thr Ile Gln
                165                 170                 175

Leu Leu Ser Asn Ala Gly Gln Asn Asp Pro Ala Thr Thr Leu Arg Glu
            180                 185                 190

Phe Ala Glu Asn Phe Leu Thr Leu Ser Val Glu Glu Gln Thr Leu
            195                 200                 205

<210> SEQ ID NO 29
<211> LENGTH: 207
<212> TYPE: PRT
<213> ORGANISM: Salmonella enteriditis

<400> SEQUENCE: 29

Gly Ser Ala Thr Thr Asp Leu Ser Lys Lys Ile Gly Ile Ala His Lys
1               5                   10                  15

Ile Met Gly Asp Gln Phe Ala Gln Thr Asp Gln Glu Gln Val Gly Val
            20                  25                  30

Glu Asn Leu Trp Cys Gly Ala Arg Met Leu Ser Ser Asp Glu Leu Ala
        35                  40                  45

Ala Ala Thr Gln Gly Leu Val Gln Glu Ser Pro Leu Leu Ser Val Asn
    50                  55                  60

Tyr Pro Ile Gly Leu Ile His Pro Thr Thr Lys Glu Asn Ile Leu Ser
65                  70                  75                  80

Thr Gln Leu Leu Glu Lys Ile Ala Gln Ser Gly Leu Ser His Asn Glu
                85                  90                  95

Val Phe Leu Val Asn Thr Gly Asp His Trp Leu Leu Cys Leu Phe Tyr
            100                 105                 110

Lys Leu Ala Glu Lys Ile Lys Cys Leu Ile Phe Asn Thr Tyr Tyr Asp
            115                 120                 125

Leu Asn Glu Asn Thr Lys Gln Glu Ile Ile Glu Ala Ala Lys Ile Ala
        130                 135                 140

Gly Ile Ser Glu Asn Glu Asn Ile Asp Phe Ile Glu Thr Asn Leu Gln
145                 150                 155                 160

Asn Asn Val Pro Asn Gly Cys Gly Leu Phe Cys Tyr His Ala Ile Gln
                165                 170                 175

Leu Leu Ser Asn Ala Gly Gln Asn Asp Pro Ala Thr Thr Leu Arg Glu
            180                 185                 190

Phe Ala Glu Asn Phe Leu Thr Leu Ser Val Glu Glu Gln Thr Leu
            195                 200                 205

<210> SEQ ID NO 30
<211> LENGTH: 207
<212> TYPE: PRT
<213> ORGANISM: Salmonella typhimurium

<400> SEQUENCE: 30

Gly Ser Ala Thr Thr Asp Leu Ser Lys Lys Ile Gly Ile Ala His Lys
1               5                   10                  15

Ile Met Gly Asp Gln Phe Ala Gln Thr Asp Gln Glu Gln Val Gly Val
            20                  25                  30

```
Glu Asn Leu Trp Cys Gly Ala Arg Met Leu Ser Ser Asp Glu Leu Ala
             35                  40                  45

Ala Ala Thr Gln Gly Leu Val Gln Glu Ser Pro Leu Leu Ser Val Asn
 50                  55                  60

Tyr Pro Ile Gly Leu Ile His Pro Thr Thr Lys Glu Asn Ile Leu Ser
 65                  70                  75                  80

Thr Gln Leu Leu Glu Lys Ile Ala Gln Ser Gly Leu Ser His Asn Glu
                 85                  90                  95

Val Phe Leu Val Asn Thr Gly Asp His Trp Leu Leu Cys Leu Phe Tyr
                100                 105                 110

Lys Leu Ala Glu Lys Ile Lys Cys Leu Ile Phe Asn Thr Tyr Tyr Asp
                115                 120                 125

Leu Asn Glu Asn Thr Lys Gln Glu Ile Ile Glu Ala Ala Lys Ile Ala
                130                 135                 140

Gly Ile Ser Glu Ser Asp Glu Val Asn Phe Ile Glu Met Asn Leu Gln
145                 150                 155                 160

Asn Asn Val Pro Asn Gly Cys Gly Leu Phe Cys Tyr His Thr Ile Gln
                165                 170                 175

Leu Leu Ser Asn Ala Gly Gln Asn Asp Pro Ala Thr Thr Leu Arg Glu
                180                 185                 190

Phe Ala Glu Asn Phe Leu Thr Leu Ser Val Glu Glu Gln Ala Leu
                195                 200                 205

<210> SEQ ID NO 31
<211> LENGTH: 207
<212> TYPE: PRT
<213> ORGANISM: Salmonella typhi

<400> SEQUENCE: 31

Gly Ser Ala Thr Thr Asp Leu Ser Lys Lys Ile Gly Ile Ala His Lys
 1                5                  10                  15

Ile Met Gly Asp Gln Phe Ala Gln Thr Asp Gln Glu Gln Val Gly Val
                 20                  25                  30

Glu Asn Leu Trp Cys Ser Ala Arg Met Leu Ser Ser Asp Glu Leu Ala
             35                  40                  45

Ala Ala Thr Leu Gly Leu Val Gln Glu Ser Pro Leu Leu Ser Val Asn
 50                  55                  60

Tyr Pro Ile Gly Leu Ile His Pro Thr Thr Lys Glu Asn Ile Leu Arg
 65                  70                  75                  80

Thr Gln Leu Leu Glu Lys Met Ala Gln Ser Gly Leu Ser Glu Asn Glu
                 85                  90                  95

Val Phe Leu Ile Asn Thr Gly Asp His Trp Leu Ile Cys Leu Phe Tyr
                100                 105                 110

Lys Leu Ala Glu Lys Ile Lys Cys Leu Ile Phe Asn Thr Tyr His Asp
                115                 120                 125

Leu Asn Glu Asn Thr Lys Gln Glu Ile Ile Glu Ala Ala Lys Ile Thr
                130                 135                 140

Gly Ile Ser Glu Asn Glu Asp Ile Asp Phe Ile Glu Thr Asn Leu Gln
145                 150                 155                 160

Asn Asn Val Pro Asn Gly Cys Gly Leu Phe Cys Tyr His Thr Ile Gln
                165                 170                 175

Leu Leu Ser Asn Ala Gly Gln Asn Asp Pro Ala Thr Thr Leu Arg Glu
                180                 185                 190

Phe Ala Glu Asn Phe Leu Thr Leu Ser Val Glu Glu Gln Thr Leu
```

<210> SEQ ID NO 32
<211> LENGTH: 185
<212> TYPE: PRT
<213> ORGANISM: Pseudomonas syringae

<400> SEQUENCE: 32

Ala Leu Pro Pro Met Ser Pro Glu Arg Ile Asp Val Asp Asn Leu Pro
1               5                   10                  15

Phe Pro Gln Asp Val Glu Asp Pro Glu Leu Pro Gln Val Thr Glu Thr
            20                  25                  30

Ser Trp Leu Leu Asp Gly His Leu His Ala Tyr Thr Asn Asp Leu Ala
        35                  40                  45

Arg Arg Leu Gln Glu Glu Ser Asn Ala His Leu Leu His Phe Ala Asp
50                  55                  60

Ser Gln Ile Val Thr Met Leu Asn Ser Glu Asp Glu Ala Gln Arg Asn
65                  70                  75                  80

Val Ala Leu Arg Arg Leu Val Gly Asp Ala Val Asn Pro Ala Pro Pro
                85                  90                  95

Ile Ala Phe Met Pro Ile Asn Arg Asp Asn Val His Trp Ser Leu Leu
            100                 105                 110

Val Val Asp Arg Arg Asp Asn His Ser Pro Ala Ala Tyr His Tyr Asp
        115                 120                 125

Ser Met Gly Thr Pro His Pro His Gln His Trp His Ala Gln Met Ala
130                 135                 140

Ala Trp Arg Leu Gly Leu Asp Ala Ser Gln Val Tyr Lys Met Pro Thr
145                 150                 155                 160

Ala Ile Gln Pro Asp Gly Tyr Ser Cys Gly Asp His Val Leu Thr Gly
                165                 170                 175

Ile Glu Val Leu Ala His Arg Val Ile
            180                 185

<210> SEQ ID NO 33
<211> LENGTH: 96
<212> TYPE: PRT
<213> ORGANISM: Chlamydia trachomatis

<400> SEQUENCE: 33

Ser His Trp Leu Leu Val Ile Val Asp Ile Gln Ala Arg Arg Leu Val
1               5                   10                  15

Tyr Phe Asp Ser Leu Tyr Asn Tyr Val Met Ser Pro Glu Asp Met Glu
            20                  25                  30

Lys Asp Leu Gln Ser Phe Ala Gln Gln Leu Asp Gln Val Tyr Pro Ala
        35                  40                  45

Tyr Asp Ser Gln Lys Phe Ser Val Lys Ile Ala Ala Lys Glu Val Ile
50                  55                  60

Gln Lys Gly Ser Gly Ser Ser Cys Gly Ala Trp Cys Cys Gln Phe Leu
65                  70                  75                  80

His Trp Tyr Leu Arg Asp Pro Phe Thr Asp Ala Leu Asn Asp Leu Pro
                85                  90                  95

<210> SEQ ID NO 34
<211> LENGTH: 97
<212> TYPE: PRT
<213> ORGANISM: Chlamydia muridarum

<400> SEQUENCE: 34

```
Ser His Trp Thr Val Ile Val Asp Leu Asp Ala Arg Cys Ile Thr
1               5                   10                  15

Tyr Phe Asp Ser Leu Val Asn Tyr Ile Ala Ser Thr Asp Glu Met Glu
                20                  25                  30

Arg Arg Met Lys Ser Leu Ala Cys Cys Leu Ala Asn Ile Gly Leu Cys
            35                  40                  45

Lys Asn Asn Gly Cys Pro Phe Asp Val His Val Ala Val Asn Glu Ser
50                      55                  60

Leu Gln Asn Trp Met Gly Ser Cys Cys Gly Leu Trp Cys Cys Gln Tyr
65                  70                  75                  80

Met Lys Trp Tyr Met Asp His Ser His Thr Gly Ile Leu Gln Lys Ile
                85                  90                  95

Pro
```

<210> SEQ ID NO 35
<211> LENGTH: 155
<212> TYPE: PRT
<213> ORGANISM: Mesorhizobium loti

<400> SEQUENCE: 35

```
Thr Gln Leu Leu Gly Asp Glu His Ile Gln Arg Asp Tyr Glu Phe Leu
1               5                   10                  15

Glu Gln Gln Leu Gln Gln Ala Asp Pro Ala Leu Ala Ala Arg Thr Arg
                20                  25                  30

Leu Val Asp Pro Ser Val Ser His Leu Leu Arg His Met Glu Gln Gln
            35                  40                  45

Asp Ala Arg Gly Thr Leu Gln Ser Ile Tyr Asn Arg Asn Ala Gly Pro
50                  55                  60

Ser Asp Phe Leu Phe Val Pro Val Asn Asp Gly Val Gly Ile Asp Arg
65                  70                  75                  80

Gly Thr His Trp Ser Leu Leu Val Asp Arg Arg Asp Pro Glu Arg
                85                  90                  95

Ala Val Ala Tyr His Tyr Asp Ser Ile Gln Gln Asn Glu Gln Arg Tyr
                100                 105                 110

Asn Asp Ala Pro Ala Arg Lys Leu Ala Thr Arg Leu Asp Ala Thr Leu
            115                 120                 125

Val Thr Pro Asp Met Ala Gln Gln Lys Asn Ala Val Asp Cys Gly Val
130                 135                 140

Phe Val Val Asp Gly Thr Arg Glu Leu Val Arg
145                 150                 155
```

<210> SEQ ID NO 36
<211> LENGTH: 215
<212> TYPE: PRT
<213> ORGANISM: Rickettsia conorii

<400> SEQUENCE: 36

```
Glu Met Tyr Lys Glu Ser Leu Lys Ala Glu Gln Gln Leu Ala Lys Pro
1               5                   10                  15

Val Ile Glu Pro Lys Pro Gln Val Pro Glu Lys Lys Ser Ser Leu Val
                20                  25                  30

Ile Asn Thr Glu Asp Gln Val Gly Val Tyr Asn Thr Gly Asn Ile Lys
            35                  40                  45

Gln Pro Thr Tyr Leu Tyr Thr Glu Asp Asp Ile Lys Asn Ile Leu Glu
50                  55                  60
```

```
Ala Asn Ile Asp Lys Asn Met Phe Ser Ile Phe His His Ala Ser Leu
 65                  70                  75                  80

Glu Glu Pro Glu Ile Leu Lys Asp Thr Leu Arg Val Thr Val Glu Asp
                 85                  90                  95

Leu Ile Leu Asp Asn Lys Pro Ala Ile Ile Pro Leu Asn Thr Gly His
            100                 105                 110

Lys His Trp Leu Leu Leu Met Ala Ser Lys Asp Asp Lys Gly Asn Ile
        115                 120                 125

Asn Phe Met Tyr Asn Asp Pro Tyr Gly Glu Pro Leu Glu Ser Arg Pro
130                 135                 140

Lys Val Thr Glu Tyr Ile Thr Glu Ile Tyr Pro Asp Ala Lys Ile Thr
145                 150                 155                 160

Asp Leu Asn Thr Lys Gln Gln Glu Asn Val Tyr Asp Cys Gly Val Phe
                165                 170                 175

Val Cys Asp Ser Ala Ile Lys Leu Ser Lys Gly Gln Lys Ile Leu Thr
            180                 185                 190

Thr Glu Glu Ser Lys Asp Gln Gly Ile Asn Leu Arg Lys Ala Gln Ala
        195                 200                 205

Asn Thr Leu Leu Ile Gln Gln
    210                 215
```

<210> SEQ ID NO 37
<211> LENGTH: 222
<212> TYPE: PRT
<213> ORGANISM: Candida albicans

<400> SEQUENCE: 37

```
Ser Lys Ile Lys Thr Leu Pro Ser Glu Gln Leu Asn Gln Val Leu Lys
  1               5                  10                  15

Ile Trp Ser Thr Asn Ser Arg Gln Leu Ile Ile Glu Asn Tyr Leu Ile
                 20                  25                  30

Glu Ile Tyr Thr His Asp Leu His Thr Leu Lys Asp Ser Asn Trp Leu
             35                  40                  45

Asn Asp Asn Ile Ile Asp Tyr Tyr Phe Asn Leu Ile Met Lys Ala Asn
 50                  55                  60

Pro Asn Val Phe Gly Trp Thr Thr His Phe Tyr Thr Thr Leu Val Gln
 65                  70                  75                  80

Arg Gly Tyr Gln Gly Val Ala Arg Trp Ala Lys Arg Lys Lys Ile Asn
                 85                  90                  95

Val Phe Thr Met Glu Lys Ile Leu Thr Pro Ile Asn Ile Gly Asn Met
            100                 105                 110

His Trp Ala Leu Ala Val Ile Asp Asn Ile Lys Lys Thr Ile Thr Tyr
        115                 120                 125

Tyr Asp Ser Leu Gly Gly Thr His Asn Ser Gly Asn Pro Gln Ala Val
130                 135                 140

Gln Thr Leu Ala His Tyr Met Lys Glu Glu Ala Lys Arg Leu Gly Val
145                 150                 155                 160

Met Gly Asn Glu Tyr Lys Leu Ile Pro His Met Glu Ala Pro Gln Gln
                165                 170                 175

Lys Asn Gly Ser Asp Cys Gly Val Phe Thr Cys Thr Ala Ala Arg Tyr
            180                 185                 190

Ile Ser Ala Asn Lys Pro Leu Ser Tyr Ser Gln Asn Asp Met Lys Ile
        195                 200                 205

Ile Arg Arg Arg Met Val Tyr Glu Ile Leu Asp Asn Arg Leu
210                 215                 220
```

<210> SEQ ID NO 38
<211> LENGTH: 155
<212> TYPE: PRT
<213> ORGANISM: Plasmodium falciparium

<400> SEQUENCE: 38

```
Glu Asn Arg Val Leu Ile Glu Lys Phe Asn Val Pro Leu Leu Tyr Ser
1               5                   10                  15

Gln Ile Lys Cys Leu Ile Asp Thr Arg Trp Leu Asn Asp Glu Val Ile
            20                  25                  30

Asn Phe Tyr Leu Ser Met Leu Gln Glu Tyr Asn Glu Gln His Thr Lys
        35                  40                  45

Asn Asn Ser Leu Thr Phe Ile Pro Lys Ile Phe Thr Phe Ser Thr Phe
    50                  55                  60

Phe Phe Gln Ser Leu Asn Phe Asn Gly Ser Tyr Asn Tyr Ser Lys Val
65                  70                  75                  80

Ser Arg Trp Thr Lys Arg Lys Gln Val Asp Ile Phe Ser Phe Asp Leu
                85                  90                  95

Ile Leu Ile Pro Leu His Val Gly Gly Asn His Trp Thr Leu Gly Ser
            100                 105                 110

Ile His Met Lys Asp Lys Lys Ile Cys Leu Tyr Asp Ser Leu Asn Gly
        115                 120                 125

Ser Asn Lys Lys Phe Phe Glu Tyr Met Arg Arg Tyr Ile Val Asp Glu
    130                 135                 140

Met Lys Asp Lys Lys Gln Lys Asp Leu Asp Ile
145                 150                 155
```

<210> SEQ ID NO 39
<211> LENGTH: 184
<212> TYPE: PRT
<213> ORGANISM: Trypanosoma brucei

<400> SEQUENCE: 39

```
Lys Trp Asp Ser Ser Arg Ser Gln Asn Ser Gly Glu Gln Glu Arg Val
1               5                   10                  15

Ala Val Ser Leu Lys Ser Gly Ile Ala Ile Thr Tyr Arg Gln Leu Ser
            20                  25                  30

Thr Leu Ala Pro Gly Val Trp Leu Asn Asp Gln Ile Ile Asn Ala Tyr
        35                  40                  45

Leu Gly Leu Ile Cys Asp Glu Tyr Asn Val Arg Ala Gly Cys Glu Ala
    50                  55                  60

Ala Val Ser Met Gly Thr His Phe Tyr Ala Lys Val Gln Gln Glu Met
65                  70                  75                  80

Arg Ile Gly Asn Ala Gly Leu Asn Pro Ser Ser Gly Gly Phe Pro Thr
                85                  90                  95

Leu Glu Gln Asn Ser Gly Val Leu Arg Trp Leu Lys Arg Arg Arg His
            100                 105                 110

Ile Leu Gln Ser Gly Thr Thr Arg Ile Val Leu Val Pro Val Asn Leu
        115                 120                 125

Trp Gln Ser His Trp Thr Leu Ala Val Leu Asp Trp Glu Arg Asn Arg
    130                 135                 140

Trp Thr Tyr Tyr Asp Ser Leu Leu Tyr Gly Asn Ala Pro Val Pro Gln
145                 150                 155                 160

Gly Ser Thr Val Leu Gly Ala Leu His His Thr Phe Glu Glu Ala Arg
                165                 170                 175
```

```
Arg Ile Leu Cys Asp Ser Asp Asp
            180

<210> SEQ ID NO 40
<211> LENGTH: 1224
<212> TYPE: DNA
<213> ORGANISM: Eschericia coli
<220> FEATURE:
<221> NAME/KEY: CDS
<222> LOCATION: (1)..(1221)

<400> SEQUENCE: 40 atg atg gtt aca gtt gtc agc aat tat tgt caa tta tct caa acc caa      48
Met Met Val Thr Val Val Ser Asn Tyr Cys Gln Leu Ser Gln Thr Gln
1               5                   10                  15 ctc agt cag aca ttt gca gaa aaa ttt act gtg acc gag gaa tta ctg      96
Leu Ser Gln Thr Phe Ala Glu Lys Phe Thr Val Thr Glu Glu Leu Leu
            20                  25                  30 cag tct tta aaa aaa aca gcg tta tcc gga gat gaa gaa agc att gag     144
Gln Ser Leu Lys Lys Thr Ala Leu Ser Gly Asp Glu Glu Ser Ile Glu
        35                  40                  45 tta ctg cat aat att gcg tta ggt tat gat gaa ttt ggg aaa aaa gct     192
Leu Leu His Asn Ile Ala Leu Gly Tyr Asp Glu Phe Gly Lys Lys Ala
    50                  55                  60 gaa gat att ctt tac cat att gtt aga aac cca aca aat gat acc cta     240
Glu Asp Ile Leu Tyr His Ile Val Arg Asn Pro Thr Asn Asp Thr Leu
65                  70                  75                  80 tcg att atc aag ctt ata aaa aat gcc tgt tta aaa tta tat aat ttg     288
Ser Ile Ile Lys Leu Ile Lys Asn Ala Cys Leu Lys Leu Tyr Asn Leu
                85                  90                  95 gca cat acc gca acc aaa cac ccc ctc aaa tca cat gat tca gat aat     336
Ala His Thr Ala Thr Lys His Pro Leu Lys Ser His Asp Ser Asp Asn
            100                 105                 110 ctc ctg ttc aaa aaa cta ttc tcc cct tcg aaa tta atg gca att atc     384
Leu Leu Phe Lys Lys Leu Phe Ser Pro Ser Lys Leu Met Ala Ile Ile
        115                 120                 125 ggt gag gac att cct ctc ata tca gaa aaa cag tca ctt tca aag gta     432
Gly Glu Asp Ile Pro Leu Ile Ser Glu Lys Gln Ser Leu Ser Lys Val
    130                 135                 140 ctt tta aat gat aag aat aat gaa ctg agc gat ggg aca aac ttc tgg     480
Leu Leu Asn Asp Lys Asn Asn Glu Leu Ser Asp Gly Thr Asn Phe Trp
145                 150                 155                 160 gat aaa aat cgt caa tta acc aca gat gaa ata gct tgc tat ctt aaa     528
Asp Lys Asn Arg Gln Leu Thr Thr Asp Glu Ile Ala Cys Tyr Leu Lys
                165                 170                 175 aag atc gcc gcc aat gca aaa aat act caa gtc aat tat cct act gat     576
Lys Ile Ala Ala Asn Ala Lys Asn Thr Gln Val Asn Tyr Pro Thr Asp
            180                 185                 190 ttc tac ctc ccc aat tcc aac agc act tac ctg gaa gtc gct ctc aat     624
Phe Tyr Leu Pro Asn Ser Asn Ser Thr Tyr Leu Glu Val Ala Leu Asn
        195                 200                 205 gat aat att aag agc gat cca tca tgg ccg aaa gaa gtc cag tta ttc     672
Asp Asn Ile Lys Ser Asp Pro Ser Trp Pro Lys Glu Val Gln Leu Phe
    210                 215                 220 ccc ata aat act ggc gga cac tgg ata tta gtt tcg cta cag aaa ata     720
Pro Ile Asn Thr Gly Gly His Trp Ile Leu Val Ser Leu Gln Lys Ile
225                 230                 235                 240 gtt aat gaa aaa aac aac aca caa caa ata aaa tgc atc ata ttc aat     768
Val Asn Glu Lys Asn Asn Thr Gln Gln Ile Lys Cys Ile Ile Phe Asn
                245                 250                 255
```

```
tca tta cgt gca cta ggc cat gaa aaa gaa aat tca ctt aag cgt atc      816
Ser Leu Arg Ala Leu Gly His Glu Lys Glu Asn Ser Leu Lys Arg Ile
        260                 265                 270 att aac agt ttc aat agt ttc aat tgt gac ccc acg aga gaa acg ccg      864
Ile Asn Ser Phe Asn Ser Phe Asn Cys Asp Pro Thr Arg Glu Thr Pro
                275                 280                 285 aat aat aag aat ata aca gat cat tta act gaa cca gag ata ata ttt      912
Asn Asn Lys Asn Ile Thr Asp His Leu Thr Glu Pro Glu Ile Ile Phe
    290                 295                 300 tta cat gcc gat ctt cag caa tac tta agc caa agt tgc ggt gca ttt      960
Leu His Ala Asp Leu Gln Gln Tyr Leu Ser Gln Ser Cys Gly Ala Phe
305                 310                 315                 320 gtg tgc atg gca gcc cag gaa gtg att gaa caa atg gaa agc aat tct     1008
Val Cys Met Ala Ala Gln Glu Val Ile Glu Gln Met Glu Ser Asn Ser
                325                 330                 335 gac agc gcc ccc tat acg tta tta aaa aac tat gct gac aga ttt aaa     1056
Asp Ser Ala Pro Tyr Thr Leu Leu Lys Asn Tyr Ala Asp Arg Phe Lys
            340                 345                 350 aaa tat tca gca gaa gag cag tac gaa att gat ttt caa cat cgt ctg     1104
Lys Tyr Ser Ala Glu Glu Gln Tyr Glu Ile Asp Phe Gln His Arg Leu
        355                 360                 365 gaa aac aga aat tgt tat tta gat aaa tat ggc gat gca aat atc aat     1152
Glu Asn Arg Asn Cys Tyr Leu Asp Lys Tyr Gly Asp Ala Asn Ile Asn
    370                 375                 380 cat tat tat aga aac tta gaa ata aaa aac tca cac ccc aaa aat aga     1200
His Tyr Tyr Arg Asn Leu Glu Ile Lys Asn Ser His Pro Lys Asn Arg
385                 390                 395                 400 gca tca agc aaa aga gta agt taa                                     1224
Ala Ser Ser Lys Arg Val Ser
                405
```

<210> SEQ ID NO 41
<211> LENGTH: 407
<212> TYPE: PRT
<213> ORGANISM: Eschericia coli

<400> SEQUENCE: 41

```
Met Met Val Thr Val Ser Asn Tyr Cys Gln Leu Ser Gln Thr Gln
1               5                   10                  15

Leu Ser Gln Thr Phe Ala Glu Lys Phe Thr Val Thr Glu Glu Leu Leu
            20                  25                  30

Gln Ser Leu Lys Lys Thr Ala Leu Ser Gly Asp Glu Glu Ser Ile Glu
        35                  40                  45

Leu Leu His Asn Ile Ala Leu Gly Tyr Asp Glu Phe Gly Lys Lys Ala
    50                  55                  60

Glu Asp Ile Leu Tyr His Ile Val Arg Asn Pro Thr Asn Asp Thr Leu
65                  70                  75                  80

Ser Ile Ile Lys Leu Ile Lys Asn Ala Cys Leu Lys Leu Tyr Asn Leu
                85                  90                  95

Ala His Thr Ala Thr Lys His Pro Leu Lys Ser His Asp Ser Asp Asn
            100                 105                 110

Leu Leu Phe Lys Lys Leu Phe Ser Pro Ser Lys Leu Met Ala Ile Ile
        115                 120                 125

Gly Glu Asp Ile Pro Leu Ile Ser Glu Lys Gln Ser Leu Ser Lys Val
    130                 135                 140

Leu Leu Asn Asp Lys Asn Asn Glu Leu Ser Asp Gly Thr Asn Phe Trp
145                 150                 155                 160

Asp Lys Asn Arg Gln Leu Thr Thr Asp Glu Ile Ala Cys Tyr Leu Lys
```

-continued

```
                165                 170                 175
Lys Ile Ala Ala Asn Ala Lys Asn Thr Gln Val Asn Tyr Pro Thr Asp
            180                 185                 190

Phe Tyr Leu Pro Asn Ser Asn Ser Thr Tyr Leu Glu Val Ala Leu Asn
            195                 200                 205

Asp Asn Ile Lys Ser Asp Pro Ser Trp Pro Lys Glu Val Gln Leu Phe
            210                 215                 220

Pro Ile Asn Thr Gly Gly His Trp Ile Leu Val Ser Leu Gln Lys Ile
225                 230                 235                 240

Val Asn Glu Lys Asn Asn Thr Gln Gln Ile Lys Cys Ile Ile Phe Asn
            245                 250                 255

Ser Leu Arg Ala Leu Gly His Glu Lys Glu Asn Ser Leu Lys Arg Ile
            260                 265                 270

Ile Asn Ser Phe Asn Ser Phe Asn Cys Asp Pro Thr Arg Glu Thr Pro
            275                 280                 285

Asn Asn Lys Asn Ile Thr Asp His Leu Thr Glu Pro Glu Ile Ile Phe
            290                 295                 300

Leu His Ala Asp Leu Gln Gln Tyr Leu Ser Gln Ser Cys Gly Ala Phe
305                 310                 315                 320

Val Cys Met Ala Ala Gln Glu Val Ile Glu Gln Met Glu Ser Asn Ser
            325                 330                 335

Asp Ser Ala Pro Tyr Thr Leu Leu Lys Asn Tyr Ala Asp Arg Phe Lys
            340                 345                 350

Lys Tyr Ser Ala Glu Gln Tyr Glu Ile Asp Phe Gln His Arg Leu
            355                 360                 365

Glu Asn Arg Asn Cys Tyr Leu Asp Lys Tyr Gly Asp Ala Asn Ile Asn
            370                 375                 380

His Tyr Arg Asn Leu Glu Ile Lys Asn Ser His Pro Lys Asn Arg
385                 390                 395                 400

Ala Ser Ser Lys Arg Val Ser
            405

<210> SEQ ID NO 42
<211> LENGTH: 233
<212> TYPE: PRT
<213> ORGANISM: Eschericia coli

<400> SEQUENCE: 42

Gly Glu Asp Ile Pro Leu Ile Ser Glu Lys Gln Ser Leu Ser Lys Val
1               5                   10                  15

Leu Leu Asn Asp Lys Asn Glu Leu Ser Asp Gly Thr Asn Phe Trp
            20                  25                  30

Asp Lys Asn Arg Gln Leu Thr Thr Asp Glu Ile Ala Cys Tyr Leu Lys
            35                  40                  45

Lys Ile Ala Ala Asn Ala Lys Asn Thr Gln Val Asn Tyr Pro Thr Asp
            50                  55                  60

Phe Tyr Leu Pro Asn Ser Asn Ser Thr Tyr Leu Glu Val Ala Leu Asn
65                  70                  75                  80

Asp Asn Ile Lys Ser Asp Pro Ser Trp Pro Lys Glu Val Gln Leu Phe
            85                  90                  95

Pro Ile Asn Thr Gly Gly His Trp Ile Leu Val Ser Leu Gln Lys Ile
            100                 105                 110

Val Asn Glu Lys Asn Asn Thr Gln Gln Ile Lys Cys Ile Ile Phe Asn
            115                 120                 125
```

```
Ser Leu Arg Ala Leu Gly His Glu Lys Glu Asn Ser Leu Lys Arg Ile
        130                 135                 140

Ile Asn Ser Phe Asn Ser Phe Asn Cys Asp Pro Thr Arg Glu Thr Pro
145                 150                 155                 160

Asn Asn Lys Asn Ile Thr Asp His Leu Thr Glu Pro Glu Ile Ile Phe
                165                 170                 175

Leu His Ala Asp Leu Gln Gln Tyr Leu Ser Gln Ser Cys Gly Ala Phe
            180                 185                 190

Val Cys Met Ala Ala Gln Glu Val Ile Glu Gln Met Glu Ser Asn Ser
        195                 200                 205

Asp Ser Ala Pro Tyr Thr Leu Leu Lys Asn Tyr Ala Asp Arg Phe Lys
    210                 215                 220

Lys Tyr Ser Ala Glu Glu Gln Tyr Glu
225                 230

<210> SEQ ID NO 43
<211> LENGTH: 2486
<212> TYPE: DNA
<213> ORGANISM: Cryptosporidium parvum
<220> FEATURE:
<221> NAME/KEY: CDS
<222> LOCATION: (299)..(1666)

<400> SEQUENCE: 43
ggctattttc tttgcaattt tcattgtttg ttctattaat tctgttcgag taaaaaatca    60 gaatatttt attaaatgca aaaatttga ataaattaaa agaaagctta attttattgg    120
ataataagtt gaattgacta gaaaataact caaattcttc aagaaaaggt tatttgcaat    180
atcagagatt ggaaatgtaa aatgtaattc tagctcaata aaatacattg actttataat    240
tatatatata aagtgaatat tatatcagga agattatcta atttatgggg ctttctaa      298 atg aga ggg aga aga aac tat aat ggt aat tta cca tta aaa att atg    346
Met Arg Gly Arg Arg Asn Tyr Asn Gly Asn Leu Pro Leu Lys Ile Met
1               5                   10                  15 agc agc agc caa atc ttg tca cag tat ata tct tta aat cat gga ccg    394
Ser Ser Ser Gln Ile Leu Ser Gln Tyr Ile Ser Leu Asn His Gly Pro
            20                  25                  30 tat cat act gaa gga aga aca agc cta ttt gac aag aga aag gag aat    442
Tyr His Thr Glu Gly Arg Thr Ser Leu Phe Asp Lys Arg Lys Glu Asn
        35                  40                  45 ttt tct aga att ttg aat ttt caa atc cct gta aga gaa aga ttt tcg    490
Phe Ser Arg Ile Leu Asn Phe Gln Ile Pro Val Arg Glu Arg Phe Ser
    50                  55                  60 cct aat aag atg cat tta aac aag tat ctg cca gta gaa aag ccc agg    538
Pro Asn Lys Met His Leu Asn Lys Tyr Leu Pro Val Glu Lys Pro Arg
65                  70                  75                  80 aag gat att tta agt tca agc tta agt gat gat tta acc cca att agc    586
Lys Asp Ile Leu Ser Ser Ser Leu Ser Asp Asp Leu Thr Pro Ile Ser
                85                  90                  95 aaa aca agt act ata ata aat aaa tac cag gag att aaa agt aaa cac    634
Lys Thr Ser Thr Ile Ile Asn Lys Tyr Gln Glu Ile Lys Ser Lys His
            100                 105                 110 agg gta att tat tat gaa aaa agt gga tct gac tct gac gat gga ctt    682
Arg Val Ile Tyr Tyr Glu Lys Ser Gly Ser Asp Ser Asp Asp Gly Leu
        115                 120                 125 tta aaa cga tca tta gag ttt atc aaa aga ata tca aaa agt aac aat    730
Leu Lys Arg Ser Leu Glu Phe Ile Lys Arg Ile Ser Lys Ser Asn Asn
    130                 135                 140 cat tta gaa gtt ctt ggt agt cat tta aat agt ctt gca tta tgt gag    778
```

```
His Leu Glu Val Leu Gly Ser His Leu Asn Ser Leu Ala Leu Cys Glu
145                 150                 155                 160 aga aat ctt gaa gat aag agg aaa gaa ttt aag aag ctt gtt tat ggt        826
Arg Asn Leu Glu Asp Lys Arg Lys Glu Phe Lys Lys Leu Val Tyr Gly
                165                 170                 175 ttg gat gat agc caa ttt gaa gaa caa gaa tcg aaa gaa aaa gat gaa        874
Leu Asp Asp Ser Gln Phe Glu Glu Gln Glu Ser Lys Glu Lys Asp Glu
            180                 185                 190 tta ttt gtt tct ctt gga gta ata aaa tat aaa tat cca ata gaa tgt        922
Leu Phe Val Ser Leu Gly Val Ile Lys Tyr Lys Tyr Pro Ile Glu Cys
        195                 200                 205 tct gat gaa gag tta aac aag gct agg agt tac tta aat agc tta agt        970
Ser Asp Glu Glu Leu Asn Lys Ala Arg Ser Tyr Leu Asn Ser Leu Ser
    210                 215                 220 aat aga gga cag att gta gct att aat tat aaa agt aat att gaa tta       1018
Asn Arg Gly Gln Ile Val Ala Ile Asn Tyr Lys Ser Asn Ile Glu Leu
225                 230                 235                 240 aca att gat ttg att caa tgt tta aga tca caa caa tgg tta aat gac       1066
Thr Ile Asp Leu Ile Gln Cys Leu Arg Ser Gln Gln Trp Leu Asn Asp
                245                 250                 255 gaa tta att aac ttt tac ttc tca atg ctt caa gaa aga aat gat cgt       1114
Glu Leu Ile Asn Phe Tyr Phe Ser Met Leu Gln Glu Arg Asn Asp Arg
            260                 265                 270 caa act tcc aat gga ttt aag cct aaa gta tgg ctt tgg aac tct ttc       1162
Gln Thr Ser Asn Gly Phe Lys Pro Lys Val Trp Leu Trp Asn Ser Phe
        275                 280                 285 ttt tac aca aaa tta aca tgt gat caa agt aat gat gaa aca gga tat       1210
Phe Tyr Thr Lys Leu Thr Cys Asp Gln Ser Asn Asp Glu Thr Gly Tyr
    290                 295                 300 tgt tat aaa aat gtt tca aga tgg aca cag aga aaa aaa att gac tta       1258
Cys Tyr Lys Asn Val Ser Arg Trp Thr Gln Arg Lys Lys Ile Asp Leu
305                 310                 315                 320 ttt aat tat gat att gta ctt tta cct att aat gtc aat aat gta cat       1306
Phe Asn Tyr Asp Ile Val Leu Leu Pro Ile Asn Val Asn Asn Val His
                325                 330                 335 tgg act ttg ggc gtt gtt aat ttt aag ctt gga tat att cag tac ata       1354
Trp Thr Leu Gly Val Val Asn Phe Lys Leu Gly Tyr Ile Gln Tyr Ile
            340                 345                 350 gat tca tta ggc ggg caa ttt caa gac cat ttg ggc tgc aca aag atg       1402
Asp Ser Leu Gly Gly Gln Phe Gln Asp His Leu Gly Cys Thr Lys Met
        355                 360                 365 tca gcc ata ttc ttt caa aac atg aat aga tat ata cag gat gaa tat       1450
Ser Ala Ile Phe Phe Gln Asn Met Asn Arg Tyr Ile Gln Asp Glu Tyr
    370                 375                 380 ttt gat aaa aaa aag gag aaa ttt cca ggc cag ctg aag cat ttt acg       1498
Phe Asp Lys Lys Lys Glu Lys Phe Pro Gly Gln Leu Lys His Phe Thr
385                 390                 395                 400 agg ttt tca gaa cca gtt cca caa cag aat aat ggc tca gat tgt ggg       1546
Arg Phe Ser Glu Pro Val Pro Gln Gln Asn Asn Gly Ser Asp Cys Gly
                405                 410                 415 gta ttc aca tgt atg ttt gct gag tgt att tct gaa gga agg tct ttt       1594
Val Phe Thr Cys Met Phe Ala Glu Cys Ile Ser Glu Gly Arg Ser Phe
            420                 425                 430 gat ttt gac aca act caa att gac agg att cgt gag gtt atg tta gtg       1642
Asp Phe Asp Thr Thr Gln Ile Asp Arg Ile Arg Glu Val Met Leu Val
        435                 440                 445 gaa tgt att aga aat gaa ata ttt tgagaatttt caggtattta tactcatcgg     1696
Glu Cys Ile Arg Asn Glu Ile Phe
    450                 455
```

-continued

```
aataaatatt ccaaatagtt tcttctatta attaaattat attaacaatg tttaaagcaa   1756
ttttattaag tgcttaatat taacatacag aagaagaaga aaaaagaaaa ggttatattt   1816
taatctagtc aaaattttta ggtagttgtt attaaaatta acttaatatt tgaattttac   1876
taattttgtt tactgcaaaa taatagatta tactatagat aaaggtagta atcatatacc   1936
atcaattatc catgaattta catgtaccca agcattgcag ccaccagtat taactattcc   1996
cagagtaaag tacttgaagt tacaggtttc agcgatatct gtcattccgg aatatttgaa   2056
aatattatca gttctaatca aagtggttgc tggagctgtt tgcatgtttt ctgaagtata   2116
tcctgtcgtt tcaaaagcag atacaatagt agaagggtct ttaaccaaac ttgtattact   2176
tgaacataaa tcatcacaaa tctttataaa ttttaaagtg agtgaattcg ctgaacatgt   2236
acagttataa gaatcacagt aagttttttag cgaaatatag gaagatttac ttgaattacg   2296
gataatcttg gcataactag ataagtcaaa ttggattagt aaagtattat cccaacctgt   2356
actgaaagca gacgtaattg gaagatacat aacgtttcct gaatattccc agcaaaagtt   2416
tgagcttgta ttgatcatat tctgtgtcac aaacatgctt gttggagtaa ttgtggcgca   2476
agggtctttt                                                          2486
```

<210> SEQ ID NO 44
<211> LENGTH: 456
<212> TYPE: PRT
<213> ORGANISM: Cryptosporidium parvum

<400> SEQUENCE: 44

```
Met Arg Gly Arg Arg Asn Tyr Asn Gly Asn Leu Pro Leu Lys Ile Met
1               5                   10                  15

Ser Ser Ser Gln Ile Leu Ser Gln Tyr Ile Ser Leu Asn His Gly Pro
            20                  25                  30

Tyr His Thr Glu Gly Arg Thr Ser Leu Phe Asp Lys Arg Lys Glu Asn
        35                  40                  45

Phe Ser Arg Ile Leu Asn Phe Gln Ile Pro Val Arg Glu Arg Phe Ser
    50                  55                  60

Pro Asn Lys Met His Leu Asn Lys Tyr Leu Val Glu Lys Pro Arg
65                  70                  75                  80

Lys Asp Ile Leu Ser Ser Ser Leu Ser Asp Asp Leu Thr Pro Ile Ser
                85                  90                  95

Lys Thr Ser Thr Ile Ile Asn Lys Tyr Gln Glu Ile Lys Ser Lys His
            100                 105                 110

Arg Val Ile Tyr Tyr Glu Lys Ser Gly Ser Asp Ser Asp Gly Leu
        115                 120                 125

Leu Lys Arg Ser Leu Glu Phe Ile Lys Arg Ile Ser Lys Ser Asn Asn
    130                 135                 140

His Leu Glu Val Leu Gly Ser His Leu Asn Ser Leu Ala Leu Cys Glu
145                 150                 155                 160

Arg Asn Leu Glu Asp Lys Arg Lys Glu Phe Lys Lys Leu Val Tyr Gly
                165                 170                 175

Leu Asp Asp Ser Gln Phe Glu Glu Gln Ser Lys Glu Lys Asp Glu
            180                 185                 190

Leu Phe Val Ser Leu Gly Val Ile Lys Tyr Lys Tyr Pro Ile Glu Cys
        195                 200                 205

Ser Asp Glu Glu Leu Asn Lys Ala Arg Ser Tyr Leu Asn Ser Leu Ser
    210                 215                 220

Asn Arg Gly Gln Ile Val Ala Ile Asn Tyr Lys Ser Asn Ile Glu Leu
```

```
                     225                 230                 235                 240

Thr Ile Asp Leu Ile Gln Cys Leu Arg Ser Gln Gln Trp Leu Asn Asp
                    245                 250                 255

Glu Leu Ile Asn Phe Tyr Phe Ser Met Leu Gln Glu Arg Asn Asp Arg
                    260                 265                 270

Gln Thr Ser Asn Gly Phe Lys Pro Lys Val Trp Leu Trp Asn Ser Phe
                    275                 280                 285

Phe Tyr Thr Lys Leu Thr Cys Asp Gln Ser Asn Asp Glu Thr Gly Tyr
                    290                 295                 300

Cys Tyr Lys Asn Val Ser Arg Trp Thr Gln Arg Lys Lys Ile Asp Leu
305                 310                 315                 320

Phe Asn Tyr Asp Ile Val Leu Leu Pro Ile Asn Val Asn Asn Val His
                    325                 330                 335

Trp Thr Leu Gly Val Val Asn Phe Lys Leu Gly Tyr Ile Gln Tyr Ile
                    340                 345                 350

Asp Ser Leu Gly Gly Gln Phe Gln Asp His Leu Gly Cys Thr Lys Met
                    355                 360                 365

Ser Ala Ile Phe Phe Gln Asn Met Asn Arg Tyr Ile Gln Asp Glu Tyr
                    370                 375                 380

Phe Asp Lys Lys Lys Glu Lys Phe Pro Gly Gln Leu Lys His Phe Thr
385                 390                 395                 400

Arg Phe Ser Glu Pro Val Pro Gln Gln Asn Asn Gly Ser Asp Cys Gly
                    405                 410                 415

Val Phe Thr Cys Met Phe Ala Glu Cys Ile Ser Glu Gly Arg Ser Phe
                    420                 425                 430

Asp Phe Asp Thr Thr Gln Ile Asp Arg Ile Arg Glu Val Met Leu Val
                    435                 440                 445

Glu Cys Ile Arg Asn Glu Ile Phe
450                 455

<210> SEQ ID NO 45
<211> LENGTH: 201
<212> TYPE: PRT
<213> ORGANISM: Cryptosporidium parvum

<400> SEQUENCE: 45

Lys Ser Asn Ile Glu Leu Thr Ile Asp Leu Ile Gln Cys Leu Arg Ser
1               5                   10                  15

Gln Gln Trp Leu Asn Asp Glu Leu Ile Asn Phe Tyr Phe Ser Met Leu
                20                  25                  30

Gln Glu Arg Asn Asp Arg Gln Thr Ser Asn Gly Phe Lys Pro Lys Val
            35                  40                  45

Trp Leu Trp Asn Ser Phe Phe Tyr Thr Lys Leu Thr Cys Asp Gln Ser
        50                  55                  60

Asn Asp Glu Thr Gly Tyr Cys Tyr Lys Asn Val Ser Arg Trp Thr Gln
65                  70                  75                  80

Arg Lys Lys Ile Asp Leu Phe Asn Tyr Asp Ile Val Leu Leu Pro Ile
                85                  90                  95

Asn Val Asn Asn Val His Trp Thr Leu Gly Val Val Asn Phe Lys Leu
            100                 105                 110

Gly Tyr Ile Gln Tyr Ile Asp Ser Leu Gly Gly Gln Phe Gln Asp His
        115                 120                 125

Leu Gly Cys Thr Lys Met Ser Ala Ile Phe Phe Gln Asn Met Asn Arg
    130                 135                 140
```

```
Tyr Ile Gln Asp Glu Tyr Phe Asp Lys Lys Glu Lys Phe Pro Gly
145                 150                 155                 160

Gln Leu Lys His Phe Thr Arg Phe Ser Glu Pro Val Pro Gln Gln Asn
            165                 170                 175

Asn Gly Ser Asp Cys Gly Val Phe Thr Cys Met Phe Ala Glu Cys Ile
        180                 185                 190

Ser Glu Gly Arg Ser Phe Asp Phe Asp
        195                 200

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggaattcatg ttgtctccca ccaactca                                    28

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cctcgagtta gaaaagagct tttgcttcag                                  30

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggaattcatg aatattatgt gtaaattcac ttta                             34

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cctcgagtac tcgccattac tggagact                                    28

<210> SEQ ID NO 50
<211> LENGTH: 317
<212> TYPE: PRT
<213> ORGANISM: Salmonella enterica

<400> SEQUENCE: 50

Met Ser Asp Glu Ala Leu Ala Leu Leu Phe Ser Ala Val Glu Asn Gly
1               5                   10                  15

Asp Gln Asn Cys Ile Asp Leu Leu Cys Asn Leu Ala Leu Arg Asn Asp
            20                  25                  30

Asn Leu Gly His Arg Val Glu Lys Phe Leu Phe Asp Leu Phe Ser Gly
```

-continued

```
                35                  40                  45
Lys Arg Ser Gly Ser Pro Asp Ile Asp Lys Ile Asn Gln Ala Cys
 50                  55                  60

Leu Val Leu His Gln Ile Ala Asn Asn Asp Ile Thr Lys Asp Asn Thr
 65                  70                  75                  80

Glu Trp Lys Lys Leu His Ala Pro Ser Arg Leu Leu Tyr Met Ala Gly
                 85                  90                  95

Ser Ala Thr Thr Asp Leu Ser Lys Lys Ile Gly Ile Ala His Lys Ile
                100                 105                 110

Met Gly Asp Gln Phe Ala Gln Thr Asp Gln Glu Gln Val Gly Val Glu
            115                 120                 125

Asn Leu Trp Cys Ser Ala Arg Met Leu Ser Ser Asp Glu Leu Ala Ala
130                 135                 140

Ala Thr Leu Gly Leu Val Gln Glu Ser Pro Leu Leu Ser Val Asn Tyr
145                 150                 155                 160

Pro Ile Gly Leu Ile His Pro Thr Thr Lys Glu Asn Ile Leu Arg Thr
                165                 170                 175

Gln Leu Leu Glu Lys Met Ala Gln Ser Gly Leu Ser Glu Asn Glu Val
            180                 185                 190

Phe Leu Ile Asn Thr Gly Asp His Trp Leu Ile Cys Leu Phe Tyr Lys
        195                 200                 205

Leu Ala Glu Lys Ile Lys Cys Leu Ile Phe Asn Thr Tyr His Asp Leu
    210                 215                 220

Asn Glu Asn Thr Lys Gln Glu Ile Ile Glu Ala Ala Lys Ile Thr Gly
225                 230                 235                 240

Ile Ser Glu Asn Glu Asp Ile Asp Phe Ile Glu Thr Asn Leu Gln Asn
                245                 250                 255

Asn Val Pro Asn Gly Cys Gly Leu Phe Cys Tyr His Thr Ile Gln Leu
            260                 265                 270

Leu Ser Asn Ala Gly Gln Asn Asp Pro Ala Thr Thr Leu Arg Glu Phe
        275                 280                 285

Ala Glu Asn Phe Leu Thr Leu Ser Val Glu Gln Thr Leu Phe Asn
    290                 295                 300

Thr Gln Thr Arg Arg Gln Ile Tyr Glu Tyr Ser Leu Gln
305                 310                 315

<210> SEQ ID NO 51
<211> LENGTH: 317
<212> TYPE: PRT
<213> ORGANISM: Salmonella typhimurium

<400> SEQUENCE: 51

Met Ser Asp Glu Ala Leu Thr Leu Leu Phe Ser Ala Val Glu Asn Gly
 1               5                  10                  15

Asp Gln Asn Cys Ile Asp Leu Leu Cys Asn Leu Ala Leu Arg Asn Asp
                20                  25                  30

Asp Leu Gly His Arg Val Glu Lys Phe Leu Phe Asp Leu Phe Ser Gly
            35                  40                  45

Lys Arg Thr Gly Ser Ser Asp Ile Asp Lys Ile Asn Gln Ala Cys
 50                  55                  60

Leu Val Leu His Gln Ile Ala Asn Asn Asp Ile Thr Lys Asp Asn Thr
 65                  70                  75                  80

Glu Trp Lys Lys Leu His Ala Pro Ser Arg Leu Leu Tyr Met Ala Gly
                 85                  90                  95
```

```
Ser Ala Thr Thr Asp Leu Ser Lys Lys Ile Gly Ile Ala His Lys Ile
            100                 105                 110

Met Gly Asp Gln Phe Ala Gln Thr Asp Gln Glu Gln Val Gly Val Glu
        115                 120                 125

Asn Leu Trp Cys Gly Ala Arg Met Leu Ser Ser Asp Glu Leu Ala Ala
    130                 135                 140

Ala Thr Gln Gly Leu Val Gln Glu Ser Pro Leu Leu Ser Val Asn Tyr
145                 150                 155                 160

Pro Ile Gly Leu Ile His Pro Thr Thr Lys Glu Asn Ile Leu Ser Thr
                165                 170                 175

Gln Leu Leu Glu Lys Ile Ala Gln Ser Gly Leu Ser His Asn Glu Val
            180                 185                 190

Phe Leu Val Asn Thr Gly Asp His Trp Leu Leu Cys Leu Phe Tyr Lys
        195                 200                 205

Leu Ala Glu Lys Ile Lys Cys Leu Ile Phe Asn Thr Tyr Tyr Asp Leu
    210                 215                 220

Asn Glu Asn Thr Lys Gln Glu Ile Ile Glu Ala Ala Lys Ile Ala Gly
225                 230                 235                 240

Ile Ser Glu Ser Asp Glu Val Asn Phe Ile Glu Met Asn Leu Gln Asn
                245                 250                 255

Asn Val Pro Asn Gly Cys Gly Leu Phe Cys Tyr His Thr Ile Gln Leu
            260                 265                 270

Leu Ser Asn Ala Gly Gln Asn Asp Pro Ala Thr Thr Leu Arg Glu Phe
        275                 280                 285

Ala Glu Asn Phe Leu Thr Leu Ser Val Glu Glu Gln Ala Leu Phe Asn
    290                 295                 300

Thr Gln Thr Arg Arg Gln Ile Tyr Glu Tyr Ser Leu Gln
305                 310                 315

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Glu Val Asp
1

<210> SEQ ID NO 53
<211> LENGTH: 93
<212> TYPE: PRT
<213> ORGANISM: Homo sapiens

<400> SEQUENCE: 53

His Trp Ser Leu Ile Ser Val Asp Val Arg Arg Thr Ile Thr Tyr
1               5                   10                  15

Phe Asp Ser Gln Arg Thr Leu Asn Arg Arg Cys Pro Lys His Ile Ala
            20                  25                  30

Lys Tyr Leu Gln Ala Glu Ala Val Lys Lys Asp Arg Leu Asp Phe His
        35                  40                  45

Gln Gly Trp Lys Gly Tyr Phe Lys Met Asn Val Ala Arg Gln Asn Asn
    50                  55                  60

Asp Ser Asp Cys Gly Ala Phe Val Leu Gln Tyr Cys Lys His Leu Ala
65                  70                  75                  80
```

Leu Ser Gln Pro Phe Ser Phe Thr Gln Gln Asp Met Pro
                85                  90

<210> SEQ ID NO 54
<211> LENGTH: 217
<212> TYPE: PRT
<213> ORGANISM: Saccharomyces cerevisiae

<400> SEQUENCE: 54

Gly Ser Leu Val Pro Glu Leu Asn Glu Lys Asp Asp Gln Val Gln
1               5                   10                  15

Lys Ala Leu Ala Ser Arg Glu Asn Thr Gln Leu Met Asn Arg Asp Asn
                20                  25                  30

Ile Glu Ile Thr Val Arg Asp Phe Lys Thr Leu Ala Pro Arg Arg Trp
            35                  40                  45

Leu Asn Asp Thr Ile Ile Glu Phe Pro Met Lys Tyr Ile Glu Lys Ser
        50                  55                  60

Thr Pro Asn Thr Val Ala Phe Asn Ser Phe Phe Tyr Thr Asn Leu Ser
65                  70                  75                  80

Glu Arg Gly Tyr Gln Gly Val Arg Arg Trp Met Lys Arg Lys Lys Thr
                85                  90                  95

Gln Ile Asp Lys Leu Asp Lys Ile Phe Thr Pro Ile Asn Leu Asn Gln
                100                 105                 110

Ser His Trp Ala Leu Gly Ile Ile Asp Leu Lys Lys Thr Ile Gly
            115                 120                 125

Tyr Val Asp Ser Leu Ser Asn Gly Pro Asn Ala Met Ser Phe Ala Ile
        130                 135                 140

Leu Thr Asp Leu Gln Lys Tyr Val Met Glu Glu Ser Lys His Thr Ile
145                 150                 155                 160

Gly Glu Asp Phe Asp Leu Ile His Leu Asp Cys Pro Gln Gln Pro Asn
                165                 170                 175

Gly Tyr Asp Cys Gly Ile Tyr Val Cys Met Asn Thr Leu Tyr Gly Ser
            180                 185                 190

Ala Asp Ala Pro Leu Asp Phe Asp Tyr Lys Asp Ala Ile Arg Met Arg
        195                 200                 205

Arg Phe Ile Ala His Leu Ile Leu Thr
    210                 215

<210> SEQ ID NO 55
<211> LENGTH: 185
<212> TYPE: PRT
<213> ORGANISM: Homo sapiens

<400> SEQUENCE: 55

Val Phe Arg Asn Gly Asn Gln Asp Glu Val Leu Ser Glu Ala Phe Arg
1               5                   10                  15

Leu Thr Ile Thr Arg Lys Asp Ile Gln Thr Leu Asn His Leu Asn Trp
                20                  25                  30

Leu Asn Asp Glu Ile Ile Asn Phe Tyr Met Asn Met Leu Met Glu Arg
            35                  40                  45

Ser Lys Glu Lys Gly Leu Pro Ser Val His Ala Phe Asn Thr Phe Phe
        50                  55                  60

Phe Thr Lys Leu Lys Thr Ala Gly Tyr Gln Ala Val Lys Arg Trp Thr
65                  70                  75                  80

Lys Lys Val Asp Val Phe Ser Val Asp Ile Leu Leu Val Pro Ile His
                85                  90                  95

```
Leu Gly Val His Trp Cys Leu Ala Val Val Asp Phe Arg Lys Lys Asn
            100                 105                 110

Ile Thr Tyr Tyr Asp Ser Met Gly Gly Ile Asn Asn Glu Ala Cys Arg
        115                 120                 125

Ile Leu Leu Gln Tyr Leu Lys Gln Glu Ser Ile Asp Lys Lys Arg Lys
    130                 135                 140

Glu Phe Asp Thr Asn Gly Trp Gln Leu Phe Ser Lys Lys Ser Gln Ile
145                 150                 155                 160

Pro Gln Gln Met Asn Gly Ser Asp Cys Gly Met Phe Ala Cys Lys Tyr
                165                 170                 175

Ala Asp Cys Ile Thr Lys Asp Arg Pro
            180                 185

<210> SEQ ID NO 56
<211> LENGTH: 153
<212> TYPE: PRT
<213> ORGANISM: Homo sapiens

<400> SEQUENCE: 56

Leu Asn Trp Leu Asn Asp Glu Ile Ile Asn Phe Tyr Met Asn Met Leu
1               5                   10                  15

Met Glu Arg Ser Lys Glu Lys Gly Leu Pro Ser Val His Ala Phe Asn
            20                  25                  30

Thr Phe Phe Phe Thr Lys Leu Lys Thr Ala Gly Tyr Gln Ala Val Lys
        35                  40                  45

Arg Trp Thr Lys Lys Val Asp Val Phe Ser Val Asp Ile Leu Leu Val
    50                  55                  60

Pro Ile His Leu Gly Val His Trp Cys Leu Ala Val Val Asp Phe Arg
65                  70                  75                  80

Lys Lys Asn Ile Thr Tyr Tyr Asp Ser Met Gly Gly Ile Asn Asn Glu
                85                  90                  95

Ala Cys Arg Ile Leu Leu Gln Tyr Leu Lys Gln Glu Ser Ile Asp Lys
            100                 105                 110

Lys Arg Lys Glu Phe Asp Thr Asn Gly Trp Gln Leu Phe Ser Lys Lys
        115                 120                 125

Ser Gln Ile Pro Gln Gln Met Asn Gly Ser Asp Cys Gly Met Phe Ala
    130                 135                 140

Cys Lys Tyr Ala Asp Cys Ile Thr Lys
145                 150

<210> SEQ ID NO 57
<211> LENGTH: 114
<212> TYPE: PRT
<213> ORGANISM: Saccharomyces cerevisiae

<400> SEQUENCE: 57

Leu Val Pro Ile His Leu Gly Val His Trp Cys Leu Ala Val Val Asp
1               5                   10                  15

Phe Arg Lys Lys Asn Ile Thr Tyr Tyr Asp Ser Met Gly Gly Ile Asn
            20                  25                  30

Asn Glu Ala Cys Arg Ile Leu Leu Gln Tyr Leu Lys Gln Glu Ser Ile
        35                  40                  45

Asp Lys Lys Arg Lys Glu Phe Asp Thr Asn Gly Trp Gln Leu Phe Ser
    50                  55                  60

Lys Lys Ser Gln Ile Pro Gln Gln Met Asn Gly Ser Asp Cys Gly Met
65                  70                  75                  80
```

```
Phe Ala Cys Lys Tyr Ala Asp Cys Ile Thr Lys Asp Arg Pro Ile Asn
                85                  90                  95

Phe Thr Gln Gln His Met Pro Tyr Phe Arg Lys Arg Met Val Trp Glu
            100                 105                 110

Ile Leu

<210> SEQ ID NO 58
<211> LENGTH: 219
<212> TYPE: PRT
<213> ORGANISM: Saccharomyces cerevisiae

<400> SEQUENCE: 58

Ser Leu Val Pro Glu Leu Asn Glu Lys Asp Asp Gln Val Gln Lys
1               5                   10                  15

Ala Leu Ala Ser Arg Glu Asn Thr Gln Leu Met Asn Arg Asp Asn Ile
            20                  25                  30

Glu Ile Thr Val Arg Asp Phe Lys Thr Leu Ala Pro Arg Arg Trp Leu
        35                  40                  45

Asn Asp Thr Ile Ile Glu Phe Phe Met Lys Tyr Ile Glu Lys Ser Thr
50                  55                  60

Pro Asn Thr Val Ala Phe Asn Ser Phe Phe Tyr Thr Asn Leu Ser Glu
65                  70                  75                  80

Arg Gly Tyr Gln Gly Val Arg Arg Trp Met Lys Arg Lys Thr Gln
                85                  90                  95

Ile Asp Lys Leu Asp Lys Ile Phe Thr Pro Ile Asn Leu Asn Gln Ser
            100                 105                 110

His Trp Ala Leu Gly Ile Ile Asp Leu Lys Lys Lys Thr Ile Gly Tyr
        115                 120                 125

Val Asp Ser Leu Ser Asn Gly Pro Asn Ala Met Ser Phe Ala Ile Leu
130                 135                 140

Thr Asp Leu Gln Lys Tyr Val Met Glu Glu Ser Lys His Thr Ile Gly
145                 150                 155                 160

Glu Asp Phe Asp Leu Ile His Leu Asp Cys Pro Gln Gln Pro Asn Gly
                165                 170                 175

Tyr Asp Cys Gly Ile Tyr Val Cys Met Asn Thr Leu Tyr Gly Ser Ala
            180                 185                 190

Asp Ala Pro Leu Asp Phe Asp Tyr Lys Asp Ala Ile Arg Met Arg Arg
        195                 200                 205

Phe Ile Ala His Leu Ile Leu Thr Asp Ala Leu
210                 215

<210> SEQ ID NO 59
<211> LENGTH: 144
<212> TYPE: PRT
<213> ORGANISM: Saccharomyces cerevisiae

<400> SEQUENCE: 59

Glu Asn Thr Gln Leu Met Asn Arg Asp Asn Ile Glu Ile Thr Val Arg
1               5                   10                  15

Asp Phe Lys Thr Leu Ala Pro Arg Arg Trp Leu Asn Asp Thr Ile Ile
            20                  25                  30

Glu Phe Phe Met Lys Tyr Ile Glu Lys Ser Thr Pro Asn Thr Val Ala
        35                  40                  45

Phe Asn Ser Phe Phe Tyr Thr Asn Leu Ser Glu Arg Gly Tyr Gln Gly
50                  55                  60

Val Arg Arg Trp Met Lys Arg Lys Lys Thr Gln Ile Asp Lys Leu Asp
```

```
                                      -continued
65                      70                      75                      80
Lys Ile Phe Thr Pro Ile Asn Leu Asn Gln Ser His Trp Ala Leu Gly
                85                      90                      95

Ile Ile Asp Leu Lys Lys Lys Thr Ile Gly Tyr Val Asp Ser Leu Ser
               100                     105                     110

Asn Gly Pro Asn Ala Met Ser Phe Ala Ile Leu Thr Asp Leu Gln Lys
           115                     120                     125

Tyr Val Met Glu Glu Ser Lys His Thr Ile Gly Glu Asp Phe Asp Leu
           130                     135                     140
```

NUCLEIC ACIDS ENCODING MICROBIAL SUMO PROTEASE HOMOLOGS

This application claims benefit of the filing date of U.S. Provisional Application No. 60/331,895, filed Nov. 20, 2001, and which is incorporated herein by reference.

This invention was made with United States Government support under grant number DBI-0078731 awarded by the National Science Foundation, and grant number GM60049 awarded by the National Institutes of Health. The U.S. Government has certain rights in this invention.

BACKGROUND OF THE INVENTION

1. Field of the Invention

The invention relates generally to the fields of medicine and cell biology and, more specifically, to the fields of infectious disease and regulation of apoptosis and inflammation.

2. Background Information

Post-translational modification of proteins is an important means of regulating protein activity, stability or localization. For example, post-translational modification of target proteins by conjugation to the small protein ubiquitin earmarks the target protein for degradation by the 26S proteasome. Recently, several small proteins have been identified with sequence similarity to ubiquitin and which modify target proteins. These ubiquitin-like modifiers (UBLs) include SUMO (small ubiquitin-related modifier), Rub1 (also called Nedd8), Apg8 and Apg12. In mammals, three members of the SUMO family have been described: SUMO-1, also known as PIC-1, sentrin or GMP1, which in humans is a 101 amino acid polypeptide; and the highly homologous polypeptides SUMO-2 and SUMO-3. Although SUMO-1 shares only about 18% sequence identity to ubiquitin, both polypeptides share a common three-dimensional structure.

The pathway of protein modification by sumoylation is analogous to the well-characterized pathway of modification by ubiquitination, although a different set of enzymes are involved. SUMO is initially made as an inactive precursor. The precursor is then processed by proteolytic cleavage to yield the active modifier polypeptide with an exposed carboxy-terminal glycine residue. The exposed glycine is required for the formation of an isopeptide bond between the carboxyl terminus of SUMO and a lysine residue of the target protein. This SUMO processing reaction is catalyzed by a cysteine protease known as a SUMO-specific protease. An E1-type activating enzyme, an E2-type conjugating enzyme, and an as-yet-unidentified E3-type ligase enzyme, are sequentially required for the conjugation of the processed SUMO to the target protein. The SUMO-specific protease that processes SUMO can also catalyze the cleavage of conjugated SUMO from the target protein.

Several known SUMO substrates are important modulators of apoptosis. Apoptosis, or programmed cell death, is involved in the development and homeostasis of multicellular organisms. Additionally, apoptosis of infected cells provides the host organism with an effective defense mechanism against pathogens. Alterations in the normal process of apoptosis occur in various pathological conditions, including cancer, autoimmune diseases, inflammatory conditions, degenerative syndromes and infectious diseases.

One SUMO target that plays a key role in apoptosis is the Promyelocytic Leukemia protein, or PML. The assembly and/or stability of PML nuclear bodies (PML NBs or PODs) is modulated by sumoylation of PML. It has been proposed that PML NBs are potential sites of protein degradation. Although the functions of PML NBs have not been fully defined, it is recognized that assembly of PML NBs is sensitive to environmental stimuli, and is compromised in pathological situations such as certain cancers and infectious disorders. PML NBs contain a number of proteins that are transiently recruited to the nuclear body, including the pro-apoptotic protein p53, various transcriptional regulators and proteasome components.

Another SUMO target that plays a key role in apoptosis is the inhibitor of the transcription factor NFκB, known as IκBα. NFκB is kept in an inactive form in the cytosol by binding to IκBα. Stimulation of the cell with various effectors, such as pro-inflammatory cytokines, various infectious agents and environmental stresses, leads to IκBα phosphorylation, ubiquitination and ultimately proteolytic degradation. NFκB is thus liberated from its inhibitor to enter the nucleus and activate its target genes, which include anti-apoptotic genes and genes involved in immune and inflammatory responses. SUMO competes with ubiquitin for modification of IκBα, as both modifiers target the same lysine residue of IκBα. The SUMO-modified pool of IκBα is protected from degradation, and the sumoylation of IκBα thus inhibits NFκB function.

A protein from the bacterial pathogen *Yersinia pestis*, YopJ, which is essential for virulence, has been shown to be a SUMO-specific protease (Orth et al., *Science* 290:1594-1597 (2000)). YopJ exerts its pathogenic effects on cells by disrupting post-translational modifications of a number of cellular substrates involved in the production of immune cytokines and anti-apoptotic factors. For example, YopJ expression prevents activation of the MAPK pathway and the NFκB pathway in the host, whereas catalytic domain mutants of YopJ do not affect these pathways. Therefore, SUMO-like protease activity is critical for microbial pathogenicity and host immune responses.

In view of the important role of SUMO-specific proteases in apoptosis, inflammation, host defenses against infectious agents, and other biological processes, there exists a need to identify novel microbial SUMO-specific proteases and molecules that regulate sumoylation. Such proteases and regulatory molecules can be used in the development of antibiotics, as well as in the development of therapeutic agents for the treatment of disorders of apoptotic regulation. The present invention satisfies this need and provides related advantages as well.

SUMMARY OF THE INVENTION

The invention provides isolated SUMO-specific protease-like (or "SSP") domain-containing polypeptides from microorganisms, including bacteria, protozoans and yeast, including *Eschericia, Salmonella, Pseudomonas, Chlamydia, Plasmodium, Trypanosma Mesorhizobium, Rickettsia, Cryptosporidium* and *Candida* species. Also provided are modifications thereof, functional fragments therefrom, and isolated peptides therefrom.

The invention further provides isolated nucleic acid molecules encoding SSP domain-containing polypeptides from *Eschericia, Salmonella, Pseudomonas, Chlamydia, Plasmodium, Trypanosma Mesorhizobium, Rickettsia, Cryptosporidium* and *Candida* species, and modifications and functional fragments therefrom. Also provided are vectors and cells containing such nucleic acid molecules, isolated oligonucleotides, and related detection methods.

Also provided are antibodies and antigen-binding fragments thereof that specifically bind SSP domain-containing polypeptides from microorganisms, including *Eschericia, Salmonella, Pseudomonas, Chlamydia, Plasmodium, Trypa-* nosma, *Mesorhizobium, Rickettsia, Cryptosporidium* and *Candida* species, and related detection methods.

The invention also provides a method of identifying a polypeptide that associates with a polypeptide comprising a SSP domain (a SSPAP). The method is practiced by contacting an SSP domain-containing polypeptide with a candidate polypeptide, and determining association between the polypeptides.

Further provided is a method of identifying a compound that associates with a polypeptide comprising a SSP domain (a SSPAC). The method is practiced by contacting an SSP domain-containing polypeptide with a candidate compound and determining association between the compound and the polypeptide.

The invention also provides a method of identifying a substrate of a polypeptide comprising a SSP domain (a SSPS). The method is practiced by contacting an SSP domain-containing polypeptide with a candidate polypeptide and determining proteolysis of the candidate polypeptide, wherein a polypeptide that is proteolysed is identified as a SSPS.

Also provided is a method of identifying a compound that modulates the proteolytic activity of a polypeptide comprising a SSP domain (a SSPMC). The method is practiced by contacting an SSP domain-containing polypeptide with a candidate compound and determining proteolytic activity of the polypeptide in the presence of said compound, wherein a compound that modulates the proteolytic activity of the polypeptide is identified as a SSPMC.

BRIEF DESCRIPTION OF THE DRAWINGS

FIG. 1 shows pairwise alignments of portions of several of the microbial SSP domain-containing polypeptides disclosed herein with known SUMO-specific proteases. A. Top: *C. trachomatis* (Residues 288-382 of SEQ ID NO:14); Bottom: human sentrin/SUMO-specific protease (SEQ ID NO:53). The catalytic triad residues are indicated by asterisks. B. Top: *E. coli* (Residues 129-357 of SEQ ID NO:2); Bottom: *S. cerevisiae* Ulp1 (scUlp1) protease (SEQ ID NO:54). C. Top: human sentrin/SUMO-specific protease (SEQ ID NO:55); Bottom: *P. syringae* (Residues 489-673 of SEQ ID NO:12). D. Top: human sentrin/SUMO-specific protease (SEQ ID NO:56); Bottom: *M. loti* (Residues 1,429-1,583 of SEQ ID NO:18). E. Top: scUlp1 (SEQ ID NO:57); Bottom: *R. conorri* (Residues 488-595 of SEQ ID NO:20). F. Top: scUlp1 (SEQ ID NO:58); Bottom: *C. albicans* (SEQ ID NO:22). G. Top: scUlp1 (SEQ ID NO:59); Bottom: *P. falciparium* (Residues 334-488 of SEQ ID NO:24).

FIG. 2 shows that proteins expressed in *Chlamydia trachomatis* (Tra-1) and in *Salmonella typhimurium* (S.pT) induce caspase-3 activity in HeLa cells (FIG. 2A) and in 293T cells (FIG. 2B).

FIGS. 3A and 3B show that proteins expressed in *Chlamydia trachomatis* (Tra-1), and in *Salmonella typhimurium* (S.pT) inhibit NF-kB activation.

DETAILED DESCRIPTION OF THE INVENTION

The invention provides molecules containing domains with structural similarity to eukaryotic SUMO-specific proteases (designated herein "SUMO-specific protease-like" or "SSP" domains), including SSP domain-containing polypeptides, encoding nucleic acid molecules, antibodies, and related compositions. Bacterial, protozoan and yeast SSP domain-containing molecules, like their homologs in mammals, regulate the post-translational modification of target proteins either within the pathogen or within infected host cells, thereby modulating the biological activity of these target proteins. Therefore, the invention SSP domain-containing molecules, and compounds that modulate the activity of these molecules, can be used therapeutically in the treatment of infectious diseases and in other conditions in which modulation of the activity of target proteins is warranted, such as inflammatory diseases.

As used herein, the term "SSP domain" refers to a region of about 150 to about 250 amino acids that exhibits recognizable structural and sequence homology with the catalytic domain of known SUMO-specific proteases, including yeast and human SUMO-specific proteases. Known eukaryotic SUMO-specific proteases, including the human proteases hSUSP1 (Kim et al., *J. Biol. Chem.* 275:14102-14106 (2000)), hSUSP2 and hSUSP3 (GenBank Accession Nos. AF199458 and AF199459, respectively), and the *S. cerevisiae* proteases scUlp1 and scUlp2 (Li et al., *Nature* 398:246-251 (1999)), share little overall sequence similarity outside of the active site. However, the residues of the catalytic triad (His, Asp and Cys) are well-conserved. Alternatively, the third residue in the catalytic triad can be Asp. As shown in FIG. 1, the SSP domains of the microbial polypeptides disclosed herein generally contain the conserved catalytic triad residues, as well as other regions of sequence similarity with known SUMO-specific proteases.

The characterization of a domain as a "SSP domain" can be confirmed using a Fold & Function Assignment System (FFAS) fold prediction calculation (Rychlewski et al., *Protein Sci.* 9:232-241 (2000)), using a database of proteins of known structures enriched in SUMO-specific protease domains.

An SSP domain can be characterized as containing the minimal fragment of the native polypeptide that is sufficient, when expressed alone, for proteolytic activity. For example, an SSP domain from *Saccharomyces cerevisiae* Ulp1 (residues 403-621 of ScUlp1) was shown to display the proteolytic activity of the full-length polypeptide in cleavage reactions with C-terminally tagged human SUMO-1 and yeast Smt3, producing their mature forms, and also to deconjugate an α-amine linked Smt3-GFP conjugate (Mossessova et al., *Mol. Cell* 5:865-876 (2000)).

The scUlp1/Smt3 crystal structure has been solved. Ulp1 contains several structural motifs directly involved in Smt3 binding and peptide hydrolysis that distinguish it from other families of cysteine proteases (see Mossessova et al., supra (2000)). Additional structural distinctions between SUMO proteases and other families of proteases are set forth in the Merops database (SUMO-specific proteases belong to clan CE). Structural analysis has revealed certain structural similarities between Ulp1 and deubiquitinating enzymes, and between the active site and substrate hole of Ulp1 and papain.

The microbial SSP domain-containing polypeptides disclosed herein, in view of their sequence and structural similarity to known SUMO-specific proteases, are predicted to be SUMO-specific proteases. However, alternatively it is contemplated that the disclosed SSP domain-containing polypeptides are ubiquitin-specific proteases, or have other substrates, such as similar substrates as papain-like enzymes.

As disclosed herein, SSP domain-containing molecules are present in members of diverse genera of pathogenic bacteria, including *Pseudomonas, Chlamydia, Eschericia, Salmonella, Mesorhizobium*, and *Rickettsia*, as well as in diverse genera of pathogenic protozoans, including *Plasmodium, Cryptosporidium* and *Trypanosoma*. The diseases caused by these microorganisms in humans, animals and plants are well known in the art. As disclosed herein, SSP domain-containing molecules are also present in the yeast *Candida albicans*.

For example, certain *Pseudomonas* species, such as *P. syringae*, are plant pathogens, whereas other species such as *P. aeruginosa* are human pathogens that causing serious opportunistic infections in individuals with cystic fibrosis and compromised immune systems.

*Chlamydia trachomatis* accounts for the major cause of blindness in Asia and Africa and is the most common sexually transmitted disease in the United States. *Chlamydia* infections have been linked to pelvic inflammatory disease, urethritis, infertility, arthritis, pneumonia, upper respiratory and ear infections, asthma, vascular diseases and cervical cancer.

*Plasmodium falciparum* and *Trypanosoma brucei* are insect protozoan parasites that cause malaria and sleeping sickness, respectively. Pathogenic strains of *Rickettsia* cause diseases such as spotted fever. The diseases caused by these pathogens are epidemic in many countries.

Pathogenic strains of *Eschericia* cause a variety of diseases, including diarrheal diseases and urinary tract infections. *Salmonella* infectious also have a variety of clinical manifestations, including gastroenteristis, typhoid fever and bacteraemia.

Cryptosporidiosis, caused by pathogenic strains of *Cryptosporidium*, accounts for up to 20% of all cases of childhood diarrhea in developing countries and is a potentially fatal complication of AIDS.

It is contemplated that any or all species of the above genera, and other genera of bacteria and protozoa, can express an SSP domain-containing polypeptide at some point in their life cycle. Therefore, compounds that modulate the expression or activity of these molecules can be used to prevent and treat infections caused by these microorganisms in humans, other animals and plants, and transmission of infection by insect vectors.

The invention provides isolated nucleic acid molecules encoding SSP domain-containing polypeptides. Such isolated nucleic acid molecules can be used, for example, as templates for the recombinant expression of SSP domain-containing polypeptides; in screening assays to identify cellular molecules that associate with or are substrates of SSP domain-containing polypeptides or compounds that promote or disrupt the function of SSP domain-containing polypeptides; as probes to detect SSP domain-encoding polypeptides in samples; in in vivo and ex vivo gene therapy applications to positively or negatively regulate protein sumoylation, microbial proliferation and pathogenicity, and/or host cell apoptosis; and in other therapeutic, diagnostic and screening applications known to those skilled in the art.

The term "isolated," in reference to an invention nucleic acid molecule or polypeptide is intended to mean that the molecule is substantially removed or separated from components with which it is naturally associated, or is otherwise modified by the hand of man, thereby excluding nucleic acid and polypeptide molecules as they exist in nature.

The term "nucleic acid molecule," as used herein, refers to an oligonucleotide or polynucleotide of natural or synthetic origin. A nucleic acid molecule can be single- or double-stranded genomic DNA, cDNA or RNA, and can represent the sense strand, the antisense strand, or both. A nucleic acid molecule can include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a hybridizing nucleic acid molecule is desired.

In one embodiment, the invention provides an isolated nucleic acid molecule encoding a polypeptide containing a microbial SSP domain. For example, the invention provides an isolated nucleic acid molecule encoding a polypeptide containing the SSP domain designated SEQ ID NO:27 from the *Eschericia coli* hypothetical protein b2269 from strain K-12 MG1655 (GenBank entries gi|7466311|pir||C64998; gi|1788604|gb|AAC75329.1|; gi|2498328|sp|Q47013|ELAD__ECOLI; and gi|1381662|gb|AAB02733.1|; SEQ ID NO:2). Also provided are isolated nucleic acid molecules encoding polypeptides containing an SSP domain from the b2269 homologs present in other *Eschericia coli* strains, including the SSP domain designated SEQ ID NO:42 from strain 0157:H7 (dbj|BA000007|; SEQ ID NO:41).

The invention also provides isolated nucleic acid molecules encoding polypeptides containing SSP domains from *Salmonella*, including the SSP domain designated SEQ ID NO:28 from *Salmonella paratyphi* A (gnl|WUGSC__32027|spara_B_SPA.0.21909; SEQ ID NO:4); the SSP domain designated SEQ ID NO:31 from *Salmonella typhi* CT18 (gnl|Sanger__601|S.typhi__Salmonella; SEQ ID NO:10); the SSP domain designated SEQ ID NO:30 from *Salmonella typhimurium* LT2 (gnl|WUGSC__99287|stmlt2-.Contig1457; SEQ ID NO:30) (gi|16420826|gb|AAL21188.1| (AE008802); gi|16765614|ref|NP__461229.1| (NC__003197); SEQ ID NO:51); and the SSP domain designated SEQ ID NO:29 from *Salmonella enteritidis* (gnl|UIUC__592|senteritdis__2153__10.21; SEQ ID NO:6)(gi|16503513|emb|CAD07520.1| (AL627274); SEQ ID NO:50). The native *Salmonella* SSP domain-containing polypeptides share extensive homology outside of the SSP domains with the native *E. coli* polypeptides.

The invention also provides isolated nucleic acid molecules encoding polypeptides containing SSP domains from *Pseudomonas*, including the SSP domain designated SEQ ID NO:32 from the *Pseudomonas syringae pv. eriobotryae* psvA gene (gi|6472616:2923-5118; SEQ ID NO:12) ORF3 polypeptide.

Further provided are isolated nucleic acid molecules encoding polypeptides containing an SSP domain from *Chlamydia* and *Chlamydophila*, including the SSP domain designated SEQ ID NO:33 from *Chlamydia trachomatis* (gi|7468961|pir||D71460[7468961; SEQ ID NO:14); the SSP domain designated SEQ ID NO:34 from *Chlamydia muridarum* (gb|AE002160|AE002160; SEQ ID NO:16); and the SSP domain from the homologous protein from *Chlamydophila psittaci* (gnl|TIGR__83554|cpsitt__148). The *Chlamydia* polypeptides designated SEQ ID NOS:14 and 16 contain a transmembrane domain sequence near the N-terminus.

Also provided are isolated nucleic acid molecules encoding polypeptides containing an SSP domain from *Mesorhizobium*, including the SSP domain designated SEQ ID NO:35 from *Mesorhizobium loti* (gi|13475280|ref|NP__106844.1| and gi|14026031|dbj|BAB52630.1|; SEQ ID NO:18).

The invention also provides isolated nucleic acid molecules encoding polypeptides containing an SSP domain from *Rickettsia*, including the SSP domain designated SEQ ID NO:36 from *Rickettsia conorri* (gi|15620199|gb|AAL03616.1; SEQ ID NO:20), and the SSP domain from the homologous protein from *Rickettsia prowazekii* (emb|AJ235269|RPXX0).

Also provided are isolated nucleic acid molecules encoding polypeptides containing an SSP domain from *Candida*, including the SSP domain designated SEQ ID NO:37 from *Candida albicans* (gnl|SDSTC_5476|C. albicans_Contig6-1621; SEQ ID NO:22).

Further provided are isolated nucleic acid molecules encoding polypeptides containing an SSP domain from *Plasmodium*, including the SSP domain designated SEQ ID NO:38 from *Plasmodium falciparium* (gnl|pf12|Stanford_Chr12Contig05.001215; SEQ ID NO:24).

Also provided are isolated nucleic acid molecules encoding polypeptides containing an SSP domain from *Tyrpanosoma*, including the SSP domain designated SEQ ID NO:39 from *Tyrpanosoma brucei* (gnl|TIGR_56911|T. brucei_32P4.TR; SEQ ID NO:26).

The invention also provides isolated nucleic acid molecules encoding polypeptides containing an SSP domain from *Cryptosporidium*, including the SSP domain designated SEQ ID NO:45 from *Cryptosporidium parvum* (gnl|CVMUMN_5807|cparvum_Contig1799; SEQ ID NO:44).

Also provided are isolated nucleic acid molecules encoding polypeptides comprising substantially the same amino acid sequence as the SSP domains designated SEQ ID NOS: 27-39, 42 or 45. The term "substantially the same amino acid sequence," or "modification," refers to amino acid sequences having at least about 40% identity with respect to the reference amino acid sequence, and retaining comparable biological activity characteristic of the polypeptide defined by the reference amino acid sequence. Polypeptides having "substantially the same amino acid sequence" or that are "modifications" can also have at least about 50%, 60%, 70%, 80%, 85%, 90%, 92%, 95%, 98% or greater amino acid sequence identity with respect to the reference sequence, while retaining comparable biological activity.

Identity of any two nucleic acid or amino acid sequences can be determined by those skilled in the art based, for example, on a BLAST 2.0 computer alignment. BLAST 2.0 searching is known in the art and is publicly available, for example, at ncbi.nlm.nih.gov/BLAST/, as described by Tatusova et al., FEMS Microbiol Lett. 174:247-250 (1999).

Based on the identification of SSP domain-containing polypeptides in members of a variety of bacterial, protozoan and yeast genera, it is contemplated that SSP domain-containing polypeptides are widely expressed in bacteria, protozoans and yeast. Methods to identify other SSP domain-encoding nucleic acid molecules and encoded polypeptides that are substantially the same as the reference sequences include analysis of microbial DNA databases to identify structurally similar molecules, according to the methods disclosed herein (see Example).

Alternative methods to identify SSP domain-encoding nucleic acid molecules and encoded polypeptides that are substantially the same as the reference sequences include hybridization-based or antibody-based DNA library screening methods to identify molecules with similar primary sequence. DNA libraries, including expression libraries, from a variety of bacterial and eukaryotic species are commercially available or can be readily prepared, and can be probed with SSP domain-encoding nucleic acid molecules, amplified using oligonucleotide primers, or contacted with antibodies, according to methods known in the art. From an initially identified fragment, nucleic acid molecules encoding full-length polypeptides can be obtained, if desired, by a variety of methods well-known in the art, such as 5' and 3' RACE.

A polypeptide having substantially the same amino acid sequence as a reference SSP domain can have, for example, one or more additions, deletions or substitutions compared with the reference amino acid sequence. Such modifications can be advantageous, for example, in enhancing the stability, bioavailability, bioactivity or immunogenicity of the polypeptide, or to facilitate its purification.

Modifications to the recited amino acid sequences can be randomly generated, such as by random insertions, deletions or substitutions of nucleotides in a nucleic acid molecule encoding the polypeptide. Alternatively, modifications can be directed, such as by site-directed mutagenesis of an encoding nucleic acid molecule.

Computer programs known in the art can provide guidance in predicting which amino acid residues can be modified without abolishing the function of the polypeptide. Additionally, guidance in modifying amino acid residues of a SSP domain containing polypeptide, while retaining function can be provided by structure-function studies of other cysteine proteases, including other SUMO-specific proteases. It is well known in the art that evolutionarily conserved amino acid residues and structural motifs are more likely to be important for maintaining biological activity than less well-conserved residues and domains. For example, deletion or substitution of the conserved His, Asp and Cys residues of the catalytic triad, or other modifications that disrupt the conformation of the protease active site, are expected to abolish enzymatic activity, whereas modifications of less conserved residues, or residues that do not affect the conformation of the active site are expected to be better tolerated.

Thus, it would be expected that substituting a residue that that is highly conserved among SSP domain-containing polypeptides across microbial species with a non-conserved residue may be deleterious, whereas making the same substitution at a residue which varies widely among species would likely not have a significant effect on biological activity. The skilled person, based on the alignments shown in FIG. 1 and knowledge of the important structural role of the conserved active site residues, could predict the effect of modifications, and test the biological activity of the modified polypeptide by the methods described herein.

Substitutions to a recited amino acid sequence can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to a recited amino acid sequence designated include, but are not limited to, the addition of "tag" sequences, such as epitope tags, histidine tags and glutathione-S-transferase (GST), and the like, as well as localization sequences (e.g. membrane localization sequences) and sorting sequences. Such additional sequences can be used, for example, to facilitate expression, purification or characterization of a recombinant polypeptide or to direct the localization of the polypeptide to a desired cellular location.

Deletions to a recited amino acid sequence include, but are not limited to, deletion of residues at the N- and C-termini, or between conserved helices, that are not critical for function.

The SSP domain-containing polypeptides of the invention will have one or more biological activities of the full-length, native polypeptide, or one or more activities of a known SUMO-specific protease.

Biological activities of an invention SSP domain-containing polypeptide include, for example, proteolytic activity towards a substrate. Proteolytic activity can be determined by any method that directly or indirectly detects cleavage of a substrate. For example, proteolysis of the substrate SUMO can be evidenced by either processing of immature SUMO, proteolytic deconjugation of SUMO from a substrate, or both. Proteolysis of the substrate ubiquitin can likewise be determined by processing of immature ubiquitin, proteolytic deconjugation of ubiquitin from a substrate, or both. Methods of determining proteolytic activity toward other substrates are known in the art.

It is contemplated that one or more of the known SUMOs of the relevant host organism, or a Ubl from the microorganism itself, can be cleaved by each of the SSP domain-containing polypeptides described herein. It is contemplated that this cleavage occurs after the Gly-Gly residues near the C-terminus of the SUMO. It is also contemplated that this proteolytic activity can be blocked by incubation with the cysteine protease inhibitors N-ethylmaleimide or iodoacetamide, but not by incubation with serine protease inhibitors.

The sequences of SUMOs from host cells for infectious microorganisms are known in the art or can be readily determined. It is contemplated herein that mammalian SUMO-1, SUMO-2 or SUMO-3 homologs, including human SUMO-1, SUMO-2 or SUMO-3, can be proteolytically cleaved by the SSP domain-containing polypeptides of the invention. The sequences of SUMO-1, SUMO-2 or SUMO-3 from various species are known in the art, and the human sequences are presented, for example, in Muller et al., *Nature Reviews* 2:202-210 (2001). Yeast and other invertebrates apparently have only a single SUMO gene, termed "SMT3." It is also contemplated herein that SMT3 and its homologs in host cells can be proteolytically cleaved by the SSP domain-containing polypeptides of the invention.

In order to assay SUMO-specific proteolytic activity of the polypeptides of the invention, SUMOs conjugated either to biologically relevant SUMO substrates, or to convenient test substrates, can be contacted with purified or partially purified SSP domain-containing polypeptide, and cleavage of the SUMO from the substrate detected. Various methods of determining cleavage of two proteins are well known in the art. Useful methods can involve, for example, detectably labeling the SUMO or the substrate, such as with a radiolabel, fluorochrome, or epitope tag; the use of binding agents, such as antibodies, that recognize the SUMO or the substrate; and the use of separation methods that distinguish between conjugated and deconjugated proteins.

Appropriate SUMO substrates from various species are known in the art or can be readily determined. Biologically relevant mammalian SUMO substrates include, for example, RanGAP1, PML, Sp100, p53, p73, HIPK2, TEL, c-Jun, Androgen Receptor, IκBα, Mdm2, Topo I, Topo II, WRN, RanBP2, GLUT1 and GLUT4. Other SUMO substrates are described, for example, in Muller et al., supra (2001). The substrate Lys residue through which the SUMO becomes conjugated for each of these proteins is known in the art or can be determined by the skilled person.

An example of an assay for SUMO proteolytic activity is provided by Kim et al., *J. Biol. Chem.* 275:14102-10406 (2000). In the assays described therein, *E. coli* cells were transfected with constructs that recombinantly express various ubiquitin-like modifiers (Ubls) (e.g. SUMO1, Smt3, Ub, Rub1, NEDD8 and Fub), conjugated to various proteins (e.g. RanGAP1, PESTc, β-galactosidase). Cell extracts were then contacted with a partially purified putative SUMO-specific protease. Proteolytic activity by the putative SUMO-specific protease was evidenced by an increase in mobility of the protein band on an immunoblot, indicating hydrolysis of the Ubl from the conjugated protein. The skilled person could readily adapt this assay, or other in vitro or in vivo proteolytic assays known in the art, to determine or confirm the activity and substrate specificity of an SSP domain-containing polypeptides of the invention.

Methods to determine SUMO-specific proteolytic activity in vivo are also known in the art. For example, the proteolytic activity of the *Yersinia pestis* SUMO-like protease YopJ was determined by detecting proteolytic release of HA-tagged SUMO-1 from a SUMO-1 conjugate in mammalian cells that recombinantly expressed both YopJ and the SUMO-1 conjugate, and further expressed GST-BRaf (see Orth et al., *Science* 290:1594-1597 (2000)). Similar in vivo methods can be used to determine or confirm the proteolytic activity of an SSP domain-containing polypeptides of the invention.

SSP biological activity can also be determined indirectly by monitoring the effect of recombinant expression of an SSP domain-containing polypeptide on a cellular process mediated by sumoylation. For example, sumoylation of the promyelocytic (PML) protein is required for localization of the protein to PML-oncogenic domains or nuclear bodies (PODs, or NBs) in the nucleus, and for subsequent recruitment of other NB proteins, including Daxx and Sp100. The localization of PML or other NB-localized proteins to NBs can be determined, for example, by immunolocalization methods known in the art, such as immunfluorescence labeling and confocal microscopy (Zhong et al., *Blood* 95:2748-2753 (2000); Muller et al., *EMBO J.* 17:61-70 (1998); Ishov et al., *J. Cell Biol.* 147:221-223 (1999)). Accordingly, SUMO-specific proteolytic activity of a recombinantly expressed SSP domain-containing polypeptide can be determined by detecting aberrant localization of PML and other NB-localized proteins, which results from desumoylation of PML.

As a further example, sumoylation of the p53 negative regulatory protein Mdm2 protects Mdm2 from self-ubiquitation and degradation, thereby enhancing the degradation of p53 (Buschmann et al., *Cell* 101:753-762 (2000); Melchior et al., *Nature Cell Biol.* 2:E161-E163 (2000)). Thus, SUMO-specific proteolytic activity of a recombinantly expressed SSP domain-containing polypeptide can be determined by detecting decreased Mdm2, or the resulting increased abundance or transcriptional activity of p53. However, sumoylation of p53 enhances its transcriptional activity (Melchior et al., supra (2000); Gostissa et al., *EMBO J.* 18:6462-6471 (1999)). Thus, SUMO-specific proteolytic activity of a recombinantly expressed SSP domain-containing polypeptide can be determined by detecting decreased transcriptional activity of p53. As p53 is an inducer of apoptosis, SUMO-specific proteolysis can thus have either positive or negative effects on apoptosis.

Methods of detecting apoptosis in vivo and in cell-free systems are well known in the art (see, for example, Reed, ed., *Meth. Enz.* Vol. 322 (2000), particularly Chapters 1-5 and 15-17). For example, DNA fragmentation is characteristic of apoptosis, and kits for detecting DNA fragmentation, such as the Apoptag™ detection kit (Intergen, Purchase, N.Y.), are commercially available. Alternatively, pulsed-field gel electrophoresis and conventional agarose gel electrophoresis can be used to detect DNA fragmentation.

An alternative method of detecting apoptotic activity is to detect caspase activation, which only occurs during apoptosis. For example, Su et al., *Exp. Neurol.* 163:9-19 (2000) describes detecting a cleavage product of an endogenous caspase substrate using CM1 antibody (IDUN Pharmaceuticals, La Jolla, Calif.) to detect the p18 subunit of processed, active caspase-3. Caspase activation can also be determined using an exogenous substrate. For example, Haraguchi et al., *J. Exp. Med.* 191:1709-1720 (2000) describes detecting caspase activation using various commercially available fluorigenic substrate peptides, and monitoring release of the fluorigenic moiety from the substrate peptide using a fluorimeter plate reader.

A further method of detecting apoptotic activity is based on the observation that an early event in apoptosis is translocation of phosphatidylserine (PS) to the cell surface. Annexin V has been shown to specifically bind PS. Accordingly, such an assay can employ annexin V-FITC/propidium iodide staining and two-color FACS analysis. Apoptotic cells can be characterized as annexin V positive, but propidium iodide negative (Haraguchi et al., supra (2000)).

Another method of detecting apoptotic activity is based on the observation that loss of mitochondrial membrane potential occurs as an early event in apoptosis. A change in mitochondrial membrane potential can be detected using a potential-sensitive dye, such as rh123, carbocyanine $DiOC_6$, TREM and the like (Haraguchi et al., supra (2000)). Cells at early stages of apoptosis can be distinguished from necrotic cells or late apoptotic cells with impaired membrane integrity in this method using propidium iodide staining.

A further of detecting apoptosis is to directly determine modulation of cell death and survival. For example, recombinant expression of Bax in *S. cerevisiae* induces apoptotic cell death. The lethal effect of Bax can be reverted by co-expression of anti-apoptotic Bcl-2 family members. Therefore, reversion of the lethal effect of overexpressed Bax (or other pro-apoptotic protein) in yeast (or other convenient dell type) is indicative of anti-apoptotic activity (see Xu et al., *Meth. Enz.* 322:283-296 (2000)).

Other methods of detecting apoptosis suitable for a particular application can be determined by those skilled in the art.

Furthermore, sumoylation of the NFκB inhibitor IκBα prevents IκBα degradation and NFκB liberation, thus preventing NFκB function. SUMO-specific proteolytic activity of a recombinantly expressed SSP domain-containing polypeptide or the effect of expression of an SSP-domain containing polypeptide can be determined by detecting modulated NFκB activity. Various methods of determining the amount of NFκB activity in a cell are well known in the art. For example, binding assays have been developed that take advantage of the observation that active NFκB found in nuclear fractions binds to DNA, but inactive NFκB is located in the cytosol. Therefore, the binding of a test nuclear extract to a labeled oligonucleotide containing an NFκB consensus binding site can be assayed. Active NFκB in the nuclear extract is evidenced by retardation of the mobility of the oligonucleotide band on a gel (Schreck et al., *Nucleic Acids Res.* 18:6497-6502 (1990); Rusher et al., *J. Biotech.* 78:163-170 (2000)). An alternative method is to attach an oligonucleotide containing an NFκB consensus binding site to a multi-well plate and detect bound, active NFκB in an ELISA-type assay using NFκB antibodies (Renard et al., *Nucleic Acids Res.* 29:E21 (2001)).

Activity assays can also be used to determine the amount of NFκB activity in a cell. For example, a reporter gene such as the luciferase, β-galactosidase or secretory alkaline phosphatase gene can be placed under the control of a promoter containing the NFκB consensus site. NFκB activity in cells transfected with the reporter construct is evidenced by expression of the product of the reporter gene (Moon et al., *Anal. Biochem.* 292:17-21 (2001); see Examples).

Additional methods of monitoring events associated with NFκB activation include, for example, monitoring cytoplasmic IκB degradation using antibodies directed against IκB (Sun et al., *Proc. Natl. Acad. Sci. USA* 91:1346-1350 (1994), monitoring exposure of the nuclear localization signal (NLS) of active NFκB using NLS-specific antibodies (Zabel et al., *EMBO J.* 12:201-211 (1993)), and monitoring the cleavage of the NFκB precursors p100 or p105 to the active p50 or p55 subunits (see, for example, Lin et al., *Mol. Cell. Biol.* 16:2248-2254 (1996); Morgan et al., *Cancer Res.* 59:6205-6213 (1999); Uren et al., *Mol. Cell* 6:961-967 (2000)).

In the assays described above, the skilled person can employ appropriate controls to confirm that the observed effect is a result of a biological activity of an SSP domain-containing polypeptide. For example, the effect of the SSP domain-containing polypeptide on the particular substrate or cellular activity can be compared to the effect on the substrate or cellular activity either in the absence of the polypeptide or in the presence of an SSP domain-containing polypeptide that has been mutated at the predicted catalytic site residues.

Further provided are isolated oligonucleotides containing at least 17 contiguous nucleotides of a SSP domain-encoding nucleic acid molecule or of its complement. An isolated oligonucleotide can thus contain at least 18, 19, 20, 22, or at least 25 contiguous nucleotides, such as at least 30, 40, 50, 60, 70, 80, 90, 100, 125, 150, 175, 200, 225, 250, 275, 300, 350, 400, 500, 600, 700, 800 or more contiguous nucleotides from the reference nucleotide sequence, up to the full length sequence. An invention oligonucleotide can be single or double stranded, and represent the sense or antisense strand. An invention oligonucleotide can, but need not, encode a functional polypeptide and can, but need not, be inserted into a vector.

In one embodiment, the isolated oligonucleotide comprises at least 17 contiguous nucleotides of the SSP-domain encoding portion of any of SEQ ID NOS:1, 3, 5, 7, 9, 11, 13, 15, 17, 19, 21, 23, 25, 40 or 43, or the complement thereof. Such oligonucleotides are able to specifically hybridize to a SSP domain-encoding nucleic acid molecule under highly stringent hybridization conditions. Therefore, the invention oligonucleotides can be advantageously used, for example, as probes to detect bacterial SSP domain-encoding nucleic acid molecules in a sample; as sequencing or PCR primers; as antisense reagents to block transcription of a SSP domain-encoding nucleic acid molecule in a bacterial or infected host cell; or in other applications known to those skilled in the art in which hybridization to a SSP domain-encoding nucleic acid molecule is desirable.

Specific hybridization refers to the ability of a nucleic acid molecule to hybridize to the reference nucleic acid molecule without hybridization under the same conditions with nucleic acid molecules that are not the reference molecule, such as actin cDNA. Moderately stringent hybridization conditions are conditions equivalent to hybridization of filter-bound nucleic acid in 50% formamide, 5× Denhart's solution, 5×SSPE, 0.2% SDS at 42° C., followed by washing in 0.2× SSPE, 0.2% SDS, at 50°. Highly stringent conditions are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 65° C. Other suitable moderately stringent and highly stringent hybridization buffers and conditions are well known to those of skill in the art and are described, for example, in Sambrook et al., *Molecular Cloning: A Laboratory Manual*, 3rd ed., Cold Spring Harbor Press, Plainview, N.Y. (2001) and in Ausubel et al. (*Current Protocols in Molecular Biology* (Supplement 47), John Wiley & Sons, New York (1999)).

An invention nucleic acid molecule or oligonucleotide containing a SSP domain-encoding nucleotide sequence can further contain nucleotide additions, which optionally can be encode additional polypeptide sequence as described above. Other additional nucleotide sequences include, for example, sequences that facilitate identification or purification of the oligonucleotide, and sequences that facilitate cloning, such as restriction endonuclease recognition sites.

In one embodiment, the invention provides a primer pair containing an isolated oligonucleotide containing at least 17 contiguous nucleotides of a SSP domain-encoding nucleic acid molecule and an isolated nucleic acid molecule containing at least 17 contiguous nucleotides of the complement of a SSP domain-encoding nucleic acid molecule. The primer pair can be used, for example, to amplify a SSP domain-encoding nucleic acid molecule by the polymerase chain reaction (PCR). The skilled person can determine an appropriate primer length and sequence composition for the intended application.

The isolated SSP domain-encoding nucleic acid molecules and oligonucleotides of the invention can be produced or isolated by methods known in the art. The method chosen will depend, for example, on the type of nucleic acid molecule one intends to isolate. Those skilled in the art, based on knowledge of the nucleotide sequences disclosed herein, can readily isolate SSP domain-containing nucleic acid molecules as genomic DNA, or regulatory sequences therefrom; as full-length cDNA or desired fragments therefrom; or as full-length mRNA or desired fragments therefrom, by methods known in the art.

An invention SSP domain-containing polypeptide, functional fragment or peptide does not consist of the exact sequence of the amino acid sequence set forth in publically available databases, or of the exact amino acid sequence of a translated product of a nucleic acid molecule set forth in publically available databases. Likewise, an invention nucleic acid molecule encoding a SSP domain or functional fragment, or SSP domain oligonucleotide, does not consist of the exact sequence of a nucleotide sequence set forth in publically available databases, such as Expressed Sequence Tags (ESTs), Sequence Tagged Sites (STSs) and genomic fragments, deposited in public databases such as the nr, dbest, dbsts and gss databases and TIGR, SANGER center, WUST1 and DOE databases of microbial genomes.

In certain embodiment, specifically excluded from the invention polypeptides and nucleic acid molecules are molecules having the exact sequence (or encoding nucleotide or encoded polypeptide sequence) set forth in any of the following: gi|7466311|pir||C64998; gi|1788604|gb|AAC75329.1|; gi|2498328|sp|Q47013|ELAD__ECOLI gi|1381662|gb|AAB02733.1|; dbj|BA000007|; gb|AE005174|; gnl|WUGSC__32027|spara_B__SPA.0.21909; gnl|Sanger__601|S. typhi__Salmonella; gnl|WUGSC__99287|stmlt2-.Contig1457; gnl|UIUC__592|senteritdis__2153__10.21; gi|6472616:2923-5118; dbj|BA000012|; gi|7468961|pir||D71460[7468961; gb|AE002160|AE002160; and gnl|TIGR__83554|cpsitt__148; gi|13475280|ref|NP__106844.1|; gi|14026031|dbj|BAB52630.1|; gi|15620199|gb|AAL03616.1|; emb|AJ235269|RPXX0; gnl|SDSTC__5476|C. albicans_Contig6-1621; gnl|pf12|Stanford_Chr12Contig05.001215; gnl|TIGR__5691|T. brucei__32P4.TR; gnl|CVMUMN__5807|cparvum__Contig1799; gi|16420826|gb|AAL21188.1| (AE008802); gi|16765614|ref|NP__461229.1| (NC__003197); gi|16503513|emb|CAD07520.1| (AL627274); and SEQ ID NOS:2, 4, 6, 8, 10, 12, 14, 16, 18, 20, 22, 24, 26, 41, 44, 50 or 51.

Since one of skill in the art will realize that the above-recited excluded database sequences may be revised at a later date, it is intended that the above-recited sequences are excluded as they stand on the priority date of this application.

One useful method for producing an isolated SSP domain-encoding nucleic acid molecule of the invention involves amplification of the nucleic acid molecule using the polymerase chain reaction (PCR) and specific primers and, optionally, purification of the resulting product by gel electrophoresis. Either PCR or reverse-transcription PCR (RT-PCR) can be used to produce a nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

Furthermore, isolated SSP domain-encoding nucleic acid molecules and oligonucleotides of the invention can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and nucleic acid molecules containing modified nucleotides or linkages.

The invention also provides a vector containing an isolated nucleic acid molecule encoding a SSP domain-containing polypeptide. The vectors of the invention are useful, for example, for subcloning and amplifying a SSP domain-encoding nucleic acid molecule, and for recombinantly expressing a SSP domain-containing polypeptide. A vector of the invention can include a variety of elements useful for cloning and/or expression of the encoded nucleic acid molecule, such as enhancer sequences and promoter sequences from a viral, bacterial or mammalian gene, which provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillin resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

If it is desired to express RNA transcripts or polypeptides, the invention nucleic acid molecule can be inserted into an expression vector such that it is operatively linked to a promoter of RNA transcription. The term "operatively linked," as used herein, is intended to mean that the nucleic acid molecule is positioned with respect to the endogenous promoter, or heterologous promoter, in such a manner that the promoter will direct the transcription of RNA using the nucleic acid molecule as a template. Methods for operatively linking a nucleic acid to a desired promoter are well known in the art and include, for example, cloning the nucleic acid into a vector containing the desired promoter, or appending the promoter to a nucleic acid sequence using PCR. Thus, an expression vector containing an invention nucleic acid molecule operatively linked to a promoter of RNA transcription can be used to express SSP domain transcripts and polypeptides in a desired host cell, or in an in vitro system, such as an extract or lysate that supports transcription and translation. Contemplated expression vectors include vectors containing regulatory sequences known in the art to provide for expression in bacterial cells, yeast cells, insect cells, amphibian cells, mammalian cells (including human, non-human primate and rodent cells) and other vertebrate cells.

A variety of expression vectors are commercially available, and can be further modified, if desired, to include appropriate regulatory elements to provide for the desired level of expression or replication in the host cell. For example, appropriate promoter and enhancer elements can be chosen to provide for constitutive, inducible or cell type-specific expression. Useful constitutive promoter and enhancer elements for expression of polypeptides in mammalian cells include, for example, RSV, CMV, SV40 and IgH elements. An exemplary inducible expression element is a steroid response element, while an exemplary cell-specific expression element is a prostate specific antigen (PSA) regulatory sequence. Other constitutive, inducible and cell type-specific regulatory elements are well known in the art.

Exemplary host cells that can be used to express recombinant molecules include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (e.g. *Drosophila*), yeast cells (e.g. *S. cerevisiae, S. pombe*, or *Pichia pastoris*) and prokaryotic cells (e.g. *E. coli*).

Methods for introducing a cloning or expression vector into a host cell are well known in the art and include, for example, various methods of transfection such as calcium phosphate, DEAE-dextran and lipofection methods, viral transduction, electroporation and microinjection. Host cells expressing invention nucleic acid molecules can be used, for example, as a source to isolate recombinantly expressed SSP domain-containing polypeptides, to identify and isolate molecules that regulate or interact with SSP domain-containing nucleic acids and polypeptides, or to screen for compounds that enhance or inhibit the activity of a SSP domain-containing polypeptide, as described further below.

The presence of a microbial SSP domain-containing molecule in a sample indicates the presence of the corresponding microorganism, and can also be indicative of the pathogenicity of the microorganism or the stage of infection. Thus, the invention provides methods for detecting a nucleic acid molecule encoding a bacterial SSP domain-containing polypeptide in a sample. This information can be useful, for example, to diagnose an infection, to determine the nature of the infectious microorganism, and for prognosis of the infection.

In one embodiment, the method is practiced by contacting a sample containing nucleic acids with one or more oligonucleotides containing contiguous sequences from an invention SSP domain-encoding nucleic acid molecule, under high stringency hybridization conditions, and detecting a nucleic acid molecule that hybridizes to the oligonucleotide. In an alternative embodiment the method is practiced by contacting a sample with a primer pair suitable for amplifying an invention SSP domain-encoding nucleic acid molecule, amplifying a nucleic acid molecule using polymerase chain reaction, and detecting the amplification.

As used herein, the term "sample" is intended to mean any biological fluid, cell, tissue, organ or portion thereof, or any environmental sample (e.g. soil, food, water, effluent and the like) that contains or potentially contains microbial SSP domain nucleic acid molecules or polypeptides. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

The methods of detecting a SSP domain-encoding nucleic acid molecule in a sample can be either qualitative or quantitative, and can detect the presence, abundance, integrity or structure of the nucleic acid molecule as desired for a particular application. Suitable hybridization-based assay methods include, for example, in situ hybridization, which can be used to detect altered chromosomal location of the nucleic acid molecule, altered gene copy number, and RNA abundance, depending on the assay format used. Other hybridization methods include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Suitable amplification-based detection methods are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. The amplified nucleic acid molecule can be sequenced to detect mutations and mutational hot-spots, and specific PCR-based assays for large-scale screening of samples to identify such mutations can be developed.

The invention also provides isolated polypeptides containing SSP domains, as described above with respect to polypeptides encoded by invention nucleic acid molecules. The invention polypeptides can be administered to cells (either directly or by recombinant expression) to modulate protein sumoylation, modulate host cell apoptosis, and/or prevent or ameliorate an infection. The invention polypeptides can also be used in screening assays to identify polypeptides and modulatory compounds that bind to and/or alter the activity of the SSP domain-containing polypeptides. Additionally, the invention polypeptides can be used to raise antibodies, which can be used in diagnostic and prognostic assays.

In one embodiment, the invention provides polypeptides containing SSP domains from *Eschericia, Salmonella, Pseudomonas, Chlamydia, Plasmodium, Trypanosma Mesorhizobium, Rickettsia, Cryptosporidium* and *Candida* species, including polypeptides containing the same or substantially the same amino acid sequence as the SSP domains designated SEQ ID NOS:27-39, 42 or 45.

A polypeptide of the invention can contain amino acids with various chemical or enzymatic modifications with respect to naturally occurring amino acids. Such modifications can enhance the stability, bioactivity, immunogenicity or other advantageous property of an invention polypeptide. Thus, a polypeptide can contain an amino acid modified by replacement of hydrogen by an alkyl, acyl, or amino group; by esterification of a carboxyl group with a suitable alkyl or aryl moiety; by alkylation of a hydroxyl group to form an ether derivative; by phosphorylation or dephosphorylation of a serine, threonine or tyrosine residue; by N- or O-linked glycosylation; by iodination; by radiolabeling; or the like. A polypeptide can also include a modified amino acids such as hydroxyproline or carboxyglutamate, or a D-amino acid in place of its corresponding L-amino acid. Those skilled in the art can determine an appropriate amino acid modification for a given application.

In yet another embodiment, the invention provides an isolated SSP domain peptide containing at least 8 contiguous amino acids of a microbial SSP domain-containing polypeptide, such as at least 8 contiguous amino acids of SEQ ID NOS:27-39, 42 or 45. Such a peptide can contain, for example, at least about 10, 12, 15, 20, 25, 30, 35, 40, 50, 60, 70, 80, 90, 100, 110, 125, 150, 200, 250, 300 or more amino acids, up to the full-length of the reference polypeptide. A peptide of at least about 8 amino acids can be used, for example, as an immunogen to raise antibodies specific for SSP domain containing polypeptides, or as an antigen to purify antibodies directed against SSP domain containing polypeptides. When used as an antigen, an invention peptide can be attached to a carrier molecule such as bovine serum albumin (BSA) or keyhole limpet hemocyanin (KLH).

Peptides that are likely to be antigenic or immunogenic can be predicted using methods and algorithms known in the art and described, for example, by Irnaten et al., *Protein Enq.* 11:949-955 (1998), and Savoie et al., *Pac. Symp. Biocomput.* 1999:182-189 (1999). Immunogenicity of the peptides of the invention can be determined by methods known in the art, such as assay of a delayed-type hypersensitivity response in an animal sensitized to a SSP domain-containing polypeptide, or by elicitation of antibodies specific for SSP domain-containing polypeptide. Likewise, antigenicity of the peptides of the invention can be determined by methods known in the art, such as by ELISA analysis, as described, for example, in Harlow and Lane, *Antibodies: A Laboratory Manual*, Cold Spring Harbor Laboratory Press (1988).

The isolated SSP domain-containing polypeptides and peptides of the invention can be prepared by methods known in the art, including biochemical, recombinant and synthetic methods. For example, polypeptides can be purified by routine biochemical methods from bacteria that express the polypeptide. The detection methods disclosed herein can be adapted for determining which bacteria are appropriate starting materials. Biochemical purification can include, for example, steps such as solubilization of the appropriate cells, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay.

A SSP domain-containing polypeptide or peptide having any desired boundaries can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, and similar affinity binding sequences. Methods for producing and expressing recombinant polypeptides in vitro and in prokaryotic and eukaryotic host cells are well known in the art.

Thus, the invention provides a method of isolating a SSP domain-containing polypeptide, by growing a host cell containing an expression vector encoding a SSP domain-containing polypeptide, under conditions appropriate for expression of the encoded polypeptide, and isolating the encoded polypeptide. In one embodiment, the SSP domain-containing polypeptide contains an amino acid sequence the same as or substantially the same an amino acid sequence designated SEQ ID NOS:27-39, 42 or 45.

The invention polypeptides and peptides can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990)).

The invention also provides an antibody or antigen binding fragment thereof which specifically binds to a SSP domain-containing polypeptide. Such antibodies, which include polyclonal, monoclonal, chimeric, bifunctional, and humanized antibodies, can be used, for example, to affinity purify a SSP domain-containing polypeptide from a cell, or in therapeutic and diagnostic applications described below.

An "antigen binding fragment" of an antibody of the invention includes, for example, individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments. Antigen binding fragments include, for example, fragments produced by protease digestion or reduction of an antibody, as well as fragments produced by recombinant DNA methods known to those skilled in the art.

In one embodiment, the invention provides antibodies and antigen binding fragments thereof that specifically bind a SSP domain-containing polypeptide containing an amino acid sequence designated SEQ ID NOS:27-39, 42 or 45.

The antibodies of the invention can be produced by any method known in the art. For example, a SSP domain containing polypeptide or immunogenic peptide of the invention, or a nucleic acid expressing such a polypeptide, can be administered to an animal, using standard methods, and polyclonal antibodies isolated therefrom. Such polypeptides or peptides, if desired, can be conjugated to a carrier, such as KLH, serum albumin, tetanus toxoid and the like, using standard linking techniques, to increase their immunogenicity. Additionally, such peptides can be formulated together with an adjuvant known in the art, such as Freund's complete or incomplete adjuvant. The antibodies so generated can be used in the form of serum isolated from an immunized animal, or the antibody can be affinity purified from the serum using the invention peptides or polypeptides.

Additionally, the antibodies of the invention can be monoclonal antibodies produced by a hybridoma cell line, by chemical synthesis, or by recombinant methods. Modified antibodies, such as chimeric antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual*, Cold Spring Harbor Laboratory, New York (1989); in Day, E. D., *Advanced Immunochemistry*, Second Ed., Wiley-Liss, Inc., New York, N.Y. (1990); and in Borrebaeck (Ed.), *Antibody Engineering*, Second Ed., Oxford University Press, New York (1995).

The invention also provides a method for detecting the presence of a polypeptide containing a microbial SSP domain in a sample. The method is practiced by contacting a sample with an antibody specific for an SSP domain-containing polypeptide and detecting the presence of specific binding of the antibody to the sample, thereby detecting the presence of a polypeptide containing a SSP domain in the sample. This information can be useful, for example, to diagnose an infection, to determine the nature of the infectious microorganism, and for prognosis, as described previously with respect to nucleic acid detection methods.

The invention also provides methods of identifying polypeptides and compounds that associate with or modulate the activity of a SSP domain-containing polypeptide. The term "modulate the activity" indicates either a positive or negative effect on a biological activity of a SSP domain-containing polypeptide. In embodiments of the methods described herein, polypeptides and compounds that associate with or modulate the activity of a SSP domain-containing polypeptide having the amino acid sequence designated SEQ ID NOS:27-39, 42 or 45 are provided. As described above, biological activities of SSP domain containing polypeptides that can be determined directly or indirectly include proteolysis of an immature SUMO, proteolytic cleavage of a SUMO from a conjugated substrate, proteolysis of an immature ubiquitin, proteolytic cleavage of ubiquitin from a conjugated substrate, as well as effects on cellular processes mediated by sumoylation, including modulation of PML localization, p53 stability and activity, apoptosis and NFκB activation. The identified polypeptides and compounds can be used in a variety of therapeutic applications, as described further below, such as to prevent or treat infectious diseases.

In one embodiment, the invention provides a method of identifying a SSP domain-associating polypeptide (a "SSPAP"). The method is practiced by contacting a SSP domain-containing polypeptide with a candidate polypeptide and determining association between the polypeptides. A polypeptide that associates with the SSP domain-containing polypeptide is identified as a SSPAP. As used herein, the term "associate" means that the molecule binds to the SSP domain-containing polypeptide relatively specifically and, therefore, can form a bound complex either in a cell or in vitro under suitable conditions.

Associations between polypeptides can be determined by methods known in the art. For example, associations with a SSP domain-containing polypeptide can be determined using transcription activation assays, affinity binding assays, co-immunoprecipitation assays, and the like. Various association assays are well known in the art and are described, for example, in Sambrook et al., supra (2001) and Ausubel et al., supra (1999).

Transcription activation assays such as two-hybrid assays are well known in the art. Such assays are based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two polypeptides. Two-hybrid systems can use various strains of *S. cerevisiae* as host cells for vectors that express the hybrid proteins. However, similar transcription activation assays also can be performed using other yeast cells or mammalian cells. The skilled person can practice the method by fusing an invention SSP domain containing polypeptide to a suitable DNA-binding domain or to a suitable trans-activation domain, and fusing one or more sequences potentially encoding a SSP to the other domain, and observing whether transcriptional activation occurs.

Affinity assays are also well known in the art and include, for example, assays in which the polypeptide of interest is fused to a glutathione-S-transferase (GST) protein, or to another tag that allows binding of the fusion to an affinity matrix. Such assays provide a simple, rapid and inexpensive method for identifying and isolating an associated polypeptide. For example, by recombinant expression, GST can be fused to a SSP domain-containing polypeptide of the invention, and the fusion expressed and purified by binding to an affinity matrix containing immobilized glutathione. A sample containing a candidate SSPAP, such as a bacterial or cellular extract or isolated polypeptide, can be passed over an affinity column containing the bound GST/SSP domain fusion, and a SSPAP obtained. In addition, fusion proteins can be used to screen a cDNA expression library, wherein binding of the SSP domain-containing protein to a clone indicates that the clone contains a cDNA encoding a SSPAP.

In another embodiment, the invention provides a method of identifying a SSP domain-associating compound (a "SSPAC"). The method is practiced by contacting a SSP domain-containing polypeptide with a candidate compound and determining association between the SSP domain-containing polypeptide and the candidate compound. A compound that associates with the SSP domain-containing polypeptide is identified as a SSPAC.

A candidate compound can be a naturally occurring macromolecule, such as a peptide, nucleic acid, carbohydrate, lipid, or any combination thereof. A candidate compound also can be a partially or completely synthetic derivative, analog or mimetic of such a macromolecule, or a small organic or inorganic molecule prepared partly or completely by combinatorial chemistry methods.

Methods for producing libraries of candidate compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

A compound that associates with a SSP domain-containing polypeptide can be identified using a variety of assay formats. A binding assay can use a detectably labeled candidate compound and an unlabeled SSP domain-containing polypeptide. Alternatively, a binding assay can use an unlabeled candidate compound and a labeled SSP domain-containing polypeptide. A variety of low- and high-throughput assays known in the art are suitable for detecting specific binding interactions between a SSP domain-containing polypeptide and a candidate compound. These assays include both solution-based methods and solid phase methods (e.g. molecules bound to plates, chips, affinity columns and the like). Such binding assays are amenable to either manual or high-throughput automated screening of compounds.

Suitable assays for detecting molecular associations include, for example, scintillation proximity assays (SPA) (Alouani, *Methods Mol. Biol.* 138:135-41 (2000)), UV or chemical cross-linking (Fancy, *Curr. Opin. Chem. Biol.* 4:28-33 (2000)), competition binding assays (Yamamura et al., *Methods in Neurotransmitter Receptor Analysis*, Raven Press, New York, 1990), biomolecular interaction analysis (BIA) such as surface plasmon resonance (SPR) (Weinberger et al., *Pharmacogenomics* 1:395-416 (2000)), mass spectrometry (MS) (McLafferty et al., *Science* 284:1289-1290 (1999) and Degterev, et al., *Nature Cell Biology* 3:173-182 (2001)), nuclear magnetic resonance (NMR) (Shuker et al., *Science* 274:1531-1534 (1996), Hajduk et al., *J. Med. Chem.* 42:2315-2317 (1999), and Chen and Shapiro, *Anal. Chem.* 71:669A-675A (1999)), and fluorescence polarization assays (FPA) (Degterev et al., supra, 2001). Other suitable methods to detect molecular associations are well known in the art (see, for example, Reed, ed., *Meth. Enz.* Vol. 322 (2000), particularly Chapters 24 and 25).

In another embodiment, the invention provides a method of identifying a substrate of a SSP domain containing polypeptide (a "SSPS"). The method is practiced by contacting a SSP domain-containing polypeptide with a candidate substrate and determining proteolytic cleavage of the candidate substrate by the SSP domain-containing polypeptide. A substrate that is cleaved by the SSP domain-containing polypeptide is identified as a SSPS. Exemplary substrates include, for example, mammalian SUMO1, SUMO2, SUMO3, yeast Smt3 and their homologs in other species. Other candidate substrates include, for example, the ubiquitin-like modifiers Ub, Rub1, NEDD8 and Fub, and other Ubls known in the art. These substrates can be the full-length, unprocessed Ubl, or the Ubl conjugated to a protein.

In another embodiment, the invention provides a method of identifying a compound that modulates the proteolytic activity of a polypeptide comprising a SSP domain (a SSPMC). The method is practiced by contacting a SSP domain-containing polypeptide with a candidate compound, and determining modulated proteolytic activity of the polypeptide in the presence of the compound. A compound that modulates the proteolytic activity of the SSP domain-containing polypeptide is identified as a SSPMC. Suitable proteolytic substrates and activity assays for determining enzymatic activity have been described previously.

In the methods described above, assays in the presence of a candidate compound or polypeptide will generally be compared to a control to determine the specificity and/or the magnitude of the effect. Suitable controls for the methods described herein, which include vehicle controls and irrelevant molecules as controls, are known in the art.

As described herein, microbial SSP domain-containing polypeptides can affect sumoylation of target proteins in infected host cells, thereby contributing to the pathogenic effects of the bacteria, protozoans and yeast in the host cells. As several sumoylation targets are important apoptotic regulators, including PML, p53 and IκBα, some of these effects can be manifested as altered host cell apoptosis, such as increased or decreased apoptosis. Microbial SSP domain-containing polypeptides can also affect sumoylation of target proteins in the microorganism itself that are important to its life cycle.

Alternatively or additionally, microbial SSP domain-containing polypeptides can affect ubiquitination of target proteins in infected host cells, thereby affecting the turnover of proteins in the proteosome. Many important regulators of the cell cycle and of apoptosis are ubiquitinated (reviewed, for example, in Yew, *J. Cell Physiol.* 187:1-10 (2001); and in Karin, *Annu. Rev. Immunol.* 18:621-623 (2000)).

Thus, by selectively manipulating the expression or biological activity of the SSP domain-containing molecules of the invention, sumoylation and/or ubiquitination of target proteins can be modulated, which can affect a variety of cell signaling pathways, including pathways that regulate apoptosis, host defenses against microbial infections, and inflammatory responses. Accordingly, selectively manipulating the expression or biological activity of the SSP domain-containing molecules of the invention can prevent or ameliorate infectious diseases caused by the pathogen.

The invention provides methods of modulating a biological activity in a cell, such as sumoylation or ubiquitination of a substrate protein, apoptosis, NFκB activation, and the like, by modulating the activity of a SSP domain-containing polypeptide. In embodiments of the method, a biological activity is modulated by modulating the activity of a SSP domain-containing polypeptide having the amino acid sequence designated SEQ ID NOS:27-39, 42 or 45. In one embodiment, the method is practiced by increasing or decreasing the level of a SSP domain-containing polypeptide in a cell. In another embodiment, the method is practiced by increasing or decreasing the level of a SSPAP, SSPC or functional fragment thereof in a cell. A "cell" can be either a microbial cell, or an infected host cell, such as a human, animal, insect or plant cell.

The level of a SSP domain-containing polypeptide in a cell can be increased by introducing an expressible nucleic acid molecule encoding the polypeptide into the cell, thereby increasing expression of the SSP domain-containing polypeptide. The SSP domain-containing polypeptide can have the same activity as the native polypeptide, or can act as in a dominant negative fashion to inhibit the activity of the native polypeptide. The method can be practiced either ex vivo or in vivo in an infected individual.

A nucleic acid molecule encoding a SSP domain-containing polypeptide can be introduced into a cell using gene transfer technology known in the art. Gene transfer strategies are well known to those skilled in the art, and successful clinical trials of gene therapy are described, for example in Roth et al., *Oncology* 13(10 Suppl 5):148-154 (1999). Gene transfer is generally practiced using expression vectors, such as viral vectors, viral genomes, plasmids, phagemids and the like, but can optionally be practiced with expressible DNA or mRNA encoding the desired polypeptide, without a vector.

Viral based gene transfer systems are advantageous in being able to introduce relatively high levels of a heterologous nucleic acid into a variety of cells, including nondividing cells. Viral vectors that are compatible with a targeted cell are particularly useful for introducing a nucleic acid molecule encoding a SSP domain-containing polypeptide or functional fragment into a cell. Suitable viral vectors for gene therapy applications are well known in the art, and include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731, 172), adeno-associated virus vectors (U.S. Pat. No. 5,604, 090), constitutive and regulatable retrovirus vectors (U.S. Pat. Nos. 4,405,712; 4,650,764 and 5,739,018, 5,646,013, 5,624, 820, 5,693,508 and 5,674,703), papilloma virus vectors (U.S. Pat. Nos. 5,674,703 and 5,719,054), and the like.

The targeting specificity of viral vectors can be utilized to target predetermined cell types and introduce a recombinant gene into the infected cell. Thus, the selection of viral vector will depend, in part, on the cell type to be targeted. For example, if neurodegenerative diseases are to be treated, then a vector specific for cells of the neuronal cell lineage can be used. Such viral vectors include, for example, Herpes simplex virus-based vectors. Similarly, if a disease or pathological condition of the hematopoietic system is to be treated, then a viral vector that is specific for blood cells and their precursors, preferably for the specific type of hematopoietic cell, can be used. Such viral vectors include, for example, HIV-based vectors. The skilled person can determine an appropriate vector for a particular indication to be treated.

Vectors such as those described herein also can express specific receptors or ligands, which can modify or alter target specificity through receptor mediated events. Such vectors can be constructed using recombinant DNA techniques or synthetic chemistry procedures. In addition, a viral vector can be made tissue-specific by incorporating a tissue-specific promotor or enhancer into the vector.

Recombinant adenoviruses having general or tissue-specific promoters can be used to deliver an expression construct into a variety of types of tissues and cells, including non-mitotic cells, and to drive cDNA expression in the target cells. Recombinant adeno-associated viruses also are useful and have the added advantage that the recombinant virus can stably integrate into the chromatin of even quiescent non-proliferating cells such as neurons of the central and peripheral nervous systems.

For gene therapy applications, an expression vector can be administered to a subject by various routes. For example, local administration at the site of a pathology can be advantageous because there is no dilution effect and, therefore, the likelihood that a majority of the targeted cells will be contacted with the nucleic acid molecule is increased. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule into cells in a tissue-specific manner using a tissue-specific ligand or an antibody that is non-covalently complexed with the nucleic acid molecule via a bridging molecule. Direct injection of a naked or a nucleic acid molecule encapsulated, for example, in cationic liposomes also can be used for stable gene transfer into non-dividing or dividing cells. In addition, an expressible nucleic acid molecule can be transferred into a variety of tissues using the particle bombardment method.

The level of a microbial SSP domain-containing polypeptide in a cell can be decreased, for example, by introducing an antisense nucleic acid molecule, ribozyme or double-stranded RNA interference construct into the cell. For example, antisense nucleotide sequences that are complementary to the 5'-region of a nucleic acid molecule encoding a SSP domain-containing polypeptide can be used to prevent translation. Therefore, the method can be practiced with an antisense nucleic acid molecule complementary to at least a portion of the nucleotide sequence of SEQ ID NOS: 1, 3, 5, 7, 9, 11, 13, 15, 17, 19, 21, 23, 25, 40 or 43, such as a region within nucleotides 1-100 of SEQ ID NOS: 1, 3, 5, 7, 9, 11, 13, 15, 17, 19, 21, 23, 25, 40 or 43, such as nucleotides 1-18 of SEQ ID NOS: 1, 3, 5, 7, 9, 11, 13, 15, 17, 19, 21, 23, 25, 40 or 43, and can optionally include sequences 5' to the start codon. Antisense nucleotide sequences that are complementary to other portions of SEQ ID NOS: 1, 3, 5, 7, 9, 11, 13, 15, 17, 19, 21, 23, 25, 40 or 43, including portions of the SSP domain-encoding sequence, can also be effective.

Methods of preparing antisense nucleic acids molecules and using them therapeutically are known in the art and described, for example, in Galderisi et al., *J. Cell Physiol.* 181:251-257 (1999). Likewise, methods of preparing ribozymes and DNA encoding ribozymes, including hairpin and hammerhead ribozymes, and using them therapeutically are known in the art and described, for example, in Lewin et al., *Trends Mol. Med.* 7:221-228 (2001). Such ribozymes can target and cleave a nucleotide sequence selected from SEQ ID NOS: 1, 3, 5, 7, 9, 11, 13, 15, 17, 19, 21, 23, 25, 40 or 43, such as portions of the SSP domain-encoding sequence.

RNA interference (RNAi) is a method of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., *Nature* 411:494-498 (2001); Bass, *Nature* 411:428-429 (2001); Zamore, *Nat. Struct. Biol.* 8:746-750 (2001)). dsRNAs of about 25-30 nucleotides have also been used successfully for RNAi (Karabinos et al., *Proc. Natl. Acad. Sci.* 98:7863-7868 (2001). Optionally, the dsRNA can be a hairpin construct (Svoboda et al., *Biochem. Biophys. Res. Commun.* 287:1099-1104 (2001)). dsRNA can be synthesized in vitro and introduced into a cell by methods known in the art. By such methods, the targeted RNA is degraded, and translation of the target polypeptide is decreased or abolished.

Antisense RNA, ribozymes and dsRNA nucleic acid molecules can be produced in a cell using expression vectors as described above. Alternatively, synthetic nucleic acid molecules can be introduced directly into cells or can be encapsulated in liposomes to facilitate transfer of the nucleic acid molecules into a cell. Where antisense oligonucleotides, ribozymes or dsRNA nucleic acid molecules are directly administered, it can be desirable to construct the nucleic acid molecules using nucleotide analogs or with a peptide nucleic acid backbone, in order to confer increased stability on the molecule in vivo.

Likewise, the levels of a SSPAP or a SSPS identified by the methods described herein, or a fragment thereof that associates with an invention SSP domain-containing polypeptide, can be increased or decreased by gene therapy, antisense, ribozyme or dsRNA methods as described above.

In another embodiment, the method of modulating a biological activity in a cell is practiced by contacting the cell with an effective amount of a SSPAC or a SSPMC. Methods of identifying SSPACs and SSPMCs have been described above.

In yet another embodiment, the method of modulating method of modulating a biological activity in a cell is practiced by contacting the cell with an effective amount of an antibody specific for a SSP domain-containing polypeptide. If desired, such antibodies can be administered in conjunction with a cytotoxic or cytostatic moiety, such as a radioisotope or toxin, in order to neutralize or kill cells expressing a microbial SSP domain-containing polypeptide.

In the methods described above, modulation of apoptosis can be evidenced in the microorganism itself or in infected host cells. Modulation of apoptosis refers to an increased or decreased amount of apoptosis, respectively, which can be manifested under normal conditions; under conditions in which other apoptotic molecules (such as adaptor proteins, caspases, cytokine receptors and the like) are over-expressed, deleted or mutated; under conditions in which apoptotic inducers, such as chemotherapeutic or anti-infective agents, have been applied; or under conditions of environmental stress, such as oxidative stress, nutrient deprivation, heat shock and the like. Methods for determining apoptosis have been described above.

The invention further provides a method of preventing or treating a pathologic condition in an individual by administering to the individual a therapeutic molecule described above, such as a nucleic acid molecule that directs the expression of a SSP domain-containing polypeptide; an antisense nucleic acid molecule or ribozyme that inhibits expression of a SSP domain-containing polypeptide; a SSPAC; a SSPMC; or an antibody antibodies. The invention molecules can be used to prevent or treat pathological conditions in humans and other mammals, including livestock, veterinary animals and research animals.

Pathologic conditions amenable to such methods are those that are characterized, at least in part, by altered sumoylation of target proteins, or altered apoptotis, such as infectious diseases, cancer, autoimmune diseases, neurodegenerative diseases and the like. In particular, infectious diseases mediated by the *Eschericia, Salmonella, Pseudomonas, Chlamydia, Plasmodium, Trypanosma, Mesorhizobium, Rickettsia, Cryptosporidium* and *Candida* that express the SSP domain containing polypeptides described herein, can be prevented or treated by such methods.

As used herein, the term "treating" a pathological condition is intended to mean any detectable beneficial therapeutic effect on the pathological condition of the individual being treating. The beneficial effect can be evidenced, for example, by a delayed onset of clinical symptoms, a reduction in severity of some or all clinical symptoms of the disease, a slower progression of the disease, a reduction in the number of relapses of the disease, a reduction in the number or activity of pathogenic cells, an improvement in the overall health or well-being of the individual, or by other parameters well known in the art that are specific to the particular condition.

The therapeutic molecules described herein can optionally be formulated together with a pharmaceutically acceptable carrier for delivery to a cultured cell or to an individual. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight protein; or another stabilizer or excipient. Pharmaceutically acceptable carriers, including solvents, stabilizers, solubilizers and preservatives, are well known to those skilled in the art.

Those skilled in the art can formulate the therapeutic molecules to ensure proper distribution in vivo. For example, the blood-brain barrier (BBB) excludes many highly hydrophilic compounds. To ensure that the therapeutic molecules of the invention cross the BBB, if desired, they can be formulated, for example, in liposomes, or chemically derivatized. Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include both biodegradable and non-degradable polymers and hydrogels. Those skilled in the art understand that the choice of the pharmaceutical formulation and the appropriate preparation of the composition will depend on the intended use and mode of administration.

The therapeutic molecules described herein can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously.

An effective dose of a therapeutic molecule described herein can be predicted, for example, by extrapolation from the concentration required to obtain the desired effect in the in vitro or in vivo assays described herein. An effective dose of a molecule of the invention can also be predicted from appropriate animal models for the particular disease. The appropriate dose for treatment of a human subject is dependent on the nature and bioactivity of the particular compound, the desired route of administration, the gender, age and health of the individual, the number of doses and duration of treatment, and the particular condition being treated, and can be determined by the clinician.

The following examples are intended to illustrate but not limit the present invention.

EXAMPLE I

Identification of Microbial SSP Domain-containing Molecules

An iterative search of sequence databases, using the algorithm and general approach described in Li et al., *Bioinformatics* 16:1105-1110 (2000), was performed with the catalytic domain of viral, yeast, *yersinia* and human SUMO-specific proteases (lavp, leuv, YopJ and C-terminal part of human SUMO-specific proteases). SSP domain-containing polypeptide sequences from *Eschericia, Salmonella, Pseudomonas, Chlamydia, Plasmodium, Trypanosma Mesorhizobium, Rickettsia, Cryptosporidium* and *Candida* were identified.

The candidate SSP domain-containing polypeptides were confirmed by running a Fold & Function Assignment System (FFAS) fold prediction calculation (Rychlewski et al., *Protein Sci.* 9:232-241 (2000)) against a database of proteins of known structures enriched in SUMO protease domains.

EXAMPLE II

Cloning and Characterization of Microbial SSP Domain-containing Molecules cDNAs encoding microbial SSP domain-containing polypeptides are cloned by PCR and incorporated into appropriate cloning and expression vectors. Sumoylase activity of recombinantly expressed SSP domain-containing polypeptides is determined in vitro and in cell-based assays. The effect of recombinantly expressed SSP domain-containing polypeptides on PML localization to nuclear bodies, Mdm2 stability, p53 stability and transcriptional activity, NFκB activity, apoptosis and other cellular processes is determined.

EXAMPLE III

Induction of Caspase-3 Activity and Inhibition of NF-κB Activation by SSP-domain Containing Polypeptides This example describes the effect of SSP-domain containing polypeptides on caspase-3 activity and NF-κB activation.

For bioinformatics analysis, Saturated Blast searches (Li et al., *Bioinformatics* 16:1105-1110 (2000)) were used to identify proteins expressed in *Chlamydia trachomatis* (Tra-1) and *Salmonella typhimurium* (S.pT) showing significant similarity to mammalian Peptidase C48 (or Ulp1 protease family). The predicted *C. trachomatis* membrane thiol protease CT868 (GI: 15605604) showed 26% identity with peptidase C48. The protein expressed in *S. typhimurium* (GI: 16765614) showed 27% identity with peptidase C48. Genomic DNA from *C. trachomatis* served as template for cloning CT868 using specific primers (forward primers 5'-GGAATTCATGTTGTCTCCCACCAACTCA-3', SEQ ID NO:46; reverse primer 5'-CCTCGAGTTAGAAAA-GAGCTTTTGCTTCAG-3', SEQ ID NO:47). Genomic DNA from *S. typhimurium* LT2 served as template for cloning S.pT using specific primers (forward primers 5'-GGAATTCAT-GAATATTATGTGTAAATTCACTTTA-3', SEQ ID NO:48; reverse primer 5'-CCTCGAGTACTCGCCATTACTG-GAGACT-3', SEQ ID NO:49). The S.pT gene is also found in *Salmonella paratyphi* and *Salmonella enteritidis*.

Plasmids were generated using PCR procedures with the primers described above (SEQ ID NOS:46-49) and designed to incorporate EcoRI and XhoI restriction sites. Polymerase chain reaction products were then digested and cloned into pcDNA3Myc vector. All plasmids were sequenced to verify the plasmids.

For cell culture and transfections, HEK293T and Hela cells were maintained in DMEM (Irvine Scientific; Santa Ana Calif.) and supplemented with 10% FBS, 1 mM L-glutamine, and antibiotics. HEK 293T and HeLa cells were grown in 60 mm petri dishes to 50% confluency and were transfected with 3 µg plasmid DNA using a lipofection reagent (Lipofectamine Plus reagent, Life Technologies/Invitrogen; Carlsbad Calif.). After 24 h and 48 h following transfections, both floating and adherent cells were recovered and pooled, and the percentage of transfected cells with green fluorescent protein (GFP) (green fluorescent cells) with nuclear apoptotic morphology was determined by staining with DAPI in Vectashield mounting medium.

For caspase assays, cytosolic extracts from HeLa and 293T cells were assayed for Caspase activity. Caspase activity was measured by release of 7-amino-4-trifluoromethyl-coumarin (AFC) from Ac-DEVD-AFC ("DEVD" disclosed as SEQ ID NO: 52) synthetic peptide using continuous-reading instruments as described previously (Deveraux et al., *Nature* 388: 300-304 (1997)).

To test the effect of Tra-1 and S.pT expression on caspase-3 activity, HeLa cells (FIG. 2A) or 293T cells (FIG. 2B) were transfected with pcDNA3Myc tagged empty plasmid or pcDNA3Myc plasmids encoding Tra-1 or S.pT. A pcDNA3Myc vector encoding Bax was used as a positive control. Caspase activity was measured in cell lysates at 48 hours after transfection using fluorogenic substrate Ac-DEVD-AFC ("DEVD" disclosed as SEQ ID NO: 52). Data are expressed as Relative Fluorescence Units (RFU) per 10 µg cytoplasmic proteins after a 1 hour reaction, which was empirically determined to be within the linear phase of the reactions.

As shown in FIG. 2, proteins expressed in *Chlamydia trachomatis* (Tra-1) and in *Salmonella typhimurium* (S.pT) induce caspase-3 activity. Tra-1 and S.pT expression increased caspase-3 activity in transfected HeLa cells (FIG. 2A) and in 293T cells (FIG. 2B).

For NF-kB reporter assays, 1×10$^4$ HEK293N cells were plated in 96-well plates and transfected using Superfect transfection reagent (Qiagen; Valencia Calif.) following the manufacturer's recommended protocol. Cells were transfected with 50 ng of pNF-κB-Luc (NF-κB-luciferase) and 10 ng of phRL-TK reporter vectors (Stratagene; La Jolla Calif.) and various amounts of the expression plasmids containing the bacterial genes. To maintain the total amount of DNA constant, various amounts of pcDNA3Myc empty vector were also transfected. At 72 h after transfection, activities from firefly and *Renillia luciferases* were assayed using the Dual-Luciferase Reporter Assay System (Promega; Madison Wis.).

To test the effect of Tra-1 and S.pT expression on NF-κB activation, HEK293N cells were seeded into 96-well plates and transfected on the following day with 50 ng of pNF-kB-luc and 10 ng of phRL-TK reporter gene plasmids (FIG. 3A). These plasmids were co-transfected with 500 ng of pcDNA3Myc empty vector, or with 200 ng of pcDNA3Myc encoding Tra-1 (Tra-1) or S.pT (S.pT). Cells were also transfected with 50 ng, 200 ng or 300 ng of a vector expressing a fusion protein, CD4/TLR4, a dominant activator of LPS receptor used as positive control in NF-kB activation (FIG. 3A).

As shown in FIG. 3B, HEK293N cells were transfected with 500 ng of pcDNA3Myc empty vector (pcDNA3Myc) or were transfected with 50 ng, 200 ng or 300 ng of a fusion protein, CD4/TLR4 (CD4/TLT450, CD4/TLT4 200, CD4/TLR4 300 respectively). Alternatively, cells were cotransfected with 200 ng of pcDNA3Myc encoding Tra-1 and 50 ng, 200 ng or 300 ng of CD4/TLR4 (Tra-1+CD4/TLR4 50, Tra-1+CD4/TLR4 200, Tra-1+CD4, respectively). The same experiments were performed using 200 ng of pcDNA3Myc encoding S.pT and with 50 ng, 200 ng or 300 ng of CD4/TLR4 (S.pT+CD4/TLR4 50, S.pT+CD4/TLR4 200, S.pT+CD4, respectively).

As shown in FIG. 3, proteins expressed in *Chlamydia trachomatis* (Tra-1) and in *Salmonella typhimurium* (S.pT) inhibit NF-κB activation. Expression of Tra-1 or S.pT did not increase NF-κB activity (FIG. 3A). Furthermore, expression of Tra-1 or S.pT in the presence of the NF-κB activator CD4/TLR4 inhibited NF-κB activation by CD4/TLR4 (FIG. 3B).

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

We claim:

1. An isolated nucleic acid molecule encoding a SUMO-specific protease-like domain (SSP domain) consisting of the amino acid sequence designated SEQ ID NO:27.

2. The nucleic acid molecule of claim 1, operatively linked to a promoter of RNA transcription.

3. A vector comprising the nucleic acid molecule of claim 1.

4. An isolated cell comprising the nucleic acid molecule of claim 1.

5. The isolated cell of claim 4, selected from the group consisting of a mammalian, a yeast and a bacterial cell.

6. The isolated cell of claim 5, wherein the isolated cell is a mammalian cell.

7. The isolated cell of claim 5, wherein the isolated cell is a yeast cell.

8. The isolated cell of claim 5, wherein the isolated cell is a bacterial cell.

9. A method of producing a polypeptide comprising an SSP domain, comprising expressing the nucleic acid molecule of claim 1 in vitro or in an isolated cell under conditions suitable for expression of said polypeptide.

* * * * *